(12) United States Patent  (10) Patent No.: US 12,390,664 B2
Chen et al.  (45) Date of Patent: Aug. 19, 2025

(54) SYSTEMS AND METHODS FOR DETERMINING A REGION OF INTEREST OF A SUBJECT

(71) Applicant: SHANGHAI UNITED IMAGING HEALTHCARE CO., LTD., Shanghai (CN)

(72) Inventors: Hushan Chen, Shanghai (CN); Wensong Chen, Shanghai (CN); Feng Yao, Shanghai (CN); Siqi Guo, Shanghai (CN); Wenbo Xue, Shanghai (CN); Yang Wang, Shanghai (CN); Zheng Zhang, Shanghai (CN); Tingrong Shi, Shanghai (CN); Ruiqi Song, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 71 days.

(21) Appl. No.: 18/321,745

(22) Filed: May 22, 2023

(65) Prior Publication Data

US 2023/0310895 A1 Oct. 5, 2023

Related U.S. Application Data

(62) Division of application No. 16/716,774, filed on Dec. 17, 2019, now Pat. No. 11,654,304.

(30) Foreign Application Priority Data

Dec. 17, 2018 (CN) .......................... 201811542434.9
Dec. 24, 2018 (CN) .......................... 201811582284.4

(Continued)

(51) Int. Cl.
*G06K 9/00* (2022.01)
*A61B 5/00* (2006.01)

(Continued)

(52) U.S. Cl.
CPC .......... *A61N 5/1049* (2013.01); *A61B 5/0035* (2013.01); *A61B 5/055* (2013.01);
(Continued)

(58) Field of Classification Search
CPC ......... A61B 6/0492; A61B 6/04; A61B 6/469; A61B 6/46; A61B 6/545; A61B 6/547; A61B 6/548; A61N 5/1049
See application file for complete search history.

(56) References Cited

U.S. PATENT DOCUMENTS 7,869,562 B2 * 1/2011 Khamene ............... A61B 6/583
 209/207
8,437,449 B2 * 5/2013 Riley .................... A61N 5/103
 378/65

(Continued)

FOREIGN PATENT DOCUMENTS

CN 1931094 A 3/2007
CN 101398397 A 4/2009

(Continued)

OTHER PUBLICATIONS

Somatom Edge Plus, Siemens Healthineers, https://www.siemens-healthineers.com/en-us/computed-tomography/single-source-ct/somatom-edge-plus.

(Continued)

*Primary Examiner* — Avinash Yentrapati
(74) *Attorney, Agent, or Firm* — METIS IP LLC

(57) ABSTRACT

Systems and methods for determining a target area relating to a subject situated on a table of a medical system are provided. The medical system may include a first device of a first modality and a second device of a second modality. In some embodiments, the system may: identify a second target area relating to the subject for performing a second operation using the second device; determine, based on the second (Continued)

target area, an initial target area relating to the subject for performing a first operation using the first device; and determine a first target area relating to the subject for performing the first operation using the first device by adjusting the initial target area.

20 Claims, 23 Drawing Sheets

(30) Foreign Application Priority Data

| | | |
|---|---|---|
| Apr. 15, 2019 | (CN) | ......................... 201910299074.2 |
| Aug. 28, 2019 | (CN) | ......................... 201910803126.5 |
| Oct. 24, 2019 | (CN) | ......................... 201911017130.5 |

(51) Int. Cl.

| | |
|---|---|
| *A61B 5/055* | (2006.01) |
| *A61B 6/00* | (2006.01) |
| *A61B 6/04* | (2006.01) |
| *A61B 6/46* | (2024.01) |
| *A61N 5/10* | (2006.01) |
| *G06V 10/145* | (2022.01) |
| *G06V 10/25* | (2022.01) |

(52) U.S. Cl.
CPC ............ *A61B 5/704* (2013.01); *A61B 6/0492* (2013.01); *A61B 6/469* (2013.01); *A61B 6/5247* (2013.01); *G06V 10/145* (2022.01); *G06V 10/25* (2022.01); *A61N 2005/1052* (2013.01); *A61N 2005/1055* (2013.01)

(56) References Cited

U.S. PATENT DOCUMENTS

| | | | | |
|---|---|---|---|---|
| 9,707,151 | B2* | 7/2017 | Woerlee | ............... A61H 31/004 |
| 9,753,111 | B2* | 9/2017 | Forthmann | .......... G01R 33/283 |
| 10,181,074 | B2* | 1/2019 | Braun | ..................... G06F 18/40 |
| 10,216,376 | B2* | 2/2019 | Hardie | .................. G06T 7/0012 |
| 10,315,054 | B2* | 6/2019 | Mead | ........................ G06T 7/85 |
| 10,789,498 | B2* | 9/2020 | Cao | ..................... A61B 5/1077 |
| 10,849,573 | B2* | 12/2020 | Joerger | .................. A61B 6/461 |
| 11,054,492 | B2* | 7/2021 | Faigle | ...................... A61B 5/06 |
| 2004/0081341 | A1* | 4/2004 | Cherek | .................... A61B 6/08 |
| | | | | 382/128 |
| 2006/0169288 | A1 | 8/2006 | Kleen et al. | |
| 2007/0189456 | A1 | 8/2007 | Haras | |
| 2009/0052760 | A1* | 2/2009 | Smith | ..................... G06T 7/593 |
| | | | | 382/132 |
| 2010/0215149 | A1* | 8/2010 | Takemoto | ........ A61B 17/12113 |
| | | | | 378/98 |
| 2011/0135190 | A1 | 6/2011 | Maad | |
| 2012/0140874 | A1 | 6/2012 | Li et al. | |
| 2013/0072781 | A1 | 3/2013 | Omernick et al. | |
| 2013/0156152 | A1* | 6/2013 | Boda | ..................... A61B 6/4441 |
| | | | | 378/20 |
| 2013/0279779 | A1* | 10/2013 | Darrow | .................. A61B 5/055 |
| | | | | 382/131 |
| 2013/0294570 | A1 | 11/2013 | Hansis | |
| 2014/0123388 | A1* | 5/2014 | Filiberti | ............... A61N 5/1049 |
| | | | | 5/601 |
| 2014/0176554 | A1 | 6/2014 | Cohen et al. | |
| 2014/0348401 | A1 | 11/2014 | Xu et al. | |
| 2015/0073255 | A1 | 3/2015 | Liu et al. | |
| 2015/0092906 | A1 | 4/2015 | Liu et al. | |
| 2015/0139520 | A1* | 5/2015 | Senegas | .............. G06F 18/2411 |
| | | | | 382/131 |
| 2015/0208989 | A1 | 7/2015 | Rackow et al. | |
| 2015/0297157 | A1 | 10/2015 | Mukumoto | |
| 2015/0351709 | A1 | 12/2015 | Dirauf et al. | |
| 2015/0366527 | A1 | 12/2015 | Yu et al. | |
| 2016/0074004 | A1* | 3/2016 | Braun | ..................... G06F 3/017 |
| | | | | 378/205 |
| 2016/0092078 | A1 | 3/2016 | Braun et al. | |
| 2016/0183890 | A1 | 6/2016 | Nathan | |
| 2016/0223633 | A1* | 8/2016 | Xiong | .................. G01R 33/543 |
| 2016/0232691 | A1* | 8/2016 | Nishii | ................... G06T 11/008 |
| 2016/0349975 | A1* | 12/2016 | Sugiura | ............... G06V 10/945 |
| 2016/0367169 | A1 | 12/2016 | Hardie et al. | |
| 2016/0381334 | A1 | 12/2016 | Poisner | |
| 2017/0202540 | A1 | 7/2017 | Shao et al. | |
| 2017/0228104 | A1 | 8/2017 | Ziraknejad et al. | |
| 2017/0311921 | A1* | 11/2017 | Feuerlein | ............... A61B 6/542 |
| 2017/0319165 | A1 | 11/2017 | Averbuch | |
| 2017/0347974 | A1 | 12/2017 | Izumo | |
| 2018/0140270 | A1* | 5/2018 | Profio | ..................... A61B 5/055 |
| 2018/0165808 | A1* | 6/2018 | Bagci | ..................... G06V 10/82 |
| 2018/0214241 | A1 | 8/2018 | Furuta et al. | |
| 2018/0314891 | A1 | 11/2018 | Ota et al. | |
| 2019/0012944 | A1 | 1/2019 | Hall et al. | |
| 2019/0046128 | A1* | 2/2019 | Yamazaki | .............. A61B 6/488 |
| 2019/0150873 | A1 | 5/2019 | Daum | |
| 2020/0121267 | A1* | 4/2020 | Deutschmann | ...... A61B 6/4452 |
| 2020/0178839 | A1* | 6/2020 | Krishnaiyer Raman | .................... A61B 6/0492 |
| 2020/0229737 | A1* | 7/2020 | Hao | ........................ A61B 6/04 |
| 2021/0259651 | A1 | 8/2021 | Liu et al. | |

FOREIGN PATENT DOCUMENTS

| | | |
|---|---|---|
| CN | 102113893 A | 7/2011 |
| CN | 103181775 A | 7/2013 |
| CN | 104000588 A | 8/2014 |
| CN | 104107063 A | 10/2014 |
| CN | 104869372 A | 8/2015 |
| CN | 106580356 A | 4/2017 |
| CN | 106691491 A | 5/2017 |
| CN | 107146266 A | 9/2017 |
| CN | 107273885 A | 10/2017 |
| CN | 107580204 A | 1/2018 |
| CN | 107661104 A | 2/2018 |
| CN | 107789001 A | 3/2018 |
| CN | 107833248 A | 3/2018 |
| CN | 107961035 A | 4/2018 |
| CN | 108765410 A | 11/2018 |
| CN | 109381212 A | 2/2019 |
| CN | 110136805 A | 8/2019 |
| DE | 10335037 A1 | 3/2005 |
| JP | 2010194004 A | 9/2010 |
| WO | 2005018456 A1 | 3/2005 |

OTHER PUBLICATIONS

The Extended European Search Report in European Application No. 19217233.6 mailed on Apr. 9, 2020, 6 pages.
First Office Action in Chinese Application No. 201811542434.9 mailed on Apr. 22, 2020, 20 pages.
First Office Action in Chinese Application No. 201811582284.4 mailed on May 25, 2020, 19 pages.
The Extended European Search Report in European Application No. 21216298.6 mailed on Apr. 21, 2022, 6 pages.
First Office Action in Chinese Application No. 201910803126.5 mailed on Nov. 17, 2022, 20 pages.
Yu, Jianming et al., Radiology Technology, Guidance Book for Advanced Health Professional and Technical Qualification Examination, 2017, 8 pages.
Meng, Fanbo et al., Testing method of SPECT/CT image registration, China Medical Imaging Technology, 31(11):1753-1757, 2015.

* cited by examiner

SYSTEMS AND METHODS FOR DETERMINING A REGION OF INTEREST OF A SUBJECT

CROSS-REFERENCE TO RELATED APPLICATIONS

This application is a divisional application of U.S. application Ser. No. 16/716,774, filed on Dec. 17, 2019, which claims priority of Chinese Patent Application No. 201811542434.9, filed on Dec. 17, 2018, Chinese Patent Application No. 201811582284.4, filed on Dec. 24, 2018, Chinese Patent Application No. 201910299074.2, filed on Apr. 15, 2019, Chinese Patent Application No. 201910803126.5, filed on Aug. 28, 2019, and Chinese Patent Application No. 201911017130.5, filed on Oct. 24, 2019, the contents of each of which are hereby incorporated by reference.

TECHNICAL FIELD

The disclosure generally relates to the field of medical devices, and more particularly relates to systems and methods for determining a region of interest of a subject for imagining and/or treatment.

BACKGROUND

A medical device such as an imaging device or treatment device is used to perform a non-invasive interaction with a subject (e.g., a human body or a part thereof) by a certain medium, such as for disease diagnostic, treatment or research purposes. In general occasions, before performing medical imaging or treatment, a radiology technician or doctor usually needs to manually move the table of the medical device to a target table position according to position guidance by laser (e.g., a laser lamp).

In some occasions, the medical device (e.g., a computed tomography (CT) device, a magnetic resonance imaging (MRI) device, a positron emission computed tomography (PET) device, a radiotherapy (RT) device, or a surgical robot) is set up in an examination room, while the corresponding control device thereof is set up in a control room separated from the examination room to protect the safety of the radiology technician or doctor. For example, during an imaging or treatment, the radiology technician needs to adjust the radiation dose and the imaging/treatment position according to information of the subject in the control device. In addition, before the imaging/treatment, the radiology technician or doctor needs to enter the examination room for helping the subject be set up on the table appropriately. After the initial setup, the radiology technician or doctor cannot directly obtain/confirm the information of the subject in the examination room but needs to go back and forth between the examination room and the control room. The aforementioned preparation process for scanning and/or treatment is cumbersome and time-consuming, which results in a low efficiency and/or quality of imaging or treatment.

In some embodiments, to perform a medical scan/treatment, once a scanning/treatment plan is finalized, the position of the table cannot be changed in the middle of scan/treatment. However, the efficacy of a well-defined scanning/treatment plan may depend on a proper setup, e.g., a satisfactory alignment between the center position of the table and the center position of the region of interest (ROI) (e.g., an organ). A proper setup for a whole-body scanning/treatment plan may be challenging. In some embodiments, to perform multi-modality scan using at least two devices of different modalities, due to the need to avoid moving the table, a scan using one of the at least two devices of a specific modality with a small field of view (FOV), compared to the other of the at least two devices, often does not cover the entire ROI.

Merely by way of example, to perform a PET/MRI scan on a human body, scan FOVs of PET and MRI may be set in concert. In some embodiments, the MRI protocol and the PET protocol may be based on a same isocenter. When the MRI scan and the PET scan are performed synchronously at a table position, because the PET scan has a relatively large FOV, the FOV of the MRI scan determined in concert with the FOV of the PET scan usually can not completely cover the complete ROI (e.g., a liver, an upper boundary of a kidney being outside the FOV).

As another example, to perform a scan of an ROI of a subject using an imaging device such as a CT device or an MR device, it is desirable to perform a pre-scan to acquire a positioning image, and a user (e.g., a doctor, a technician) needs to manually adjust the positioning of a target area relating to the subject according to the positioning image in order to place the ROI of the subject within the target area. In some embodiments, there is no suitable anatomical image to visualize and assist the user to determine the protocol; a protocol editor which is widely used in scanning needs a user to input table positions and/or reconstruction parameters (e.g., a center X, a center Y, an FOV, etc.) of a protocol manually based on experience and estimations. The user may need to perform more adjustments due to e.g., variations among subjects, which may reduce the efficiency of the imaging process.

Therefore, it is desired to provide systems and methods for automating and/or assisting the determination and/or positioning of an ROI of the subject for a medical process, thereby improving the efficiency and/or accuracy of the positioning operation in the medical process, which in turn may improve the efficiency and/or efficacy of the medical process.

SUMMARY

In an aspect of the present disclosure, a method for positioning a table in a medical device is provided. The table may have a long direction. The method may be implemented on at least one machine, each of which has at least one processor and at least one storage device. The method may include obtaining a target image including a subject situated on the table. The method may include obtaining, in the target image, a focus position. The focus position may be associated with an ROI of the subject to be scanned or treated by the medical device. The method may also include determining, based on the focus position, a target table position. When the table is at the target table position, the ROI of the subject is located at or in a vicinity of an isocenter of the medical device.

In some embodiments, to obtain, in the target image, a focus position, the method may include obtaining a protocol associated with the ROI. The method may also include determining the focus position based on the protocol.

In some embodiments, the method may further include causing the target image to be displayed with a movable line on a terminal device. The movable line may be vertical to the long direction of the table in the target image. To obtain, in the target image, a focus position, the method may include receiving a user instruction with respect to moving the movable line in the target image. The method may also include determining the focus position based on the movable line moved according to the user instruction.

In some embodiments, the target image may include a mark on the subject, and the obtaining, in the target image, a focus position may include determining the focus position based on the mark.

In some embodiments, the method may further include determining the mark by a process. The process may include projecting a positioning image associated with the ROI on the subject according to which the mark on the subject is determined.

In some embodiments, to project a positioning image associated with the region of interest on the subject, the method may include projecting the positioning image according to preliminary projection parameters on the subject. The preliminary parameters may include a projection size or a projection location. The method may include obtaining a first image including the subject and the projected positioning image.

The method may include determining adjusted projection parameters by adjusting, based on the first image, the preliminary projection parameters. The method may also include projecting the positioning image according to the adjusted projection parameters on the subject such that the positioning image aligns with the subject In some embodiments, to determine, based on the focus position, a target table position, the method may include obtaining a mapping relation between a physical length of the table and a virtual length of the table in the target image. The method may also include obtaining, in the target image, a reference position of the table. The method may also include determining, in the target image, a reference distance based on the focus position and the reference position. The method may also include determining the target table position based on the reference distance and the mapping relation.

In another aspect of the present disclosure, a system for positioning a table in a medical device is provided. The table may have a long direction. The system may include at least one storage device including a set of instructions, and at least one processor configured to communicate with the at least one storage device. When executing the set of instructions, the at least one processor may be configured to cause the system to perform the following operations. The system may obtain a target image including a subject situated on the table. The system may obtain, in the target image, a focus position. The focus position may be associated with an ROI of the subject to be scanned or treated by the medical device. The system may also determine, based on the focus position, a target table position. When the table is at the target table position, the ROI of the subject may be located at or in a vicinity of an isocenter of the medical device.

In another aspect of the present disclosure, a system for positioning a table in a medical device is provided. The table may have a long direction. The system may include an image acquisition device, an image processing module, and a control module. The image acquisition module may be configured to obtain a target image including a subject situated on the table. The image processing module may be configured to obtain, in the target image, a focus position. The focus position may be associated with an ROI of the subject to be scanned or treated by the medical device. The control module may be configured to determine, based on the focus position, a target table position. When the table is at the target table position, the ROI of the subject may be located at or in a vicinity of an isocenter of the medical device.

In another aspect of the present disclosure, a non-transitory computer readable medium storing instructions for positioning a table in a medical device is provided. The table may have a long direction. When executed by at least one processor, the instructions may cause the at least one processor to implement a method. The method may include obtaining a target image including a subject situated on the table. The method may include obtaining, in the target image, a focus position. The focus position may be associated with an ROI of the subject to be scanned or treated by the medical device. The method may also include determining, based on the focus position, a target table position. When the table is at the target table position, the ROI of the subject may be located at or in a vicinity of an isocenter of the medical device.

In another aspect of the present disclosure, a method is provided. The method may be implemented on at least one machine, each of which has at least one processor and at least one storage device. The method may include projecting, by a projector, a positioning image on a subject situated on a table of a medical device, according to which a mark on the subject that indicates an ROI of the subject is determined. The method may include obtaining, by an image acquisition device, a target image including the subject and the mark on the subject. The method may also include determining, in the target image, a focus position based on the mark. The focus position may be associated with the ROI in the target image.

In some embodiments, to project a positioning image on the subject, the method may include projecting the positioning image according to preliminary projection parameters on the subject. The preliminary parameters may include a projection size or a projection location. The method may include obtaining a first image including the subject and the projected positioning image. The method may include determining adjusted projection parameters by adjusting, based on the first image the preliminary projection parameters. The method may also include projecting the positioning image according to the adjusted projection parameters on the subject such that the positioning image aligns with the subject.

In some embodiments, the positioning image may include more than one ROI.

To project, by a projector, a positioning image on the subject, the method may include determining more than one segment each of which corresponds to one of the more than one ROI by segmenting the positioning image. The method may also include projecting the more than one segment of the positioning image on the subject. At least two of the more than one segment may be projected in different colors.

In some embodiments, the mark may include a box or a line. The determining, in the target image, the focus position based on the mark may include determining, in the target image, a position of a centerline of the box as the focus position, or determining, in the target image, a position of the line as the focus position.

In some embodiments, to project, by a projector, a positioning image on the subject, the method may include projecting an interface of the medical device on the table. The method may include obtaining a second image including a user gesture directed to the projected interface. The method may include analyzing the user gesture in the second image to obtain an analysis result. The method may also include projecting the positioning image on the subject based on the analysis result.

In some embodiments, the interface of the medical device may include a selection of at least one of the positioning image, information of the subject, a scan protocol, a go-back operation, or a forward operation.

In some embodiments, the user gesture may include covering a portion of the projected interface by a part of the user or an object to indicate a selection of the positioning image.

In some embodiments, the method may further include determining, based on the focus position, a target table position. When the table is positioned at the target table position, the ROI of the subject is located at or in a vicinity of an isocenter of the medical device.

In some embodiments, the projector may be mounted above the table.

In another aspect of the present disclosure, a system is provided. The system may include at least one storage device including a set of instructions, and at least one processor configured to communicate with the at least one storage device. When executing the set of instructions, the at least one processor may be configured to cause the system to perform the following operations. The system may project, by a projector, a positioning image on a subject situated on a table of a medical device, according to which a mark on the subject that indicates an ROI of the subject is determined. The system may obtain, by an image acquisition device, a target image including the subject and the mark on the subject. The system may also determine, in the target image, a focus position based on the mark, the focus position may be associated with the ROI in the target image.

In another aspect of the present disclosure, a system is provided. The system may include a projector, an image acquisition module, an image processing module, and a control module. The projector may be configured to project a positioning image on a subject situated on a table of a medical device, according to which a mark on the subject that indicates an ROI of the subject is determined. The image acquisition device may be configured to obtain a target image including the subject and the mark on the subject. The image processing module may be configured to determine, in the target image, a focus position based on the mark. The focus position may be associated with the ROI in the target image. The control module may be configured to determine, based on the focus position, a target table position, wherein when the table is at the target table position, the region of interest of the subject is located at or in a vicinity of an isocenter of the medical device. The control module may also be configured to cause the table to move to the target table position.

In another aspect of the present disclosure, a non-transitory computer readable medium storing instructions is provided. When executed by at least one processor, the instructions may cause the at least one processor to implement a method. The method may include projecting, by a projector, a positioning image on a subject situated on a table of a medical device, according to which a mark on the subject that indicates an ROI of the subject is determined. The method may include obtaining, by an image acquisition device, a target image including the subject and the mark on the subject. The method may include determining, in the target image, a focus position based on the mark. The focus position may be associated with the ROI in the target image.

In another aspect of the present disclosure, a method is provided. The method may be implemented on at least one machine, each of which has at least one processor and at least one storage device. The method may include obtaining a model image corresponding to a subject. The method may include obtaining a virtual area in the model image. The virtual area may correspond to a virtual ROI. The method may include obtaining a positioning image of the subject. The method may also include determining, based on the virtual area and the positioning image, a target area in the positioning image. The target area may correspond to an ROI of the subject corresponding to the virtual ROI.

In some embodiments, to determine, based on the virtual area and the positioning image, the target area in the positioning image, the method may include determining, in the positioning image, the ROI of the subject based on the virtual ROI. The method may also include determining the target area in the positioning image based on the ROI.

In some embodiments, to determine the ROI in the positioning image based on the virtual ROI, the method may include identifying a first feature relating to the virtual ROI in the model image. The method may include identifying a second feature in the positioning image. A degree of similarity between the first feature and the second feature may exceed a predetermined threshold. The method may also include determining, based on the second feature, the ROI in the positioning image.

In some embodiments, to obtain a virtual area in the model image, the method may include obtaining a protocol associated with the ROI of the subject. The method may include determining the virtual ROI in the model image based on the protocol and a first relation between the virtual ROI and the protocol. The method may include obtaining an automated positioning model based on the virtual ROI and a second relation between the virtual ROI and the automated positioning model. The method may also include determining the virtual area corresponding to the virtual ROI based on the automated positioning model.

In some embodiments, to obtain a virtual area in the model image, the method may include obtaining a protocol associated with the ROI of the subject. The method may also include determining the virtual area based on the protocol and a protocol-virtual area relationship.

In some embodiments, the protocol-virtual area relationship may be determined by a process. The process may include obtaining a model image. The process may include determining, in the model image, a virtual positioning area and a virtual clinical area according to a user instruction relating to a virtual ROI in the model image. The process may include determining, based on the virtual positioning area and the virtual clinical area, corresponding protocols. The process may also include generating the protocol-virtual area relationship by correlating the corresponding protocols, the virtual positioning area, and the virtual clinical area.

In some embodiments, the virtual area or the target area may be of a rectangular shape.

In another aspect of the present disclosure, a system is provided. The system may include at least one storage device including a set of instructions, and at least one processor configured to communicate with the at least one storage device. When executing the set of instructions, the at least one processor may be configured to cause the system to perform the following operations. The system may obtain a model image corresponding to a subject. The system may obtain a virtual area in the model image. The virtual area may correspond to a virtual ROI. The system may obtain a positioning image of the subject. The system may also determine, based on the virtual area and the positioning image, a target area in the positioning image. The target area may correspond to an ROI of the subject corresponding to the virtual ROI.

In another aspect of the present disclosure, a non-transitory computer readable medium storing instructions is provided. When executed by at least one processor, the instructions may cause the at least one processor to implement a method. The method may include obtaining a model image corresponding to a subject. The method may include obtaining a virtual area in the model image. The virtual area corresponding to a virtual ROI. The method may include obtaining a positioning image of the subject. The method may include determining, based on the virtual area and the positioning image, a target area in the positioning image. The target area may correspond to an ROI of the subject corresponding to the virtual ROI.

In another aspect of the present disclosure, a method is provided. The method may be implemented on at least one machine each of which has at least one processor and at least one storage. The method may include obtaining a model image relating to a virtual subject. The method may include determining, in the model image, a virtual positioning area and a virtual clinical area according to a user instruction relating to a virtual ROI in the model image. The method may include determining, based on the virtual positioning area and the virtual clinical area, corresponding protocols. The method may also include generating a protocol-virtual area relationship by correlating the corresponding protocols, the virtual positioning area, and the virtual clinical area.

In some embodiments, the corresponding protocols may include a positioning protocol and a clinical protocol. The positioning protocol may include at least a positioning area in the virtual subject corresponding to the virtual positioning area in the model image. The clinical protocol may include at least a clinical area in the virtual subject corresponding to the virtual clinical area in the model image.

In some embodiments, to determine, based on the virtual positioning area and the virtual clinical area, corresponding protocols, the method may include obtaining a virtual positioning posture of the virtual subject. The method may include determining, based on the virtual positioning posture, a reference table position corresponding to the model image. The method may include determining the positioning area based on the reference table position and the virtual positioning area. The method may also include determining the clinical area based on the reference table position and the virtual clinical area.

In some embodiments, the method may further include determining, in the model image, a first virtual clinical area relating to a first virtual ROI and a second virtual clinical area relating to a second virtual ROI according to a second user instruction. The first virtual ROI and the second virtual ROI may be non-overlapping in the model image. The method may include determining, based on the first virtual clinical area, a first clinical protocol. The method may include determining, based on the second virtual clinical area, a second clinical protocol. The method may also include determining, based on the first clinical protocol and the second clinical protocol, a spatial relationship between the first virtual ROI and the second virtual ROI.

In some embodiments, to generate the protocol-virtual area relationship by correlating the corresponding protocols, the virtual positioning area and the virtual clinical area, the method may include determining a positioning protocol-virtual positioning area relationship based on the positioning protocol and the virtual positioning area. The method may include determining a clinical protocol-virtual clinical area relationship based on the clinical protocol and the virtual clinical area. The method may also include generating the protocol-virtual area relationship based on the positioning protocol-virtual positioning area relationship and the clinical protocol-virtual clinical area relationship.

In some embodiments, the virtual positioning area and the virtual clinical area may correspond to the virtual ROI in the model image.

In some embodiments, the virtual ROI may include at least two virtual sub-ROIs each of which corresponds to a virtual clinical sub-area. The virtual clinical sub-areas may collectively form the virtual clinical area. To determine, based on the virtual positioning area and the virtual clinical area, corresponding protocols, the method may include obtaining a positioning protocol based on the virtual positioning area that corresponds to the virtual ROI in the model image. The method may also include obtaining clinical protocols each of which corresponds to one of the virtual clinical sub-areas.

In some embodiments, at least two of the at least two virtual sub-ROIs may be next to each other.

In another aspect of the present disclosure, a system is provided. The system may include at least one storage device including a set of instructions and at least one processor configured to communicate with the at least one storage device. When executing the set of instructions, the at least one processor may be configured to cause the system to perform the following operations. The system may obtain a model image relating to a virtual subject. The system may determine, in the model image, a virtual positioning area and a virtual clinical area according to a user instruction relating to a virtual ROI in the model image. The system may determine, based on the virtual positioning area and the virtual clinical area, corresponding protocols. The system may also generate a protocol-virtual area relationship by correlating the corresponding protocols, the virtual positioning area, and the virtual clinical area.

In another aspect of the present disclosure, a non-transitory computer readable medium storing instructions is provided. When executed by at least one processor, the instructions may cause the at least one processor to implement a method. The method may include obtaining a model image relating to a virtual subject. The method may include determining, in the model image, a virtual positioning area and a virtual clinical area according to a user instruction relating to a virtual ROI in the model image. The method may include determining, based on the virtual positioning area and the virtual clinical area, corresponding protocols. The method may also include generating a protocol-virtual area relationship by correlating the corresponding protocols, the virtual positioning area, and the virtual clinical area.

In another aspect of the present disclosure, a method for determining a target area relating to a subject situated on a table of a medical system is provided. The medical system may include a first device of a first modality and a second device of a second modality. The method may be implemented on at least one machine, each of which has at least one processor and at least one storage device. The method may include identifying a second target area relating to the subject for performing a second operation using the second device. The method may include determining, based on the second target area, an initial target area relating to the subject for performing a first operation using the first device. The method may also include determining a first target area relating to the subject for performing the first operation using the first device by adjusting the initial target area.

In some embodiments, the second target area may be characterized by at least one parameter including a center position of the second target area, a centerline of the second target area, an orientation of the second target area, or an angle of the second target area with respect to a surface of the table.

In some embodiments, to adjust the initial target area, the method may include identifying an ROI of the subject associated with the first operation using the first device. The method may also include adjusting the initial target area based on the ROI.

In some embodiments, the adjusting the initial target area based on the ROI may include adjusting, based on the ROI, a center position of the initial target area, a centerline of the initial target area, an orientation of the initial target area, an angle of the initial target area with respect to a surface of the table, a boundary of the initial target area, or a size of the initial target area.

In some embodiments, to identify a second target area relating to the subject for performing a second operation using the second device, the method may include obtaining a model image corresponding to the subject. The method may include determining in the model image a virtual area corresponding to the second target area. The method may include determining, based on the virtual area and the positioning image, the second target area relating to the subject.

In some embodiments, at least one of the first device or the second device may be an imaging device or a treatment device.

In some embodiments, the first device and the second device may be imaging devices. The method may further include acquiring first image data by performing the first operation using the first device. The method may include acquiring second image data by performing the second operation using the second device. The method may also include displaying a fusion image based on the first image data and the second image data.

In some embodiments, the first operation and the second operation may be performed synchronously.

In another aspect of the present disclosure, a system for determining a target area relating to a subject situated on a table of a medical system is provided. The medical system may include a first device of a first modality and a second device of a second modality. The system may include at least one storage device including a set of instructions, and at least one processor configured to communicate with the at least one storage device. When executing the set of instructions, the at least one processor may be configured to cause the system to perform the following operations. The system may identify a second target area relating to the subject for performing a second operation using the second device. The system may determine, based on the second target area, an initial target area relating to the subject for performing a first operation using the first device. The system may also determine a first target area relating to the subject for performing the first operation using the first device by adjusting the initial target area.

In another aspect of the present disclosure, a non-transitory computer readable medium storing instructions for determining a target area relating to a subject situated on a table of a medical system is provided. The medical system may include a first device of a first modality and a second device of a second modality. When executed by at least one processor, the instructions may cause the at least one processor to implement a method. The method may include identifying a second target area relating to the subject for performing a second operation using the second device. The method may include determining, based on the second target area, an initial target area relating to the subject for performing a first operation using the first device. The method may also include determining a first target area relating to the subject for performing the first operation using the first device by adjusting the initial target area.

In another aspect of the present disclosure, a system is provided. The system may include an acquisition module, a virtual area determination module, and a target area determination module. The acquisition module configured to obtain a model image corresponding to a subject. The acquisition module may also be configured to obtain a positioning image of the subject. The virtual area determination module may be configured to obtain a virtual area in the model image, the virtual area corresponding to a virtual ROI. The target area determination module may be configured to determine, based on the virtual area and the positioning image, a target area in the positioning image. The target area corresponding to an ROI of the subject corresponding to the virtual ROI.

In some embodiments, the system may further include a protocol determination module configured to obtain a protocol associated with the ROI of the subject. The virtual ROI in the model image may be determined based on the protocol.

In another aspect of the present disclosure, a system is provided. The system may include an acquisition module, a virtual area determination module, a protocol determination module, and a relation determination module. The acquisition module may be configured to obtain a model image relating to a virtual subject. The virtual area determination module may be configured to determine, in the model image, a virtual positioning area and a virtual clinical area according to a user instruction relating to a virtual region of interest in the model image. The protocol determination module may be configured to determine, based on the virtual positioning area and the virtual clinical area, corresponding protocols. The relation determination module may be configured to generate a protocol-virtual area relationship by correlating the corresponding protocols, the virtual positioning area, and the virtual clinical area.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
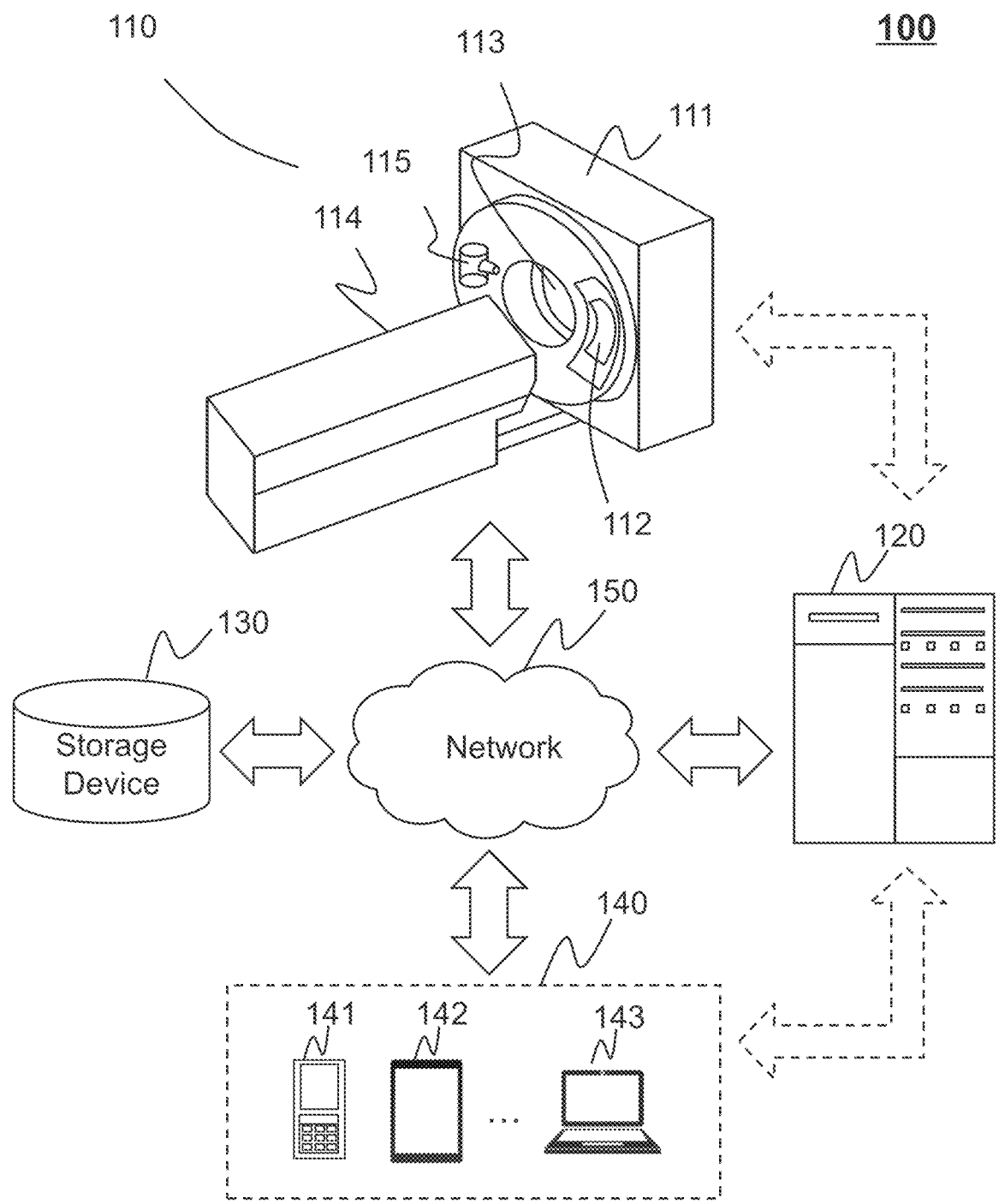
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc.

As used herein, the term "region of interest (ROI)" refers to a region in a subject (e.g., a tissue, an organ, a lesion of the subject to be imaged and/or treated), or a corresponding region in an image of the subject. As used herein, the term "target area relating to a subject," or "target area" for brevity, refers to an area including an ROI of a subject or a corresponding area in an image of the subject based on which a medical device is directed to scan and/or treat the ROI of the subject within the area. As used herein, the term "virtual ROI" refers to a portion of a model image including a representation of a specific portion corresponding to an ROI of the subject.

As used herein, a representation of an object (e.g., a patient, a subject, or a portion thereof) in an image may be referred to the object for brevity. For instance, a representation of an organ or tissue (e.g., the heart, the liver, a lung, etc., of a patient) in an image may be referred to as the organ or tissue for brevity. An image including a representation of an object may be referred to as an image of the object or an image including the object for brevity. As used herein, an operation on a representation of an object in an image may be referred to as an operation on the object for brevity. For instance, a segmentation of a portion of an image including a representation of an organ or tissue (e.g., the heart, the liver, a lung, etc., of a patient) from the image may be referred to as a segmentation of the organ or tissue for brevity.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging/treatment, such as for disease diagnostic, disease therapy, or research purposes. In some embodiments, the systems may include a single modality system and/or a multi-modality system. The single modality system may include, for example, may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. It should be noted that the medical system described below is merely provided for illustration purposes, and not intended to limit the scope of the present disclosure.

The term "modality" as used herein broadly refers to an imaging or treatment method or technology that gathers, generates, processes, and/or analyzes imaging information of a subject or treatments the subject. The subject may include a biological object and/or a non-biological object. The biological subject may be a human being, an animal, a plant, or a portion thereof (e.g., a cell, a tissue, an organ, etc.). In some embodiments, the subject may be a man-made composition of organic and/or inorganic matters that are with or without life. The term "object" or "subject" are used interchangeably in the present disclosure.

An aspect of the present disclosure relates to systems and methods for positioning a table in a medical device. The system may obtain a target image including a subject situated on the table. The system may obtain, in the target image, a focus position. The focus position may be associated with a region of interest (ROI) of the subject to be scanned or treated by the medical device. The system may determine, based on the focus position, a target table position. When the table is at the target table position, the ROI of the subject may be located at or in the vicinity of an isocenter of the medical device. According to the systems and/or methods disclosed herein, a target table position may be determined automatically by adding an image acquisition device and/or a projector in a medical system. In some embodiments, based on the image acquisition device, a target image including the subject situated on the table may be obtained. The target image may be displayed with an identifier (e.g., a movable line). The position and/or range of the ROI of the subject may be determined based on the target image and the identifier. In some embodiments, using the projector, a positioning image may be projected on the subject. A position and/or area of the ROI of the subject may be determined by drawing a mark on the subject based on the positioning image. The target table position may be determined based on the position and/or range of the ROI. In some embodiments, the inclusion of the image acquisition device and/or the projector in the medical system may also facilitate and/or enhance the interaction between the user and the subject during a medical process. One or more of various visualization and/or communication techniques may be used to facilitate the positioning of the subject, reduce the amount of information that needs to be provided by a user, and/or reduce the reliance on user experience and cross-user variance, thereby improving the efficiency and/or accuracy of the medical system (e.g., an imaging and/or treatment system)

Another aspect of the present disclosure relates to systems and methods for determining a target area relating to a subject in a medical device. The system may obtain a model image corresponding to a subject. The system may obtain a virtual area in the model image. The virtual area may correspond to a virtual ROI. The system may also obtain a positioning image of the subject. The system may determine a target area in the positioning image based on the virtual area and the positioning image. The target area may correspond to an ROI of the subject corresponding to the virtual ROI. According to the systems and/or methods disclosed herein, a target area relating to an ROI of a subject may be determined automatically based on a model image and a positioning image. In some embodiments, a virtual ROI corresponding to the ROI may be identified in the model image for determining the ROI in the positioning image. A target area may be determined based on the ROI identified in the positioning image. In some embodiments, a protocol associated with the ROI of the subject and/or a protocol-virtual area relationship may be determined using the model image. The model image may provide a visual guidance for the user to determine the protocol associated with the ROI and/or the protocol-virtual area relationship. One or more of various visualization and/or communication techniques may be used to facilitate the positioning of the subject, reduce the amount of information that needs to be provided by a user, and/or reduce the reliance on user experience and cross-user variance, thereby improving the efficiency and/or accuracy of the medical system (e.g., an imaging and/or treatment system).

Another aspect of the present disclosure relates to systems and methods for determining a first target area relating to a subject based on a second target area relating to the subject. The first target area relating to the subject may be involved in performing a first operation using a first device of a first modality (or referred to as a first device or a first-modality device for brevity). The second target area relating to the subject may be involved in performing a second operation using a second device of a second modality (or referred to as a second device or a second-modality device for brevity). The system may determine, based on the second target area, an initial target area relating to the subject for performing a first operation using the first device. The system may determine the first target area relating to the subject for performing the first operation using the first device by adjusting the initial target area. According to some embodiments of the systems and/or methods as described herein, a first target area relating to a subject for a first imaging/treatment operation using the first-modality device may be determined based on a second target area relating to the subject for a second imaging/treatment operation in a second-modality device. In some embodiments, an initial target area may be set in concert with the second target area.

An ROI of the subject to be imaged/treated by the first-modality device may be identified, e.g., in a positioning image of the subject. The first target area may be determined by adjusting the initial target area based on the identified ROI (e.g., adjusting a center position, a centerline, an angle, etc. of the initial target area) such that the entire ROI may be within the first target area. Therefore, for a particular table position, the first-modality device may perform the first imaging/treatment operation on the subject based on the first target area, and the second-modality device may perform the second imagining/treatment operation on the subject based on the second target area. For the first-modality device and the second-modality device being imaging devices, the first imaging operation and the second imagining operation may be performed synchronously. Images acquired by the first-modality device and the second-modality device may be fused for display, which improves the efficiency and/or accuracy of a medical system (e.g., a multi-modality system).

FIG. 1 is a schematic diagram illustrating an exemplary medical system according to some embodiments of the present disclosure. In some embodiments, the medical system may be applied to any application in which a subject is scanned for generating images, and/or uses a variety of energies (e.g., force, heat, light, electricity, sound, magnetism, radiation, etc.) to act on the subject for providing treatment (e.g., removing unwanted tissue, or keeping physiological parameters stable of the subject), such as a single modality system or a multi-modality system. Exemplary single modality system may include a computed tomography (CT) system, a magnetic resonance (MR) system, a digital radiography (DR) system, a positron emission tomography (PET) system, an endoscope system, a radiotherapy (RT) device, a nuclear medical treatment device, a surgical robot, a laser device, a radio frequency (RF) device, an electronic pulse device, or the like. Exemplary multi-modality system may include a positron emission tomography-magnetic resonance (PET-MR) system, a C-arm X-ray system, a computed tomography-positron emission tomography (CT-PET) system, an image-guided radiotherapy (IGRT) system (e.g., a CT guided radiotherapy system), a computed tomography-radiotherapy (CT-RT), or the like, or any combination thereof. For illustration purposes, the medical system illustrated in FIG. 1 may be a medical system 100.

As illustrated in FIG. 1, the medical system may include a medical device 110, a processing device 120A, a storage device 130, one or more terminal devices 140, and a network 150. The components in the medical system may be connected in one or more of various ways. Merely by way of example, the medical device 110 may be connected to the processing device 120 through the network 150. As another example, the medical device 110 may be connected to the processing device 120 directly as indicated by the bi-directional arrow in dotted lines linking the medical device 110 and the processing device 120. As a further example, the storage device 130 may be connected to the processing device 120 directly or through the network 150. As still a further example, the terminal device 140 may be connected to the processing device 120 directly (as indicated by the bi-directional arrow in dotted lines linking the terminal device 140 and the processing device 120) or through the network 150.

The medical device 110 may be configured to acquire imaging data relating to at least one part of a subject. The medical device 110 may scan the subject or a portion thereof that is located within its detection region and generate imaging data relating to the subject or the portion thereof. The imaging data relating to at least one part of a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made object, etc.

As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof. In some embodiments, the medical device 110 may include a single modality imaging device. For example, the medical device 110 may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device, an ultrasonography scanner, a digital radiography (DR) scanner, or the like, or any combination thereof. In some embodiments, the medical device 110 may include a multi-modality imaging device. Exemplary multi-modality imaging devices may include a PET-CT device, a PET-MR device, or the like, or a combination thereof.

The medical device 110 may include a gantry 111, one or more detectors 112, a detecting region 113, a table 114, a radiation source 115, or any other component. The gantry 111 may be configured to provide support for other components (e.g., the radiation source 115, the detector(s) 112, etc.) of the medical device 110. In some embodiments, the detector(s) 112 and the radiation source 115 may be oppositely mounted on the gantry 111. In some embodiments, the gantry 111 may rotate and/or move. The detector(s) 112 and the radiation source 115 may rotate along with the rotation of the gantry 111. The table 114 may be configured to locate and/or support a scanned subject. A scanned subject may be placed on the table 114 and moved into the detecting region 113 (e.g., a space between the detector(s) 112 and the radiation source 115) of the medical device 110.

The processing device 120 may process data and/or information obtained from the medical device 110, the terminal device(s) 140, and/or the storage device 130. For example, according to an identifier in a target image including a representation of a subject situated on a table, the processing device 120 may determine a target table position associated with an ROI of the subject to be scanned or treated by the medical device. As another example, according to a model image corresponding to a subject, the processing device 120 may determine a target area relating to the subject associated with the ROI of the subject. The target area may be a scan area and/or a treatment area that includes the ROI of the subject. As still another example, the processing device 120 may determine a protocol-virtual area relationship based on a model image relating to a virtual subject. As still a further example, in a multi-modality system including a first device of a first modality and a second device of a second modality the processing device 120 may determine a first target area relating to the subject in the first device based on a second target area relating to the subject in the second device. The processing device 120 may be a central processing unit (CPU), a digital signal processor (DSP), a system on a chip (SoC), a microcontroller unit (MCU), or the like, or any combination thereof.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal device(s) 140, and/or the storage device 130 via the network 150. As another example, the processing device 120 may be directly connected to the medical device 110, the terminal device(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components as described in FIG. 2.

The storage device 130 may store data, instructions, and/or any other information. In some embodiments, the storage device 130 may store data obtained from the medical device 110, the terminal device(s) 140 and/or the processing device 120. In some embodiments, the storage device 130 may store data and/or instructions that the processing device 120 may execute or use to perform exemplary methods/systems described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the storage device 130 may include a Picture Archiving and Communication Systems (PACS) in a hospital.

In some embodiments, the storage device 130 may be connected to the network 150 to communicate with one or more other components (e.g., the processing device 120A, the terminal device(s) 140, etc.) in the medical system. One or more components in the medical system may access the data or instructions stored in the storage device 130 via the network 150. In some embodiments, the storage device 130 may be directly connected to or communicate with one or more other components (e.g., the processing device 120A, the terminal device(s) 140, etc.) in the medical system. In some embodiments, the storage device 130 may be part of the processing device 120.

Figure 7:
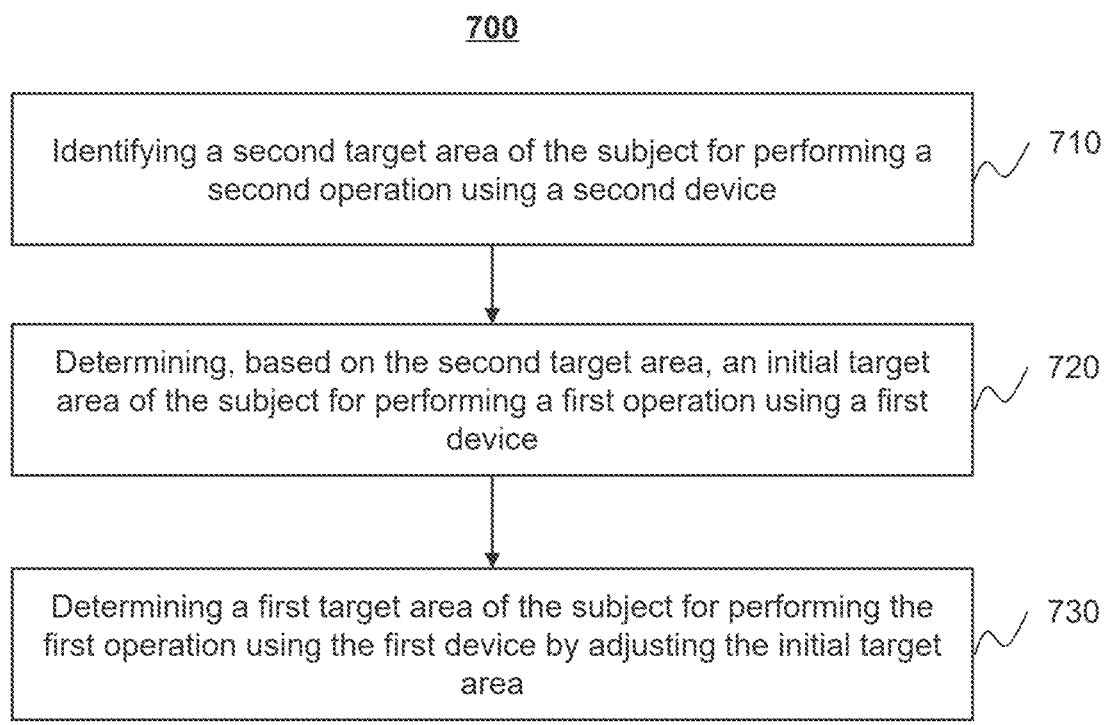
FIG. 7 is a schematic flowchart illustrating an exemplary process for determining a target area relating to a subject situated on a table of a medical device according to some embodiments of the present disclosure.

In some embodiments, a user (e.g., a doctor, a technician, or an operator) may interact with the medical system 100 through the terminal device(s) 140. For example, the user may move an identifier in a target image including a subject situated on a table through the terminal device(s) 140 on the basis of which the processing device 120 may determine a target table position of the table. As another example, one or more selections associated with one or more function (e.g., "MRI Off-Center," "MRI Off-Centerline," "MRI Off-Angle, " "MRI Off-Boundary," "MRI Off-Upper Boundary," "MRI Off-Lower Boundary," "MRI Off-Left Boundary," "MRI Off-Right Boundary," etc.) may be displayed on an interface associated with the terminal device 140. The user may select one or more of the selections by the terminal device 140 on the basis of which the processing device 120 may perform one or more operations as illustrated in FIG. 7. The one or more selections may be displayed when the medical system 100 is in a multi-modality mode, and may be hidden when the medical system 100 is in a single modality mode. The terminal device(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device(s) 140 may be part of the processing device 120.

The network 150 may include any suitable network that can facilitate the exchange of information and/or data for the medical system. In some embodiments, one or more components (e.g., the medical device 110, the processing device 120A, the storage device 130, the terminal device(s) 140, etc.) of the medical system may communicate information and/or data with one or more other components of the medical system via the network 150. For example, the processing device 120 may obtain data from the medical device 110 via the network 150. As another example, the processing device 120 may obtain user instructions from the terminal device(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points, such as base stations and/or internet exchange points, through which one or more components of the medical system may be connected to the network 150 to exchange data and/or information.

In some embodiments, the medical system may further include a proximity sensor (e.g., a radio frequency device) (not shown in FIG. 1). In some embodiments, the proximity sensor may be disposed in the vicinity of an emergency stop button. In some embodiments, the emergency stop button may be disposed on the medical device 110 and/or on the terminal device 140. The proximity sensor may be configured to detect if a user or any other person is within a safe distance from the emergency stop button. The proximity sensor may communicate with one or more other components of the medical system (e.g., the processing device 120A, the storage device 130, the terminal device 140) via the network 150. In some embodiments, if it is determined that no one is within the safe distance when the table 114 is moving caused by, e.g., a drive device, the processing device 120 may cause an alarm device to generate an alarm signal (e.g., an audio alert) to remind a user of the medical system of the situation. Merely by way of example, a person within the safe distance from the emergency stop button can stop the movement of the table 114 if something wrong is to occur or has happened to the medical device 110 and/or a subject to be imaged or treated. In some embodiments, if it is determined that no one is within the safe distance during the movement of the table 114, the processing device 120 may cause the table 114 to stop moving by, e.g., disconnecting the drive device from the table 114.

Figure 2:
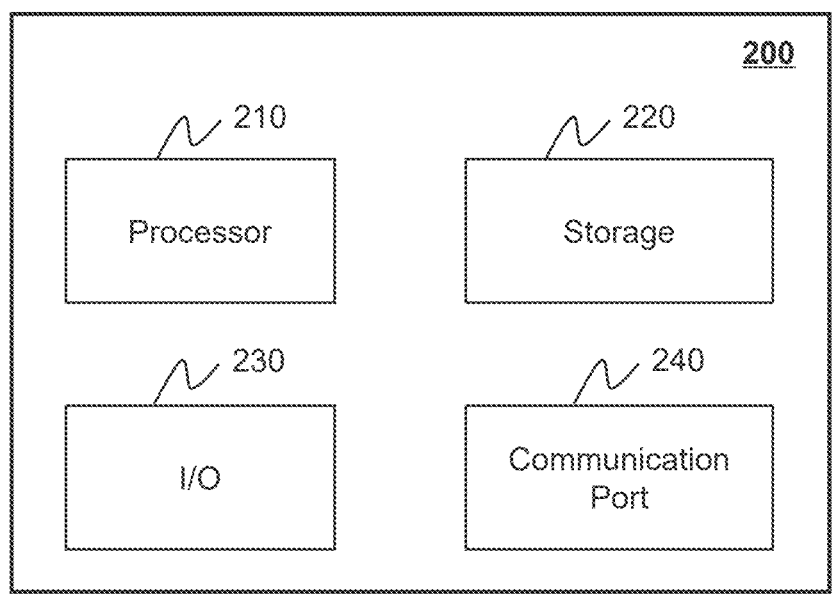
FIG. 2 is a schematic diagram illustrating exemplary hardware and/or software components of an exemplary computing device according to some embodiments of the present disclosure.

It should be noted that the above description of the medical system is merely provided for the purposes of illustration, and not intended to limit the scope of the present disclosure. For persons having ordinary skills in the art, multiple variations and modifications may be made under the teachings of the present disclosure. For example, the assembly and/or function of the medical system may be varied or changed according to specific implementation scenarios. As another example, the medical system 100 may be a system including a radiation device 110. The medical system 100 may be configured to deliver radiation for imaging and/or treatment purposes. The disclosure with reference to the medical device 110 may be an imaging device for illustration purposes and not intended to be limiting. In some embodiments, the medical system 100 may include one or more additional components, and/or one or more components of the medical system may be omitted. For example, the medical system 100 may include an image acquisition device (e.g., a camera) and/or a projector, the description of which may be found elsewhere in the present disclosure (e.g., FIGS. 5-6) and the descriptions FIG. 2 is a schematic diagram illustrating hardware and/or software components of an exemplary computing device 200 may be implemented according to some embodiments of the present disclosure. The computing device 200 may be used to implement any component of the medical system as described herein. For example, the processing device 120 and/or a terminal device 140 may be implemented on the computing device 200, respectively, via its hardware, software program, firmware, or a combination thereof. Although only one such computing device is shown, for convenience, the computer functions relating to the medical system as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal device(s) 140, the storage device 130, or any other component of the medical system. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal device(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
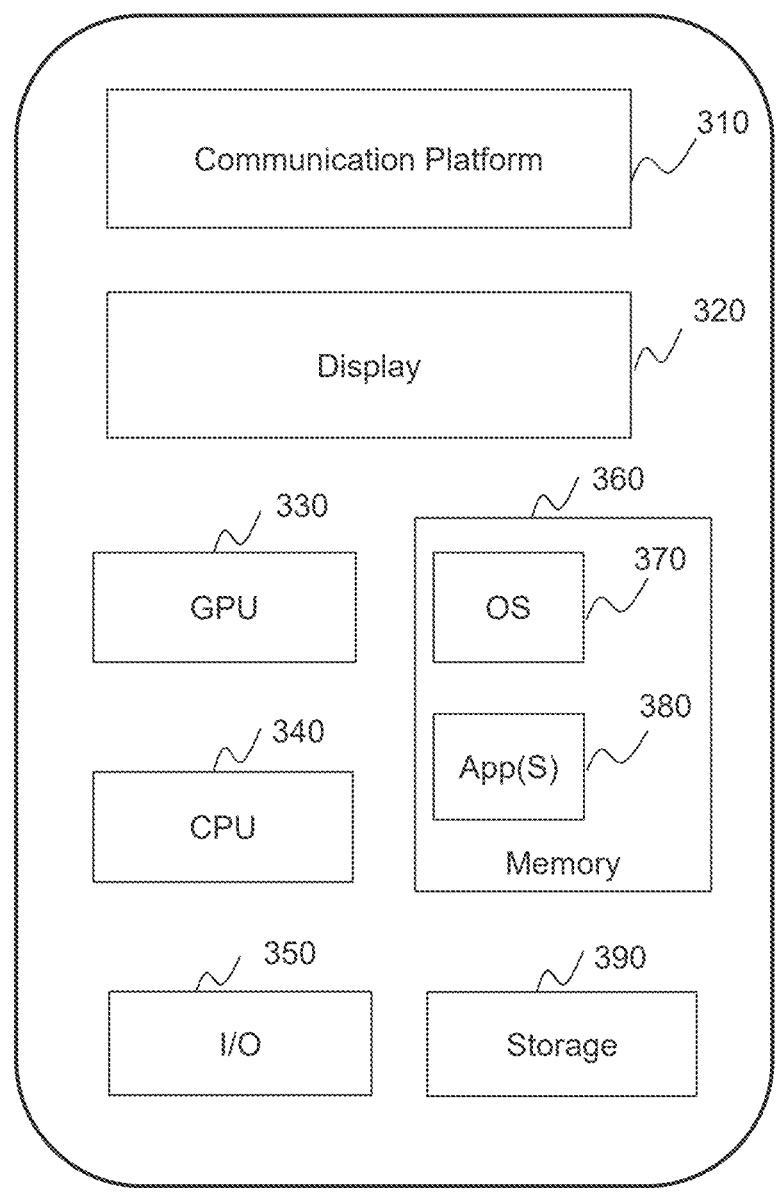
FIG. 3 is a schematic diagram illustrating exemplary hardware and/or software components of an exemplary mobile device according to some embodiments of the present disclosure.

FIG. 3 is a schematic diagram illustrating hardware and/or software components of an exemplary mobile device 300 according to some embodiments of the present disclosure. In some embodiments, one or more components (e.g., a terminal device 140 and/or the processing device 120) of the medical system may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the medical system via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
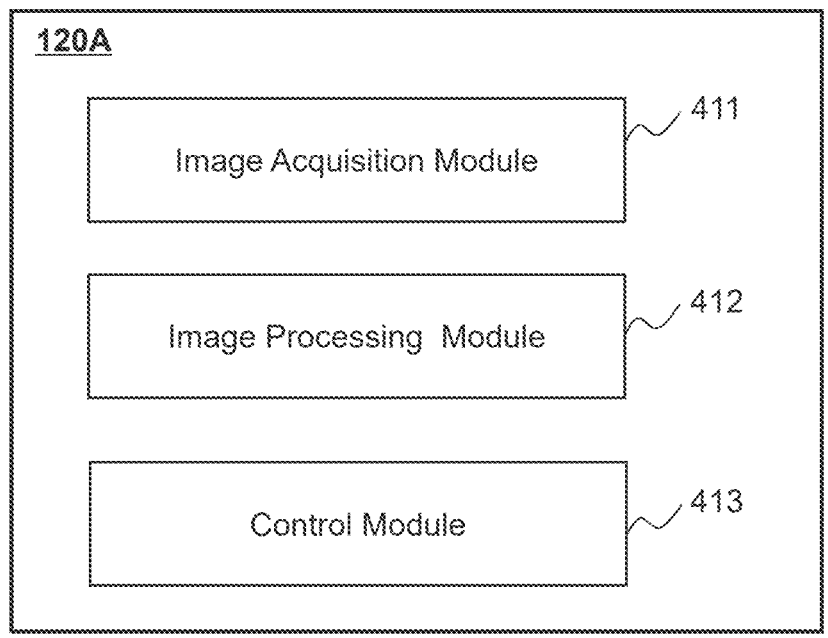
FIG. 4A, FIG. 4B, and FIG. 4C are block diagrams illustrating exemplary processing devices according to some embodiments of the present disclosure.
Figure 4B:
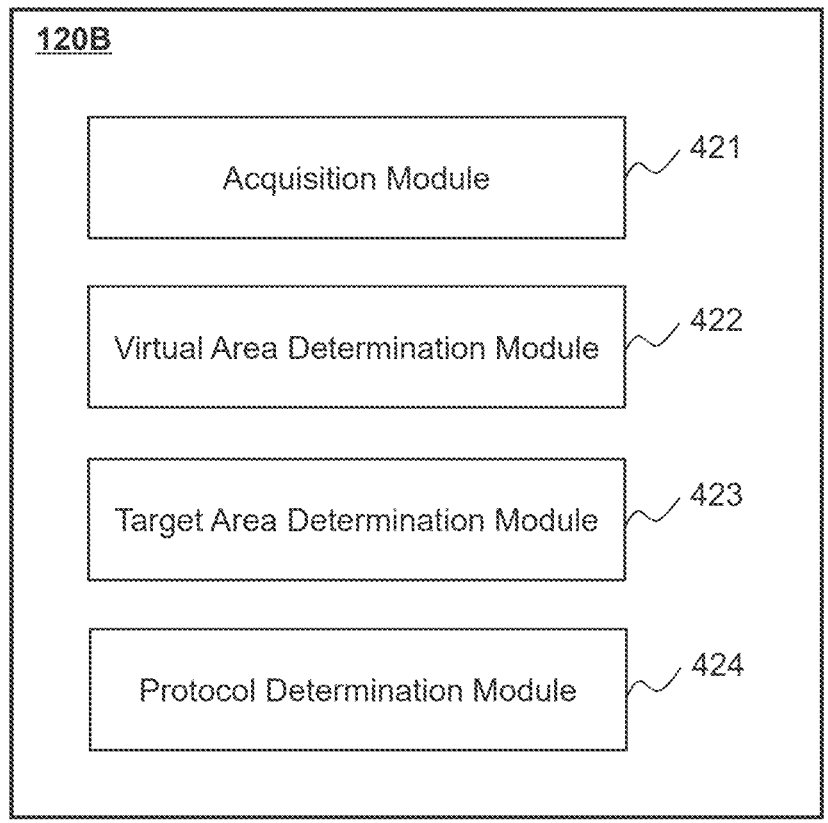
Figure 4C:
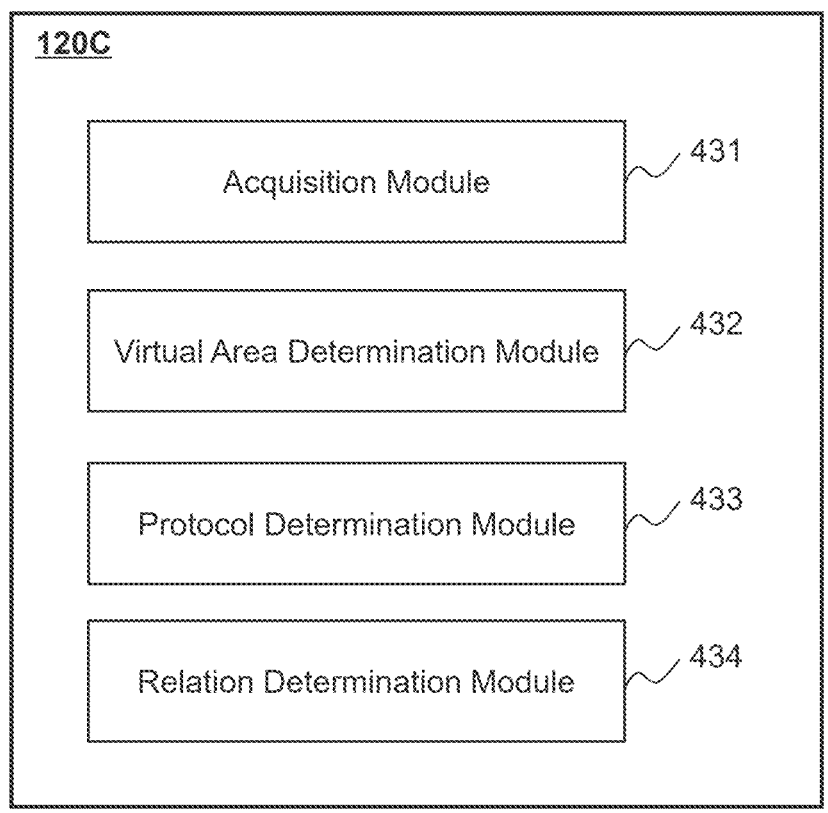

FIG. 4A, FIG. 4B, and FIG. 4C are block diagrams illustrating exemplary processing devices according to some embodiments of the present disclosure. In some embodiments, the processing devices 120A, 120B, and 120C may be embodiments of the processing device 120 as described in connection with FIG. 1. In some embodiments, the processing devices 120A, 120B, and 120C may be respectively implemented on a processing unit (e.g., the processor 210 illustrated in FIG. 2 or the CPU 340 as illustrated in FIG. 3). Merely by way of example, the processing devices 120A may be implemented on a CPU 340 of a terminal device, and the processing device 120B and/or the processing device 120C may be implemented on a computing device 200. Alternatively, the processing devices 120A, 120B, and 120C may be implemented on a same computing device 200 or a same CPU 340. For example, the processing devices 120A, 120B, and 120C may be implemented on a same computing device 200.

As shown in FIG. 4A, the processing device 120A may include an image acquisition module 411, an image processing module 412, and a control module 413.

The image acquisition module 411 may be configured to obtain image data from one or more components of the medical system 100 (e.g., an image acquisition device, the storage device 130, etc.). For example, the image acquisition module 411 may obtain a target image. The target image may include a subject situated on the table and/or a mark on the subject. As another example, the image acquisition module 411 may obtain one or more images including a positioning image projected on the subject. As still another example, the image acquisition module 411 may obtain one or more images including a user posture directed to a projected interface.

The image processing module 412 may be configured to process one or more images. For example, the image processing module 412 may obtain, in the target image, a focus position associated with an ROI of the subject to be scanned or treated by a medical device (e.g., the medical device 110). As another example, the image processing module 412 may determine adjusted projection parameters by analyzing an image including a projected positioning image/or projected interface with preliminary projection parameters. As still another example, the image processing module 412 may determine an analysis result by analyzing one or more user gestures in an image including the one or more user gestures. The user gesture may include covering a selection on the projected interface by a part of the user or an object.

The control module 413 may be configured to control operations of modules or components of the medical system 100. In some embodiments, the control module 413 may cause a table to move to a target table position. When the table is at the target table position, the ROI of the subject may be located at or in the vicinity of an isocenter of the medical device (e.g., the medical device 110). The control module 413 may determine the target table position based on the focus position. More descriptions regarding the determination of the target table position may be found elsewhere in the present disclosure (e.g., FIG. 5 and the descriptions thereof). In some embodiments, the control module 413 may cause the target image to be displayed with an identifier (e.g. a movable line) in the target image. The control module 412 may cause the identifier to move according to a user instruction and/or a protocol for imaging or treatment. In some embodiments, the control module 413 may cause a projector to project the positioning image and/or the interface on the subject according to preset/adjusted projection parameters and/or the analysis result. In some embodiments, the control module 413 may cause an image acquisition device to capture one or more images including the subject situated on the table, the projected positioning image/interface, or the like, or any combination thereof.

As shown in FIG. 4B, the processing device 120B may include an acquisition module 421, a virtual area determination module 422, a target area determination module 423, and a protocol determination module 424.

The acquisition module 421 may be configured to obtain data/information from one or more components of the medical system 100. For example, the acquisition module 421 may obtain a model image corresponding to a subject from the storage device. The model image may include a virtual human body image, a virtual animal image, or any other virtual biological object image according to a type of the subject. The model image may also be obtained based on information of the subject. Merely by way of example, for the subject being a human, the model image corresponding to the subject may include a female body image or a male body image based on a gender of the subject. As another example, the acquisition module 421 may obtain a positioning image including an ROI of the subject to be scanned or treated by a medical device (e.g., the medical device 110) from a storage device (e.g., a storage device such as the storage device 130, storage 220, and/or storage 390). The positioning image may be generated by the medical device, or other medical/optical imaging device. As still another example, the acquisition module 421 may obtain a protocol associated with the ROI of the subject. As still a further example, the acquisition module 421 may obtain one or more relations such as a first relation between a virtual ROI and a protocol, a second relation between the virtual ROI and an automated positioning model, a protocol-virtual area relationship, etc. More descriptions regarding the one or more relations may be found elsewhere in the present disclosure (e.g., FIGS. 12, 15, and 20 and the descriptions thereof).

The virtual area determination module 422 may be configured to determine a virtual area in the model image. The virtual area may be associated with a virtual ROI in the model image corresponding to an ROI of the subject. For example, the virtual area determination module 422 may determine the virtual area based on the protocol, the first relation and the second relation. As another example, the virtual area determination module 422 may determine the virtual area based on the protocol and the protocol-virtual area relationship. More descriptions regarding the determination of the virtual area may be found elsewhere in the present disclosure (e.g., FIGS. 12 and 15 and the descriptions thereof).

The target area determination module 423 may be configured to determine a target area relating to the subject for performing an operation using a medical device (e.g., the medical device 110). In some embodiments, the target area determination module 423 may determine the target area based on the virtual area and the positioning image, which is described in detail in FIG. 12 and the descriptions thereof). In some embodiments, for the medical device being a multi-modality device including a first device of a first device and a second device of a second modality, the target area determination module 423 may determine a first target image for the first device based on a second target image for the second device and an ROI to be scanned or treated by the first device. More descriptions regarding the determination of the first target area and the second target area in the multi-modality device may be found elsewhere in the present disclosure (e.g., FIGS. 7-10 and the descriptions thereof).

The protocol determination module 424 may be configured to determine and/or obtain a protocol described elsewhere in the present disclosure. In some embodiments, the protocol determination 424 may obtain a protocol for the subject. The protocol may be an imagining protocol or a treatment protocol. The protocol may be associated with the ROI of the subject to be imagined or treated. Different ROIs may correspond to different protocols. For example, for the ROI including the head of the subject to be scanned, the protocol may be a scan protocol corresponding to a head scan. As another example, for the ROI including the chest of the subject to be scanned, the protocol may be a scan protocol corresponding to a chest scan.

As shown in FIG. 4C, the processing device 120C may include an acquisition module 431, a virtual area determination module 432, a protocol determination module 433, and a relation determination module 434.

The acquisition module 431 may be configured to obtain data/information associated with determining a protocol-virtual area relationship. Merely by way of example, the acquisition module 431 may obtain a model image relating to a virtual object.

The virtual area determination module 432 may be configured to determine virtual areas in the model image. For example, the virtual area determination module 432 may determine a virtual positioning area in the model image. The virtual positioning area may correspond to an area in the virtual subject where a scan is simulated to obtain a positioning image of the virtual subject. As another example, the processing device 120C may determine one or more virtual clinical areas in the model image. A virtual clinical area may correspond to an area in the virtual subject where an imaging scan or treatment is simulated on the virtual subject. More descriptions regarding the determination of the virtual positioning/clinical area may be found elsewhere in the present disclosure (e.g., FIG. 20 and the description thereof).

The protocol determination module 433 may be configured to determine protocols corresponding to the virtual areas. For example, the protocol determination module 433 may determine a positioning protocol based on the virtual positioning area. The positioning protocol may include correspondence between positioning areas in the virtual subject and virtual positioning areas in the model image. As another example, the protocol determination module 433 may determine a clinical protocol based on the virtual clinical area. The clinical protocol may include correspondence between clinical areas in the virtual subject and virtual clinical areas in the model image. More descriptions regarding the determination of corresponding protocols may be found elsewhere in the present disclosure (e.g., FIGS. 20, 23 and the descriptions thereof).

The relation determination module 434 may be configured to determine a protocol-virtual area relationship. In some embodiments, the relation determination module 434 may generate the protocol-virtual area relationship by correlating the corresponding protocols, the virtual positioning areas, and the virtual clinical areas. For example, the relation determination module 434 may determine a positioning protocol-virtual positioning area relationship based on the positioning protocol and the virtual positioning area. The relation determination module 434 may determine a clinical protocol-virtual clinical area relationship based on the clinical protocol and the virtual clinical area. The relation determination module 434 may generate the protocol-virtual area relationship based on the positioning protocol-virtual positioning area relationship and the clinical protocol-virtual clinical area relationship. More descriptions regarding the determination of the protocol-virtual area relationship may be found elsewhere in the present disclosure (e.g., FIG. 20 and the descriptions thereof). In some embodiments, the relation determination module 434 may be configured to determine a spatial relationship between a first virtual ROI and a second virtual ROI. More descriptions regarding the determination of the spatial relationship may be found elsewhere in the present disclosure (e.g., FIG. 24 and the descriptions thereof). In some embodiments, the relation determination module 434 may be configured to determine the first relation and/or the second relation as described in the present disclosure.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media.

In some embodiments, the processing device 120A, the processing 120B, and/or the processing device 120C may share two or more of the modules, and any one of the modules may be divided into two or more units. For example, the processing device 120A and the processing device 120B may share a same acquisition module (i.e., the image acquisition module 411 and the acquisition module 421 may be a same acquisition module). In some embodiments, the processing device 120A, the processing device 120B, and/or the processing device 120C may include one or more additional modules, such as a storage module (not shown) for storing data. In some embodiments, the processing device 120A and the processing device 120B may be integrated into one processing device 120. As another example, the processing device 120B and the processing device 120C may be integrated into one processing device 120B. In some embodiments, the processing device 120C may be part of a device or system external to the medical system 100. For instance, the processing device 120C may be part of a device or system of the manufacturer of the medical system 100, or a portion thereof (e.g., the medical device 110), or a vendor that maintains the medical system 100, or a portion thereof (e.g., the medical device 110). In some embodiments, the processing devices 120A, 120B, and 120C may be integrated and implemented on a same processing device of the medical system 100.

Figure 5:
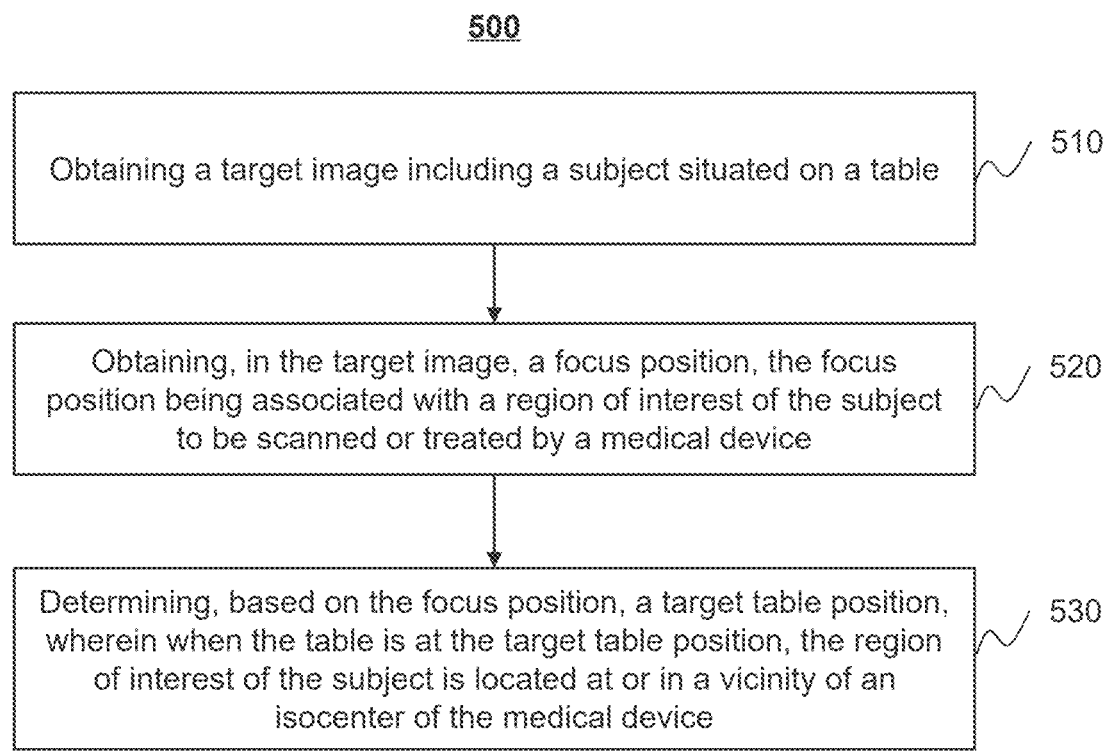
FIG. 5 is a flowchart illustrating an exemplary process for determining a target table position according to some embodiments of the present disclosure.

FIG. 5 is a flowchart illustrating an exemplary process for determining a target table position according to some embodiments of the present disclosure. In some embodiments, the process 500 may be implemented as a set of instructions (e.g., an application) stored in the storage device 130, storage 220, or storage 390. The processing device 120A, the processor 210 and/or the CPU 340 may execute the set of instructions, and when executing the instructions, the processing device 120A, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 510, the processing device 120A (e.g., the image acquisition module 411) may obtain a target image including a subject situated on a table. The subject may be biological or non-biological. For example, the subject may include a patient, a man-made object, etc., as described elsewhere in the present disclosure (e.g., FIG. 1 and the descriptions thereof). The table configured to locate and/or support the subject (e.g., the table 114) may be associated with a medical device (e.g., the medical device 110). The subject may be located at a fixed position on the table. In some embodiments, an actual position of the table may correspond to a table position. The table position may refer to a physical location of the entire table. The physical location of the entire table may be represented by a table code recorded by and/or in the medical device or elsewhere in the medical system 100. The table position may correspond to a virtual line that is vertical to the long direction of the table. As used herein, the long direction of the table refers to the direction along which the table moves into or out of the bore of the medical device 110 where imaging or treatment by the medical device 110 is performed. A table position of the table in which the target image is obtained may also be referred to as a current table position of the table.

In some embodiments, the target image may be a live image captured by an image acquisition device (e.g., a camera) in real-time. The processing device 120A may obtain the target image directly from the camera. The camera may be mounted above the table. For example, the camera may be fixedly mounted on a device (e.g., the shell of the medical device 110) or a wall (e.g., a wall or the ceiling of the room where the medical device 110 is located) such that the camera does not move with respect to where it is mounted. As another example, the camera may be movably mounted on a device or wall such that the camera may move (e.g., in the form of translation, rotation) with respect to where it is mounted. The camera may be configured to obtain image data (e.g., the target image) of an area within the field of view of the camera. As used herein, a camera may refer to an apparatus for visual recording. For example, the camera may include a color camera, a digital video camera, a camera, a camcorder, a PC camera, a webcam, an infrared (IR) video camera, a low-light video camera, a thermal video camera, a Closed Circuit Television (CCTV) camera, a pan/tilt/zoom (PTZ) camera, a video sensing device, or the like, or any combination thereof. In some embodiments, the processing device 120A may obtain the target image from a storage device (e.g., the storage device 130, storage 220, and/or storage 390). For example, the camera may transmit the acquired target image to the storage device for storage and/or future use. The processing device 120A may retrieve the target image from the storage device.

The processing device 120A may transmit the target image to a terminal device (e.g., the terminal device 140) for display. The processing device 120A may cause the target image to be displayed with an identifier on the terminal device. The position of the identifier may correspond to the table position represented in the target image. In some embodiments, the identifier may be a line, a dot, a pin, a box, or the like. In some embodiments, the position of the identifier may be determined based on a centerline or a center point of the identifier. For example, if the identifier is a line vertical to a long direction of the table, a position of a center point of the line in the target image may be determined as the position of the identifier. As another example, if the identifier is a box, a position of a centerline of the box may be determined as the position of the identifier. The identifier may denote a rough location of an area relating to the subject in the target image to be scanned or treated by the medical device 110. For example, if the identifier is a dot, a range in the target image that is within a certain distance from the dot may correspond to the area relating to the subject to be scanned or treated. As another example, if the identifier is a line (e.g., a line with a defined length or not), a range in the target image that is defined by traversing the line by a certain distance in the direction(s) parallel and/or perpendicular to the identifier may correspond to the area relating to the subject to be scanned or treated. As still an example, if the identifier is a box, a range in the target image that is within the box may correspond to the area relating to the subject to be scanned or treated. As still a further example, if the target image of the subject includes one or more portions, the area relating to the subject to be scanned or treated may correspond to an area of a portion of the subject in the target image where the identifier is located.

In some embodiments, the identifier may be displayed at an initial position in the target image randomly or according to a protocol associated with an ROI of the subject to be scanned or treated by the medical device. Merely by way of example, the identifier may include a movable line. The processing device 120A may obtain the protocol associated with the ROI. The processing device 120A may recognize, in the target image, the ROI of the subject based on the protocol. The processing device 120A may cause the movable line to be displayed at the initial position corresponding to a specific position corresponding to the ROI in the target image. In some embodiments, the processing device 120A may determine the specific position of the ROI of the subject in the target image based on characteristics of the subject (e.g., according to an image recognition algorithm such as a threshold based segmentation, a histogram-based algorithm, a pattern recognition algorithm, an image match algorithm, an artificial intelligence (AI) algorithm, an algorithm using a trained recognition model, a template matching algorithm, a target tracking algorithm, a machine learning algorithm, etc.). For example, if the subject is a human, the processing device 120A may segment the human to obtain a plurality of specific regions, such as a head region, a chest region, an abdominal region, an upper limb region, a lower limb region, or the like. The processing device 120A may determine, in the target image, the ROI of the subject among the specific regions, and designate a position in the ROI (e.g., a centerline position of the ROI in the target image) as the specific position of the ROI in the target image. Additionally or alternatively, the processing device 120A may perform a coarse segmentation on the head, shoulders, hips, limbs, etc., of the subject to obtain a plurality of coarsely segmented regions. The processing device 120A may perform a fine segmentation on each of the plurality of coarsely segmented regions to obtain one or more finely segmented regions. For example, the processing device 120A may perform the fine segmentation on the abdominal region to obtain a liver region, a kidney region, etc. The processing device 120A may determine one of the plurality of fine segmentation regions as the ROI.

In 520, the processing device 120A (e.g., the image processing module 412) may obtain a focus position of the subject in the target image. The focus position may be associated with the ROI of the subject to be scanned or treated by the medical device.

In some embodiments, the focus position may be determined based on a user instruction with respect to moving the identifier in the target image. For example, the processing device 120A may determine a target position of the identifier corresponding to the target image based on the user instruction. The processing device 120A may designate the target position of the identifier as the focus position. As used herein, the focus position refers to a position or location of the identifier in the target image. The focus position of the identifier in the target image may indicate the position and/or range of the ROI of the subject to be scanned or treated by the medical device. In some embodiments, the identifier that can move according to the user instruction may also be referred to as a movable identifier. For example, the identifier of a line may also be referred to as a movable line, or the identifier of a dot may also be referred to as a movable dot. In some embodiments, the user may move the target image and/or the identifier to its target position. For example, the user may drag the target image and/or the identifier to change the location of the identifier in the target image. As another example, the user may move the target image or the identifier by one or more buttons. For instance, there may be a button for moving the target image or the identifier up, a button for moving the target image or the identifier down, a button for moving the target image or the identifier left, a button for moving the target image or the identifier right, a button for rotating or tilting the target image or the identifier, etc. The user may move the target image or the identifier by pressing or clicking the one or more buttons that can be used to move the target image or the identifier. In some embodiments, a recommendation list having a plurality of candidate focus positions may be predetermined. The processing device 120A or a user may determine the focus position based on the recommendation list. For example, the processing device 120A may transmit the recommendation list to a mobile terminal of the user and direct the mobile terminal to display the plurality of candidate focus positions to the user. The user may choose the focus position from the plurality of candidate focus positions in the recommendation list. The processing device 120A may determine the focus position based on the choice of the user. In some embodiments, the focus position of the identifier may be determined according to a protocol associated with a designated ROI of the subject. For example, the processing device 120A may obtain the protocol associated with the ROI. The processing device 120A may designate the initial position determined based on the protocol as the focus position. As another example, the processing device 120A may designate the initial position determined based on the protocol as a coarse focus position of the identifier. The processing device 120A may fine-tune the coarse focus position of the identifier to obtain the focus position based on a user instruction with respect to moving the identifier.

In some embodiments, the target image may include a mark on the subject. The processing device 120A may determine the focus position based on the mark. For example, the processing device 120A may project a positioning image associated with the ROI on the subject according to which the mark on the subject is determined. The processing device 120A may designate a position or location of the mark as the focus portion. More descriptions for determining the focus position based on the mark may be found elsewhere in the present disclosure (e.g., FIG. 6 and the descriptions thereof).

In some embodiments, the ROI (i.e., the region indicated by the identifier) of the subject in the target image may be displayed on the terminal device (e.g., the display 320) in high quality (e.g., in higher image resolution), compared to other parts in the target image that may be displayed in lower quality (e.g., in lower image resolution). In some embodiments, the brightness and/or color of the ROI of the subject in the target image may be different from the brightness and/or color of other parts in the target image. For example, the brightness of the ROI of the subject in the target image may be lower (i.e., darker) than that of the other parts of the subject in the target image. As another example, the color of the ROI of the subject in the target image may be blue while the color of other parts of the subject in the target image may be gray. As still an example, the color of the profile line of the ROI of the subject in the target image may be blue while the color of the profile lines of other parts of the subject in the target image may be gray. In some embodiments, the presentation (e.g., width, indentation, font size, font color) of the profile line of the ROI of the subject in the target image may be different from the presentation of the profile line of other parts of the subject in the target image. As used herein, a profile line of a region or part (e.g., an ROI) of a subject refers to a line that defines or delineates the contour of the region or part.

In 530, the processing device 120A (e.g., the control module 413) may determine a target table position based on the focus position. When the table is at the target table position, the ROI of the subject may be located at or in the vicinity of the isocenter of the medical device.

In some embodiments, the target table position may be represented by a target table code. The processing device 120A may generate a moving instruction based on the target table code and transmit the moving instruction to a drive device. Upon receiving the moving instruction, the drive device may drive the table to move to the target table code (i.e., the target table position).

In some embodiments, the processing device 120A may determine the target table position based on a reference position of the table in the target image and a mapping relationship between a physical length of the table and a virtual length of the table in the target image. For example, the processing device 120A may determine a reference distance between the reference position and the focus position in the target image. The processing device 120A may determine a physical distance between the target table position and the reference position of the table based on the reference distance and the mapping relationship. The processing device 120A may determine the target table position based on the physical distance and a current table position of the table (where the target image is acquired). In some embodiments, the reference position of the table may be any position in the target image. For example, the processing device 120A may determine an isocenter position (i.e., a position of the isocenter of the medical device) in the target image as the reference position, the processing device 120A may determine the reference distance based on the reference position and the focus position. As another example, the processing device 120A may determine a position of the table in the target image (e.g., a position of a center point of an edge of the table in the target image) as the reference position, and the processing device 120A may determine the reference distance based on the isocenter position, the focus position, and the reference position.

In some embodiments, the mapping relationship may be determined based on a ratio of the physical length and the corresponding virtual length of the table. For example, if the physical length of the long direction of the table is 2 meters, and the virtual length of the long direction of the table in the target image is 20 centimeters, the mapping relationship may be determined as 0.2/2=0.1; that is, the physical length of 1 meter corresponds to a virtual length of 0.1 meters in the target image. Additionally or alternatively, the processing device 120A may determine a count or number of pixels corresponding to the virtual length of a direction (e.g., the long direction) of the table in the target image. The processing device 120A may determine the physical length of the corresponding direction (e.g., the long direction) of the table. The processing device 120A may determine the mapping relationship based on the count or number of pixels of the virtual length and the corresponding physical length. For example, if the count or number of pixels corresponding to the virtual length of the long direction of the table is 2000, and the physical length of the long direction of the table is 2 meters, the mapping relationship may be determined as 2000/2=1000; that is, the physical length of 1 meter corresponds to 1000 pixels in the target image.

In some embodiments, the processing device 120A may predetermine or obtain a table position list (or table code list) based on a relationship between a position of the identifier in the target image and a corresponding table position (or table code). The processing device 120A may query the table position list (or table code list) to obtain the target table position (or table code) based on the focus position of the identifier. In some embodiments, the processing device 120A may store the table position list (or table code list) in the storage device 130, or any other storage device.

It should be noted that, according to the process 500, when the medical system 100 is used for scanning, one or more preliminary preparations may be simplified and/or automated, thereby reducing the time for preliminary preparation for the image scanning and improving the imaging efficiency. In addition, differences in the scanning position determination and the table movement caused by different users can be reduced, thereby improving the positioning accuracy of the scanning position and the imaging quality.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120A may determine whether any person is within a safe distance from an emergency stop button from a proximity sensor. If it is determined that no one is within the safe distance in a process of the movement of the table caused by a drive device, the processing device 120A may cause the table to stop moving and/or disconnect the drive device from the table.

In some embodiments, the processing device 120A may obtain the target protocol and/or scanning parameters corresponding to the target table position. The processing device 120A may cause the medical device to scan the ROI of the subject based on the obtained target protocol and/or the scanning parameters. For example, after obtaining the target protocol and/or the scanning parameters, the processing device 120A may generate a scanning instruction based on the obtained target protocol and/or the scanning parameters. The processing device 120A may transmit the scanning instruction to the medical device. Upon receiving the scanning instruction, the medical device may scan the subject according to the scanning instruction. In some embodiments, the scanning instruction may be generated by pressing a scanning button displayed on the terminal device. In some embodiments, after obtaining the target protocol and/or the scanning parameters, the processing device 120A may generate a dialog box to remind the user to confirm, reselect, and/or edit the obtained target protocol and/or scanning parameters. In some embodiments, an ROI of the subject to be scanned or treated may be determined based on the focus position. For instance, a centerline of the ROI illustrated in the target image may coincide with the focus position.

Figure 6:
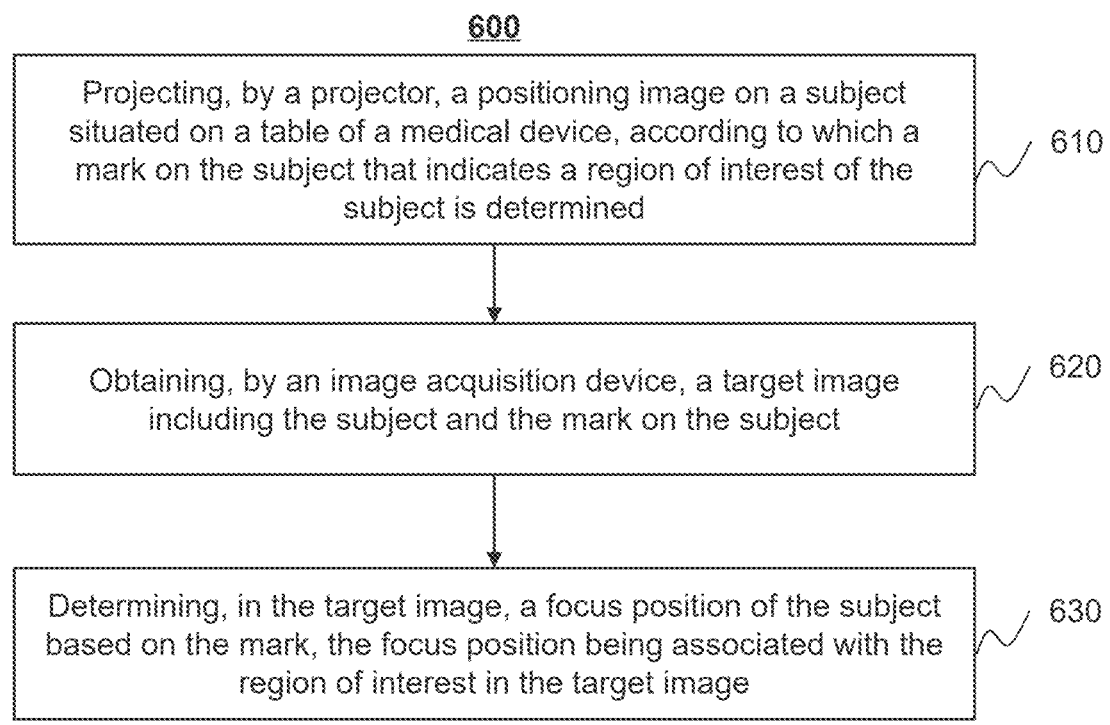
FIG. 6 is a flowchart illustrating an exemplary process for determining a focus position based on a mark on a subject according to some embodiments of the present disclosure.

FIG. 6 is a flowchart illustrating an exemplary process for determining a focus position based on a mark on a subject according to some embodiments of the present disclosure. In some embodiments, the process 600 may be implemented as a set of instructions (e.g., an application) stored in the storage device 130, storage 220, or storage 390. The processing device 120A, the processor 210 and/or the CPU 340 may execute the set of instructions, and when executing the instructions, the processing device 120A, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the focus position described elsewhere in the present disclosure (e.g., operation 520 illustrated in FIG. 5) may be obtained according to the process 600.

In 610, the processing device 120A (e.g., the control module 413) may cause a projector to project a positioning image on a subject situated on a table of a medical device. In some embodiments, the positioning image may be obtained from an imaging device (e.g., the medical device 110), the storage device 130, or any other storage device. For example, the imaging device may transmit acquired imaging data (e.g., projection data) to the storage device 130, or any other storage device for storage. The processing device 120A may obtain the imaging data from the storage device 130, or any other storage device, and generate the positioning image based on the imaging data. As another example, the processing device 120A may obtain the positioning image or the corresponding imaging data from the imaging device directly.

In some embodiments, the positioning image may be generated using an image reconstruction technique based on the imaging data (e.g., image data in the form of projection data). The positioning image may include information associated with structural (or anatomical structure) features of the subject. In some embodiments, the positioning image may include an MR image, a CT image, a positron emission computed tomography (PECT) image, a DR image, an ultrasound image, or the like, or any combination thereof. In some embodiments, the image reconstruction technique may include using a Fourier transform (FT) reconstruction, an iterative reconstruction, a backward projection (e.g., a convolution back-projection (CBP) technique, a filtering back-projection (FBP) technique), or the like, or any combination thereof.

The projector may be mounted above the table. The projector may project structured light presenting the positioning image on the subject. The structured light may include a structured light spot, a structured light stripe, a structured light grid, or the like. In some embodiments, the projector may project the structured light on the subject from different perspectives. For example, the projector may project the structured light on the subject from a plurality of projection angles. In some embodiments, the structured light projected by the projector may cover the entire body of the subject. Alternatively, the structured light may cover a portion of the body of the subject.

In some embodiments, the structured light presenting the positioning image may be adjusted based on one or more parameters of the projector. For example, the processing device 120A may project the positioning image on the subject according to preliminary projection parameters. The preliminary parameters may include a projection size, a projection location, a lying position and/or posture of the subject, information of the subject (e.g., height, weight, age, etc.), or the like, or any combination thereof. The preliminary parameters may be set according to a default setting of the medical system 100 or preset by a user via the terminal device 140. The processing device 120A may obtain a first image including a representation of the subject and the projected positioning image. The processing device 120A may determine adjusted projection parameters by adjusting, based on the first image, the preliminary projection parameters. The processing device 120A may project the positioning image on the subject according to the adjusted projection parameters such that the positioning image aligns with the subject. As used herein, the positioning image aligning with the subject indicates that a portion or position of the positioning image aligns with a corresponding portion or position of the subject. A size or area relating to the subject in the positioning image may be the same as a physical size or area relating to the subject.

In some embodiments, the positioning image may include one or more regions each of which corresponds to a portion of the subject. The processing device 120A may determine one or more segments each of which corresponds to one of the one or more regions by segmenting the positioning image. The processing device 120A may cause the projector to project at least one of the one or more segments of the positioning image on the corresponding portion of the subject. For example, if the positioning image includes a head region, the processing device 120A may cause the projector to project the head region of the positioning image on the head of the subject. As another example, if the positioning image includes a head region and an abdominal region, the processing device 120A may cause the projector to project the head region of the positioning image on the head of the subject and the abdominal region of the positioning image on the abdomen of the subject. In some embodiments, each of the one or more segments of the positioning image may be projected in different ways, for example, in different colors, in different brightness, with different profile lines, or the like, or a combination thereof.

The user may determine a mark indicating an ROI of the subject on the subject. For example, the user may use a marker pen to draw the mark on the subject based on the positioning image and/or indication information of the subject (e.g., a certain portion of the subject). As another example, the processing device 120A may identify a starting gesture and an ending gesture for drawing the mark. The processing device 120A may identify a trajectory of a finger of the user between time points of the starting gesture and the ending gesture. The processing device 120A may determine the mark based on the trajectory of the finger of the user. In some embodiments, the mark may include a box, a line, a dot, or any other shape that can indicate an ROI of the subject.

In some embodiments, the projector may project an interface of the medical device in a space where the user may access, e.g., on the table, on the subject. The processing device 120A may obtain a second image including a user gesture directed to the projected interface. The processing device 120A may identify the user gesture in the second image to obtain an analysis result. The processing device 120A may project the positioning image and/or updated interface based on the analysis result. For example, the processing device 120A may generate a control instruction based on the analysis result. The processing device 120A may control the projector to project the positioning image and/or updated interface based on the control instruction.

In some embodiments, the interface of the medical device may include a selection of information and/or data including the positioning image, information of the subject (e.g., an ROI of the subject), a scan protocol, a go-back operation, a forward operation, one or more imaging parameters, or the like, or any combination thereof. The go-back operation may be configured to enable the user to select one or more selectable information and/or select to return to a previous menu or page. For example, if the user selected a first positioning image of the subject, the user may trigger the go-back operation return to a previous manually and select another positioning image. As another example, after the user selected a first ROI of the subject, the user may trigger the go-back operation to return to a previous manually and select the first ROI and a second ROI of the subject. The forward operation may be configured to enable the user to take a next action and/or elect to turn to a next menu or page. For example, after the user selects the positioning image, the user may trigger the forward operation to turn to a next menu where the user may select a scan protocol. In some embodiments, the user may select information or provide an instruction by making a gesture.

In some embodiments, the user gesture may include covering a portion of the projected interface by a part (e.g., an arm, a palm) of the user or an object (e.g., a pair of scissors, a tray) to indicate the selection of information (e.g., the positioning image). The processing device 120A may cause the projector to project the selected information on the subject. For example, if the processing device 120A identifies that an icon or button on the projected interface indicating a selection of the positioning image of the subject is covered, the processing device 120A may cause the projector to project the positioning image on the subject. As another example, if the processing device 120A identifies that a palm of the user covers an icon or button on the projected interface indicating the go-back operation, the processing device 120A may perform the go-back operation. As still another example, if the processing device 120A identifies that a button indicating a scan protocol selection list is covered, the processing device 120A may cause the projector to project a sub-list of the scan protocol selection list.

In some embodiments, the user gesture may include a first sign, a V sign, a gesture with a specific count of fingers, etc., each of which corresponds to a selection of specific information of the projected interface. For example, the processing device 120A may identify a first sign corresponding to a selection of the positioning image to select the positioning image. As another example, the processing device 120A may identify a V sign corresponding a selection of the ROI to select the ROI. This may enhance the accuracy of the identification of a selection by the user by reducing the occurrence of an identification of a false selection. For instance, a false selection may occur when an icon or button on the projected interface is covered unintentionally by an external object (e.g., a tool the user is using), or a portion of the user (e.g., an arm of the user when the user tries to move his arm for purposes other than making a selection on the projected interface, or the head of the user when the user has moved his head trying to get a better view of the subject or a portion thereof), etc.

In 620, the processing device 120A (e.g., the control module 413) may cause the image acquisition device to obtain a target image including the subject and a mark on the subject. The image acquisition device may be the camera described elsewhere in the present disclosure (e.g., FIG. 5 and the descriptions thereof). The image acquisition device may be configured to capture one or more images of the structured light projected on the subject. In some embodiments, the image acquisition device may be mounted above the table. In some embodiments, the image acquisition device may be mounted in the vicinity of the projector.

In 630, the processing device 120A (e.g., the image processing module 412) may determine a focus position based on the mark in the target image. The focus position may be associated with the ROI in the target image. In some embodiments, the processing device 120A may determine the position of a centerline or a center point of the mark. The processing device 120A may designate the centerline or the center point of the mark as the focus position. For example, if the mark is a box, the processing device 120A may determine a position of the centerline of the box in the target image as the focus position. The centerline of the box may be vertical to the long direction of the table in the target image and may correspond to the focus position. As another example, if the mark is a line, the processing device 120A may determine a position of the center point of the line in the target image as the focus position.

In some embodiments, the processing device 120A may determine a target table position based on the focus position. When the table is positioned at the target table position, the ROI of the subject may be located at or in the vicinity of an isocenter of the medical device. More descriptions for determining the target table position based on the focus position may be found elsewhere in the present disclosure (e.g., FIG. 5 and the descriptions thereof).

It should be noted that, according to the process 600, an interaction between the user of the medical system 100 and the medical device of the medical system 100 may be facilitated by using the projector and the image acquisition device, so that when the user is working in the examination room, the user can directly interact with the processing device 120A of the medical system 100 in the control room.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 610 and operation 620 may be combined into a single operation. As another example, one or more other optional operations (e.g., a storing operation) may be added elsewhere in the process 600. As a further example, the processing device 120A may store information and/or data (e.g., the positioning image, the target image, the focus position, the target table position, etc.) associated with the medical system 100 in a storage device (e.g., the storage device 130) disclosed elsewhere in the present disclosure.

FIG. 7 is a schematic flowchart illustrating an exemplary process for determining a target area relating to a subject situated on a table of a medical device according to some embodiments of the present disclosure. In some embodiments, process 700 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In some embodiments, the medical system 100 may be a multi-modality system including a first device of a first modality and a second device of a second modality. The first device and/or the second device may be an imagining device (e.g., a PET device, a CT device, an MR device) or a treatment device (e.g., an RT device). For example, each of the first device and the second device may be an imagining device, e.g., the first device being an MR device and the second device being a PET device. When the subject is scanned in such a multi-modality system, scanning parameters (e.g., a field of view (FOV)) of the first device and scanning parameters (e.g., an FOV) of the second device may be set in concert, and the FOV of the first device may be different from (e.g., smaller than) the FOV of the second device. As another example, the first device may be a treatment device (e.g., an RT device) and the second device may be an imaging device (e.g., a CT device). For illustration purposes, the implementation of process 700 by the processing device 120B is described as an example.

In 710, the processing device 120B (e.g., the target area determination module 423) may identify a second target area relating to the subject for performing a second operation using the second device.

The second target area relating to the subject may be an area based on which the second device is directed to perform the second operation (e.g., an imaging operation, or a treatment operation) on an ROI of the subject to be scanned or treated. Merely by way of example, when the second device is an imaging device, the second target area may be an area based on which the second device is directed to perform the second operation (e.g., an imagining operation) on the subject. The second target area may correspond to an FOV of the second device (also referred to as a second FOV. In some embodiments, the second target area may be characterized by at least one parameter (also referred to as at least one second parameter) including, e.g., a center position of the second target area, a centerline of the second target area, an orientation of the second target area, an angle of the second target area with respect to a surface of the table, etc.

In some embodiments, the second target area relating to the subject may be determined based on a positioning image of the subject. The processing device 120B may obtain a positioning image of the subject. The positioning image of the subject may refer to a medical image acquired by medical scanning, an optical image, or another image including the ROI of the subject and may provide position information of the subject. The positioning image may be generated using the first device, the second device, or other medical/optical imaging device before or at the beginning of scanning the subject. The processing device 120B may identify the ROI of the subject in the positioning image. The processing device 120B may cause the table to move to a target table position. When the table is at the target table position, the ROI of the subject may be located at or in the vicinity of an isocenter of the second device, i.e., the ROI of the subject may be within an imaging area or treatment area of the second device. The target table position may be determined as is described in FIGS. 5-6, or manually by a user (e.g., a technician or doctor) of the medical system 100. The processing device 120B may determine the second target area relating to the subject based on the ROI of the subject such that the ROI of the subject falls within the second target area. More descriptions regarding determining the second target area based on the ROI may be found elsewhere in the present disclosure (e.g., FIGS. 9A-9B and the descriptions thereof).

In some embodiments, the second target area relating to the subject may be determined based on a model image of the subject. The processing device 120B may obtain a model image corresponding to the subject. The model image may relate to a virtual subject corresponding to the subject. For example, the processing device 120B may obtain the model image based on information of the subject (e.g., gender, height, weight, etc.). The processing device 120B may determine the second target area based on the virtual area and the positioning image of the subject. For example, the processing device 120B may determine in the model image a virtual area corresponding to the second target area. As used herein, a virtual area corresponding to the second target area refers to an area in the model image that corresponds to a virtual ROI. The virtual ROI refers to a portion of the model image including a representation of a specific portion corresponding to the ROI of the subject. The processing device 120B may determine the second target area based on the virtual area and the positioning image.

Figure 12:
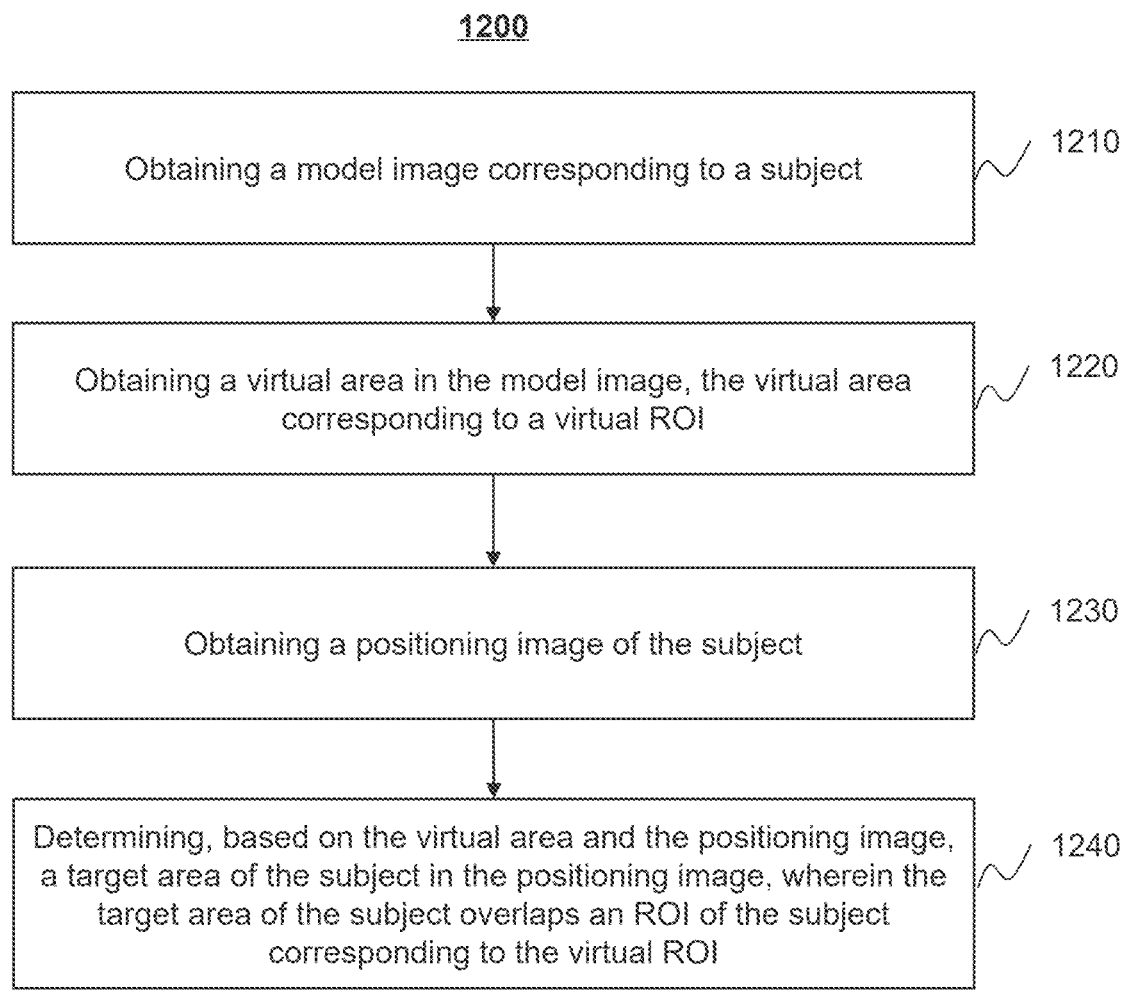
FIG. 12 is a schematic diagram illustrating an exemplary process for determining a target area relating to a subject in a positioning image according to some embodiments of the present disclosure.

The determination of the second target area based on the model image and the positioning image may be performed in a same or similar manner as that described in detail in FIG. 12, and is repeated here.

In 720, the processing device 120B (e.g., the target area determination module 423) may determine, based on the second target area, an initial target area relating to the subject for performing a first operation using the first device. The first operation may be an imagining operation or a treatment operation. For example, when the first device is an imagining device, the first operation may be an imagining operation. As another example, when the first device is a treatment device, the first operation may be a treatment operation.

In some embodiments, the processing device 120B may designate one or more of the at least one second parameter as corresponding parameter(s) that characterize(s) the initial target area. The parameter(s) characterizing the initial target area may also be referred to as initial parameter(s). For example, if a center of the second target area is denoted as (x,y) and designated as the corresponding parameter, the processing device 120B may copy (x,y) and designate (x,y) as a center of the initial target area. As another example, if a centerline of the second target area is denoted as "A" and designated as the corresponding parameter, the processing device 120B may copy "A" and designate "A" as a centerline of the initial target area. As still another example, the processing device 120B may designate both the center and the angle of the second target area as the corresponding parameters, and designate the center and the angle of the second target area as those of the initial target area. As still a further example, the processing device 120B may determine one or more preliminary parameters according to a default setting of the medical system 100 or a user instruction. The processing device 120B may replace at least one of the one or more preliminary parameters by copying corresponding value(s) of the at least one second parameter for determining the initial parameter(s). In some embodiments, the processing device 120B may determine one or more of the at least one second parameter and corresponding parameter(s) simultaneously. The processing device 120B may determine one of at least one second parameter and the corresponding parameter being of the same value. In some embodiments, the one or more of the at least one second parameter may be designated as the corresponding parameter(s) of the initial parameters according to a user instruction or automatically (e.g., the second device may automatically determine and/or transmit the one or more of the at least one second parameter to the first device as the corresponding parameter(s) of the initial parameters).

In 730, the processing device 120B (e.g., the target area determination module 423) may determine a first target area relating to the subject for performing the first operation using the first device by adjusting the initial target area.

In some embodiments, the processing device 120B may adjust the initial target area to be suitable for performing the first operation (e.g., an imaging operation or a treatment operation) using the first device. For example, a center of the initial target area may be determined as (x,y), and adjusted to be $(x_1, y_1)$. As another example, a location of a centerline of the initial target area may be determined as "A," and adjusted to be "$A_1$."

In some embodiments, the processing device 120B may identify an ROI of the subject associated with the first operation using the first device. As used herein, "the identifying an ROI of the subject" refers to obtaining or determining parameter(s) that characterize(s) the ROI of the subject (also referred to as ROI parameter(s)). Exemplary ROI parameters may include a center position of the ROI, a centerline of the ROI, an angle of the ROI with respect to the surface of the table, a boundary of the ROI, or the like, or any combination thereof. In some embodiments, the ROI parameters may be determined according to a positioning image of the subject, an optical image of the subject, historical information of the subject, or the like, or any combination thereof including the ROI. For example, the processing device 120B may determine a size, a position, an angle, etc., of the ROI according to a spatial relationship of the ROI (e.g., a liver) with respect to the positioning image (a whole). The positioning image including the ROI may be acquired using the second device, which makes full use of image data acquired by the second device, and decreases the use time and prolongs the lifespan of the first device. The ROI parameters identified from the positioning image may be accurate and/or comprehensive.

In some embodiments, the processing device 120B may adjust the initial target area based on the ROI of the subject such that the ROI of the subject is located within the first target area. The adjustment of the initial target area based on the ROI of the subject may include adjusting, based on the ROI of the subject and/or the ROI parameters, a center position of the initial target area, a centerline of the initial target area, an orientation of the initial target area, an angle of the initial target area with respect to a surface of the table, a boundary of the initial target area, a size of the initial target area, or the like, or any combination thereof. For the ROI of the subject being the liver of the subject on which the first operation is to be performed using the first device, the processing device 120B may adjust the initial target area based on a position of the liver in the subject, a size of the liver, etc., such that the liver of the subject is located within the adjusted initial target area. The processing device 120B may designate the adjusted initial target area as the first target area. For example, the processing device 120B may adjust the initial target area by copying one or more ROI parameters (e.g., a center position of the ROI, a centerline of the ROI, an angle of the ROI with respect to the surface of the table, a boundary of the ROI, etc.) and designate the one or more ROI parameters as the corresponding initial parameters. The adjusted initial target area may be designated as the first target area. More descriptions regarding adjusting the initial target area may be found elsewhere in the present disclosure (e.g., FIGS. 8-10 and the descriptions thereof).

In some embodiments, the processing device 120B may adjust the initial target area according to a preset adjustment strategy. Merely by way of example, as an increase of the initial target area may increase the imaging or treatment time, the preset adjustment strategy may be set for saving time for imagining or treatment. The preset adjustment strategy may include that a parameter that does not change the size of the initial target area has a higher priority than a parameter that changes the size of the initial target area in the adjustment process, and/or that a parameter that changes the size of the initial target area by a lesser extent has a higher priority than a parameter that changes the size of the initial target area by a larger extent in the adjustment process. Exemplary parameters that do not change the size of the initial target area or change it by a lesser extent may include the center position of the initial target area, the centerline of the initial target area, the angle of the initial target area with respect to the surface of the table, etc. Exemplary parameters that changes the size of the initial target area or changes it by a larger extent may include the size of the initial target area, the boundary of the initial target area, etc. A parameter that has a higher priority in the adjustment process may be changed before a parameter that has a lower priority. In some embodiments, only parameter(s) whose priority exceeds a threshold may be changed in an adjustment process. In some embodiments, one or more parameters may be designated as prohibited from being changed in an adjustment process.

In some embodiments, according to the process 700, at least one parameter of the first target area corresponding to a table position of the table may be variable to achieve a desirable result of the imaging or treatment operation by the first device. For example, during a PET/MR scan on a whole body of the subject, an MR scan may be performed according to a specific MR protocol at a particular table position. The target area in the MR protocol may be set with variable parameters to acquire a desirable MR image, e.g., an MR image that includes a representation of a complete ROI. For instance, for the ROI of the subject being the liver of a patient, the target area thereof may be determined according to diaphragm movements estimated based on breathing of the patient to obtain an MR image of the complete liver.

It should be noted that the above description regarding process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted.

Operations 720-730 may be omitted. The processing device 120B may directly determine the first target area relating to the subject the same as or similar to the determination of the second target area, e.g., based on the positioning image and/or the model image. In some embodiments, an addition operation may be added for causing the table to move to a target table position. The target table position may be determined based on the second target area. When the table is at the target table position, a centerline or a center point of the second target area may coincide with the isocenter of the second device.

In some embodiments, the first device may perform the first operation (e.g., an imaging operation, or a treatment operation) based on the first target area. The second device may perform the second operation (e.g., an imaging operation, or a treatment operation) based on the second target area. The first operation and the second operation may be performed in order or synchronously. For example, when the first device and the second device are imaging devices, the processing device 120B may acquire first image data by performing the first operation using the first device based on the first target area. The processing device 120B may acquire second image data by performing the second operation using the second device based on the second target area. The first operation and the second operation may be performed synchronously or in order. The processing device 120B may display a fusion image based on the first image data and the second image on a terminal (e.g., the terminal device 140).

In some embodiments, for performing a multi-modality operation (e.g., a PET/MRI operation) on the subject, the processing device 120B may obtain a protocol for the subject. For example, if a full-body scan is needed, the processing device 120B may obtain a PET scan protocol template that is used for a full-body scan. The protocol may be selected manually or automatically based on information of the subject, a habit of the user (e.g., a technician or doctor), a preset rule or preference, or the like, or a combination thereof. The protocol may be displayed on a terminal (e.g., the terminal device 140) with a corresponding image for visualizing the protocol. The corresponding image may be a pre-stored image corresponding to the protocol or generated in real-time according to a particular rule and the protocol. For example, the corresponding image may be the model image as described elsewhere in the present disclosure (e.g., FIGS. 12, 20 and the descriptions thereof), which may display a virtual area corresponding to the protocol. The processing device 120B may adjust parameters in the protocol for generating a target protocol. The parameters of the protocol may be adjusted by opening a function (e.g., "MRI Off-Center," "MRI Off-centerline," "MRI Off-Angle," "MRI Off-Boundary," "MRI Off-Upper Boundary," "MRI Off-Lower Boundary," "MRI Off-Left Boundary," "MRI Off-Right Boundary," etc.) according to, e.g., the process described in operations 710-730. The second target area of the PET device and the first target area of the MR device may be determined based on a corresponding ROI, wherein the first target area of the MR device is determined by copying the second target area (e.g., at least one second parameter) to generate the initial target area and adjusting the initial target area. Then the table is moved to a target table position (e.g., a table position A) based on the protocol, and the subject may be scanned by the PET device and the MR device at the target table position based on the second target area and the first target area synchronously.

Figure 8A:
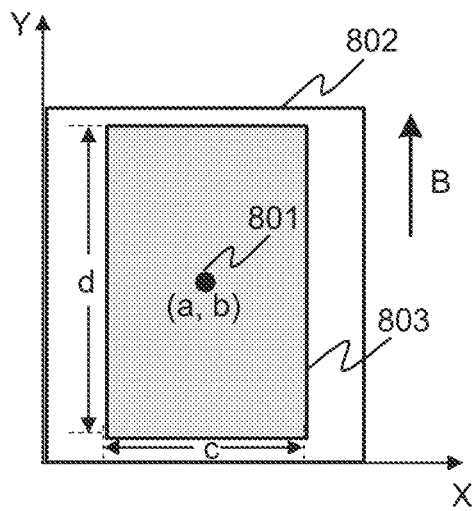
FIG. 8A is a schematic diagram illustrating an exemplary initial target and an exemplary second target area according to some embodiments of the present disclosure.

FIG. 8A is a schematic diagram illustrating an exemplary initial target and an exemplary second target area according to some embodiments of the present disclosure. Either one or both of the second target area 802 and the initial target area 803 may be of a rectangular shape. The second target area 802 may include two pairs of parallel boundaries. Each pair of parallel boundaries may form an angle with a long direction of the surface of the table (e.g., arrow B). The smaller angle of the two angles may be designated as an angle of the second target area 802 with respect to the surface of the table. For illustration purposes, a 2D coordinate system set based on the second target area 802 is provided. As shown in FIG. 8A, the 2D coordinate system may include an X-axis coinciding with a lower boundary of the second target area 802, and a Y-axis coinciding with a left boundary of the second target area 802. A center 801 of the second target area 802 may be denoted as (a, b), and the angle of the second target area 802 with respect to the surface of the table may be 0. The initial target area 803 may be determined based on the second target area 802. A center of the initial target area 803 may be determined by the center of the second target area 802, and an angle of the initial target area 803 with respect to the surface of the table may be determined to be equal to the angle of the second target area 802 with respect to the surface of the table. Boundaries of the initial target area may be further determined based on a preset size of (c, d), i.e., a left boundary of the initial target area 803 may coincide with a line of x=a−c/2, a right boundary of the initial target area 803 may coincide with a line of x=a−c/2, a lower boundary of the initial target area 803 may coincide with a line of y=b−d/2, and an upper boundary of the initial target area 803 may coincide with a line of y=b+d/2.

Figure 8B:
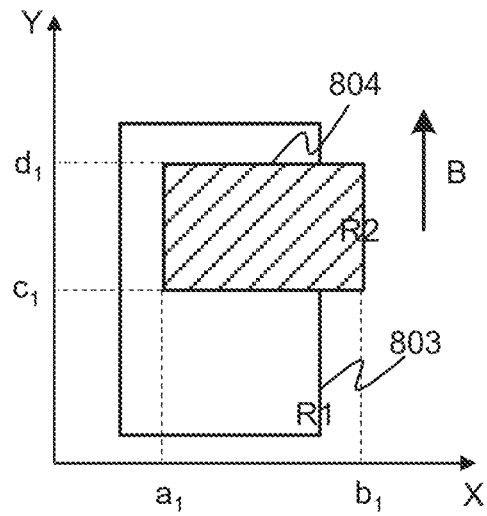
FIG. 8B is a schematic diagram illustrating an exemplary ROI and the initial target area as shown in FIG. 8A according to some embodiments of the present disclosure.

FIG. 8B is a schematic diagram illustrating an exemplary ROI and the initial target area as shown in FIG. 8A according to some embodiments of the present disclosure. The ROI 804 (i.e., the hashed rectangle shown in FIG. 8B) may include a left boundary coinciding with a line of $x=a_1$, a right boundary coincided with a line of $x=b_1$, a lower boundary coincided with a line of $y=c_1$, and an upper boundary coincided with a line of $y=d_1$, wherein $a_1<b_1$, $c_1<d_1$. As shown in FIG. 8B, the ROI 804 is not within the initial target area 803 as the right boundary R2 of the ROI 804 is outside the right boundary R1 of the initial target area 803 (e.g., $b_1>a+c/2$).

Figure 8C:
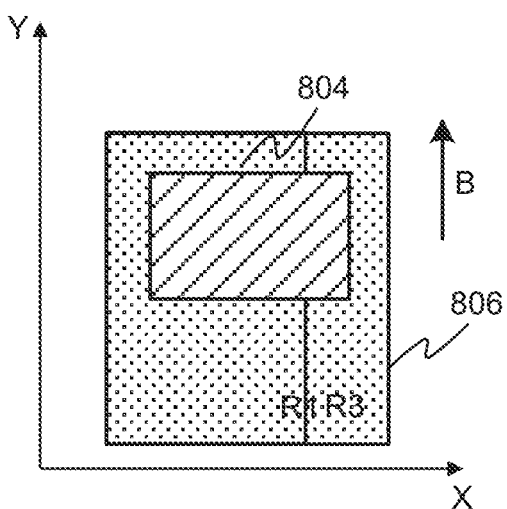
FIG. 8C is a schematic diagram illustrating an exemplary adjusted initial target area and the ROI according to some embodiments of the present disclosure.

In some embodiments, the initial target area 803 may be adjusted by adjusting the right boundary R1 of the initial target area 803. FIG. 8C is a schematic diagram illustrating an exemplary adjusted initial target area and the ROI according to some embodiments of the present disclosure. The adjusted initial target area 805 may be determined based on boundaries of the ROI 804. As shown in FIG. 8C, the adjusted initial target area 805 (i.e., a dot-filled rectangle shown in FIG. 8C) may be determined by adjusting the right boundary R1 of the initial target area 803 so that the right boundary R3 of the adjusted initial target area 805 aligns with the right boundary R1 of the ROI 804. The adjusted initial target area 805 may include a left boundary coinciding with a line of x=a−c/2, a right boundary coinciding with a line of $x=b_1$, a lower boundary coinciding with a line of y=b−d/2, and an upper boundary coinciding with a line of y=b+d/2.

Figure 8D:
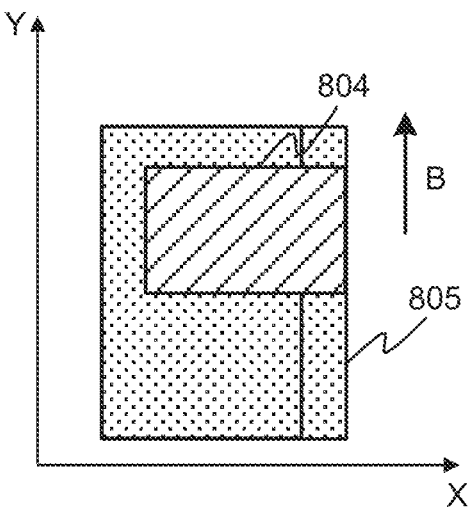
FIG. 8D is a schematic diagram illustrating an exemplary first target area and the ROI as shown in FIGS. 8B-8C according to some embodiments of the present disclosure.

In some embodiments, the adjusted initial target area 805 may be further adjusted for determining a first target area. FIG. 8D is a schematic diagram illustrating an exemplary first target area and the ROI as shown in FIGS. 8B-8C according to some embodiments of the present disclosure. The first target area 806 (i.e., a dot-filled rectangle shown in FIG. 8D) may be determined by adjusting the adjusted initial target area 805 based on a preset rule. For example, the adjusted initial target area 805 may be adjusted for reserving a space between boundaries of the adjusted initial target area 805 and boundaries of the ROI 804, which may reduce or avoid the effect of a deformation of an image at boundaries of the ROI 804 and provide an accurate image of the ROI 804 for a user (e.g., a doctor). As shown in FIG. 8D, the first target area 806 may include a left boundary coinciding with a line of x=a−c/2, a right boundary coinciding with a line of $x=b_1+e$, a lower boundary coinciding with a line of y=b−d/2, and an upper boundary coinciding with a line of y=b+d/2, wherein e may be a positive value which is set by the user of the medical system 100 or according to a default setting of the medical system 100.

Figure 10A:
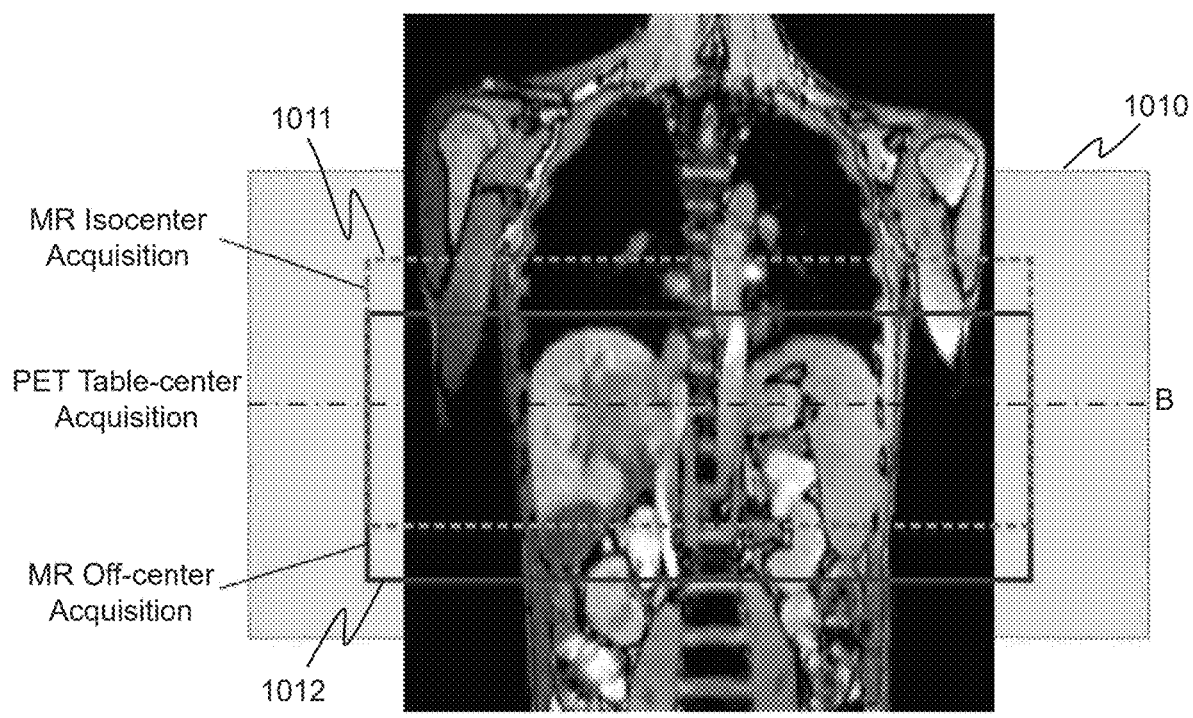
FIGS. 10A-10C are schematic diagrams illustrating exemplary target areas in a PET-MR system according to some embodiments of the present disclosure.
Figure 10B:
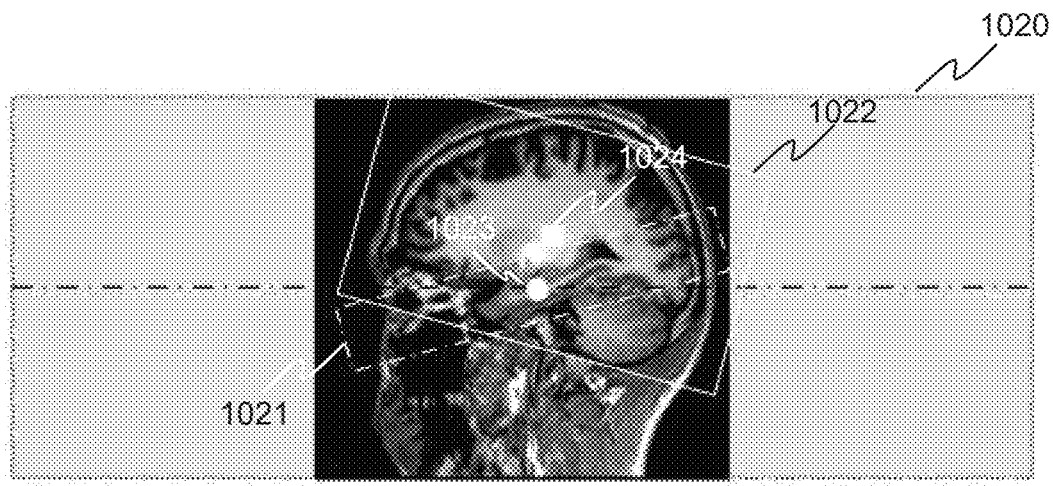
Figure 10C:
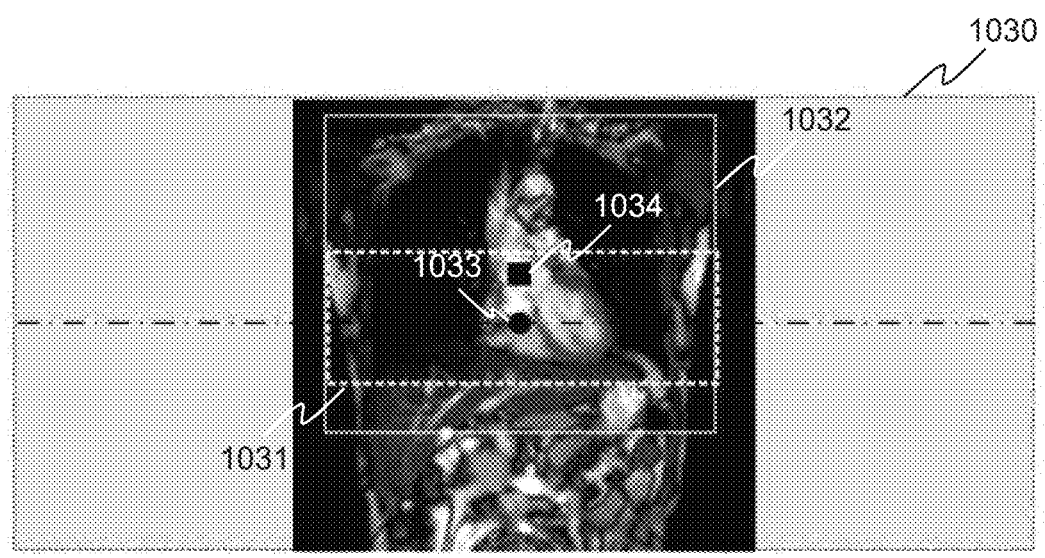

FIGS. 10A-10C are schematic diagrams illustrating exemplary target areas in a PET-MR system according to some embodiments of the present disclosure. The PET-MR system may be a large functional metabolism and molecular imaging diagnostic system including a PET device and an MR device for imaging. The PET device may be designated as a second device and the MR device may be designated as a first device.

FIG. 10A is a schematic diagram illustrating exemplary target areas associated with the liver of a subject for a PET-MR system according to some embodiments of the present disclosure. As shown in FIG. 10A, a positioning image associated with the liver is provided. A centerline of an initial target area 1020 may coincide with that of a second target area 1010, i.e., the centerlines of the initial target area 1020 and the second target area 1010 both being a line B as shown in FIG. 10A. A first target area 1012 may be determined by adjusting the initial target area 1011 based on the liver of the subject such that the liver of the subject may be within the first target area 1012. For example, the initial target area 1020 may be adjusted based on a position associated with the liver of the subject in the positioning image, e.g., adjusting an upper boundary of the initial target area 1011 based on a coordinate of a highest point of an upper boundary of the liver, adjusting a lower boundary of the initial target area 1011 based on a coordinate of a lowest point of a lower boundary of the liver, or adjusting a position of the centerline of the initial target area 1011 based on a position of a centerline of the liver. The initial target area 1011 may be labeled by "MR Isocenter Acquisition" which represents that a center of the initial target area 1011 is the same as a center of the second target area 1010 at a particular table position. The first target area 1012 may be labeled by "MR Off-Center Acquisition" which represents that the center of the initial target area 1011 is determined based on an ROI and is different from the center of the second target area 1010 at the particular table position.

FIG. 10B is a schematic diagram illustrating exemplary target areas associated with the brain of a subject for a PET-MR system according to some embodiments of the present disclosure. As shown in FIG. 10B, a positioning image associated with the brain is provided. The second device (i.e., the PET device) may be used to perform a fine scan on a neural system in the brain. A second target area 1020 may include a center 1023 (i.e., a dot as shown in FIG. 10B) and an angle of the second target area 1020 may be 0. When an ROI for the first device (i.e., the MR device) is the hippocampus, a corresponding initial target area (not shown) may be determined by copying the center 1023 and the angle of the second target area 1020. A corresponding first target area 1021 may be determined by adjusting the angle of the corresponding initial target area from 0 to −15°, i.e., rotating the corresponding initial target area 15° counterclockwise around the center 1023. When an ROI of the first device (i.e., the MR device) is the whole brain, a corresponding initial target area (not shown) may be determined by copying the center 1023 and the angle of the second target area 1020. A corresponding first target area 1022 may be determined by adjusting the angle of the corresponding initial target area from 0 to +15° (i.e., rotating the corresponding initial target area 15° clockwise around the center 1023), adjusting the center of the corresponding initial target area from the center 1023 to a center 1024 (i.e., a point as shown in FIG. 10B) and increasing the corresponding initial target area such that the whole brain is within the first target area 1022.

FIG. 10C is a schematic diagram illustrating exemplary target areas associated with the heart of a subject for a PET-MR system according to some embodiments of the present disclosure. As shown in FIG. 10C, a positioning image associated with the heart is provided. The second device (i.e., the PET device) may be used to perform a multiplane scan on the heart. A second target area 1030 may include a center 1033 (i.e., a dot as shown in FIG. 10C) and an angle of the second target area 1030 may be 0. When an ROI of the first device (i.e., the MR device) is the myocardium, a corresponding initial target area 1031 may be determined by copying the center 1033 and the angle of the second target area 1030. The corresponding initial target area 1031 may be suitable for scanning the myocardium (e.g., the myocardium being within the initial target are 1031) and the corresponding initial target area 1031 may be designated as a corresponding first target area. When an ROI of the first device (i.e., the MR device) is the whole chest, the corresponding initial target area 1031 may be determined by copying the center 1033 and the angle of the second target area 1020. A corresponding first target area 1032 may be determined by adjusting the center of the corresponding initial target area 1031 from the center 1033 to a center 1034 (i.e., a point as shown in FIG. 10C) and adjusting a size of the corresponding initial target area 1031 such that the whole chest may be within the first target area 1032.

Figure 11:
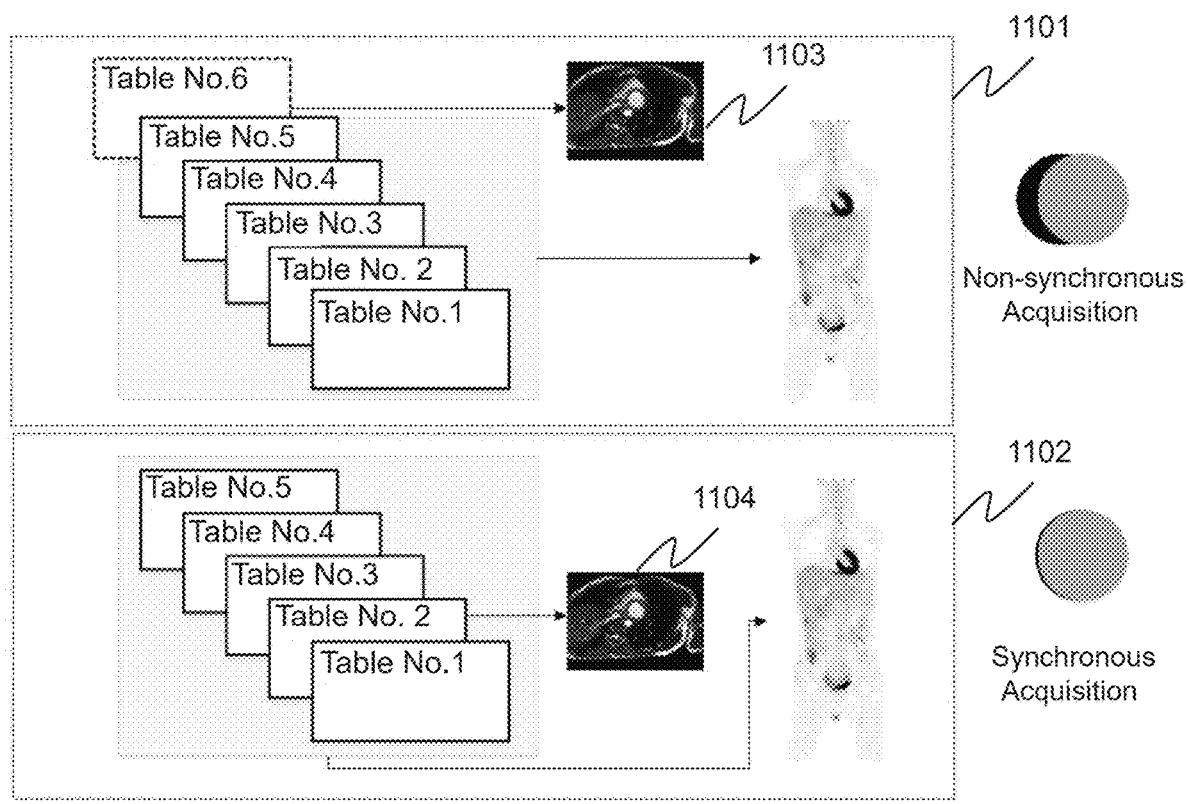
FIG. 11 is a schematic diagram illustrating an exemplary process for determining target areas in a PET-MR system according to some embodiments of the present disclosure.

FIG. 11 is a schematic diagram illustrating an exemplary process for determining target areas in a PET-MR system according to some embodiments of the present disclosure. The PET-MR system may include a PET device and an MR device. In some embodiments, the PET device may need to perform a scan on a subject at different table positions, while the MR device may need to perform a scan on the subject at only one table position.

As shown in 1101, for each table position (e.g., each of table Nos. 1-6), a first target area corresponding to an FOV of the MR device may be set in concert with a second target area corresponding to an FOV of the PET device. The PET device may perform a scan based on the second target area at the each table position to obtain a PET image. Simultaneously, the MR device may perform a scan based on the first target area at the each table position to obtain an MR image. In some embodiments, at least part of an ROI of the subject may be located outside the first target area, and the MR image may include only part of the whole ROI. The MR device may need to perform a supplementary scan at a particular table position (e.g., a table No. 6) based on a new first target area (e.g., a target area 1103) to obtain a supplementary MR image, which may result in a misalignment between the PET image and the supplementary MR image and a relatively large deviation for displaying a fusion PET-MR image, and consumes workload and time.

As shown in 1102, according to the process 700, a first target area at a particular table position (e.g., a target area 1104 at the table No. 2) may be set based on the ROI of the subject to achieve a desirable result that the ROI is within the target area 1104. For example, the PET device may perform a scan at each table position (e.g., each of table Nos. 1-5) based on the second target area to obtain the PET image. Synchronously, the MR device may perform a scan at table No. 2 based on the target area 1104 to obtain an MR image. The PET image and the MR image may align more accurately, thereby reducing workload and time for image scanning and/or image reconstruction.

FIG. 12 is a schematic diagram illustrating an exemplary process for determining a target area relating to a subject in a positioning image according to some embodiments of the present disclosure. In some embodiments, process 1200 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 1200. The operations of the illustrated process presented below are intended to be illustrative. In some embodiments, the process 1200 may be accomplished with one or more additional operations not described and/or without one or more of the operations discussed. Additionally, the order of the operations of process 1200 illustrated in FIG. 12 and described below is not intended to be limiting. In some embodiments, the process 1200 may be used for determining a target area relating to a subject to be scanned or treated by a medical device of a single modality, or of a multi-modality. In some embodiments, operation 710 in FIG. 7 may be achieved by one or more operations of the process 1200.

In 1210, the processing device 120B (e.g., the acquisition module 421) may obtain a model image corresponding to the subject. As used herein, the model image corresponding to the subject may refer to an image including a plurality of virtual ROIs corresponding to a plurality of ROIs of the subject.

In some embodiments, the model image may include an image of a human, an animal, or any other object of a same type as the subject. In some embodiments, a model image may include a 2D image, a 3D image, etc. For instance, a model image may include a 3D image that in turn includes a series of 2D images. For illustration, the subject is a human, a female patient, and the model image corresponding to the subject may include an image of a female. The female image may be constructed based on a standard female model. In some embodiments, the standard female model may be adjusted based on information of the height, the weight, the body shape, a lesion of interest (e.g., to be imaged and/or treated), an age, a medical history, or the like, or any combination thereof, of the subject. That is, the processing device 120B may obtain the model image corresponding the subject based on information of the subject. In some embodiments, the adjustment may need to be confirmed and/or input by a user (e.g., a technician or doctor).

In some embodiments, one or more model images may be predetermined and stored in a storage device (e.g., the storage device 130, storage 220, and/or storage 390). The processing device 120B may retrieve a model image corresponding to the subject among the one or more model images from the storage device. In some embodiments, the user may provide a user instruction on the basis of which the processing device 120B retrieves the model image.

Figure 13:
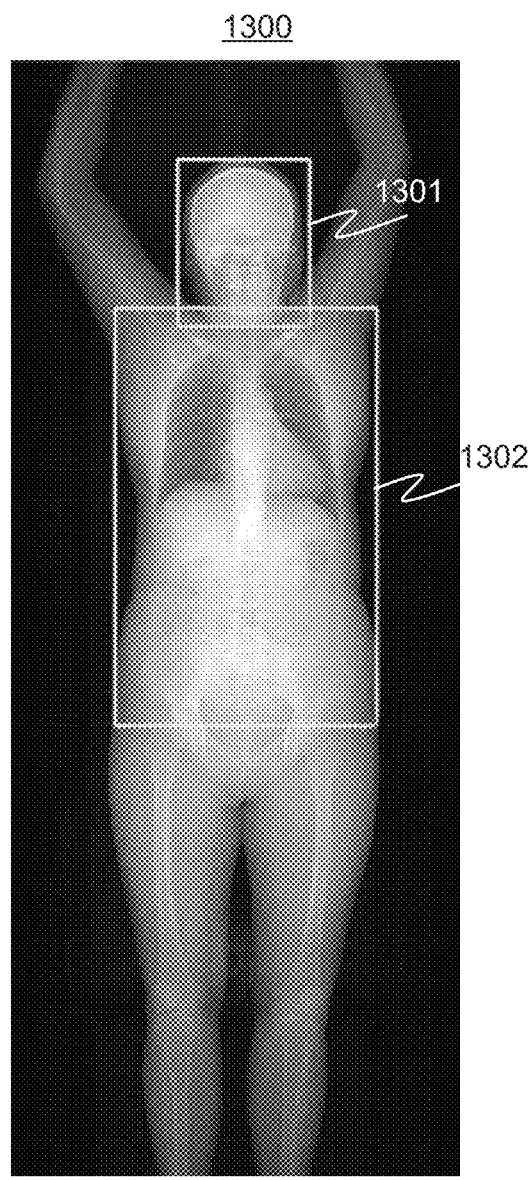
FIG. 13 is a schematic diagram illustrating a model image corresponding to a subject according to some embodiments of the present disclosure.

In some embodiments, the model image corresponding to the subject may be displayed on a terminal (e.g., a displayed panel of the terminal device 140) for the user (e.g., a technician or doctor) to view, providing user instruction regarding an adjustment to make, and/or confirm. The model image may be displayed visibly differently from the background of the displayed panel for conveniently viewing model image. For example, the model image may be displayed in white, while the background of the panel may be displayed in black as shown in FIG. 13.

In 1220, the processing device 120B (e.g., the virtual area determination module 422) may obtain a virtual area in the model image. The virtual area may correspond to a virtual ROI.

The virtual ROI may correspond to an ROI of the subject to be scanned or treated. For the subject being a human, the ROI of the subject may include a specific portion of the subject, e.g., a lesion in the subject, an organ of the subject, a tissue of the subject, or the like, or any combination thereof. Exemplary ROIs may include the head, the neck, the thorax, the heart, the stomach, a leg, the chest, a blood vessel, soft tissue, a tumor, nodules, or the like, or any combination thereof the subject. For example, if adverse symptoms show in the head of the subject, the head of the subject may be an ROI of the subject to be scanned for diagnosis and/or treatment.

Figure 14:
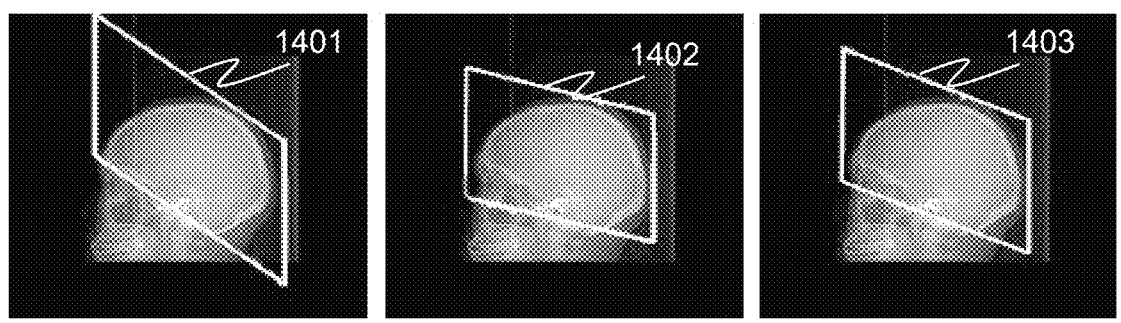
FIG. 14 is schematic diagrams illustrating exemplary virtual ROIs of a virtual head according to some embodiments of the present disclosure.

FIG. 14 is schematic diagram illustrating exemplary virtual ROIs of a virtual head according to some embodiments of the present disclosure. As used herein, a virtual ROI may be a portion of a model image including a representation of a specific portion corresponding to an ROI of the subject. As shown in FIG. 14, the virtual head may include a virtual ROI within a box 1411, a virtual ROI within a box 1412, a virtual ROI within a box 1413, or the like that are not shown in FIG. 14. The virtual ROIs may be different from each other. Exemplary virtual ROIs of the virtual head may include a representation of the hippocampus, the hypothalamus, the amygdaloid nucleus, or the like, or any combination thereof, within the model image of the brain of the subject.

In some embodiments, a virtual area corresponding to each of different virtual ROIs in the model image may be displayed in a single layer or multiple layers. FIG. 13 is a schematic diagram illustrating a model image corresponding to a subject according to some embodiments of the present disclosure. As shown in FIG. 13, a virtual area 1301 corresponds to a representation of a head in the model image 1300, and a virtual area 1302 of a representation of an upper body in the model image 1300. Each of the virtual areas 1301 and 1302 may be of a rectangular shape. As the virtual area 1301 may partially overlap or be intersected by the virtual area 1302 in the model image 1300, the virtual area 1301 and the virtual area 1302 may be displayed on a displayed panel in two layers or views (not shown in FIG. 13). For example, the virtual area 1301 and the model image 1300 may be displayed in one layer or view, and the virtual area 1302 and the model image 1300 may be displayed in another layer or view. As another example, the virtual head and the virtual upper body may be segmented from the model image 1300. The virtual area 1301 with the virtual head may be displayed in one layer or view, and the virtual area 1302 with the virtual upper body may be displayed in another layer or view. In some embodiments, the boundary of the virtual area may be visibly different from the background of the displayed panel. For example, the color of the boundary of the virtual area may be set to be yellow or green, and the color of the background of the displayed panel may be set to be black.

In some embodiments, the processing device 120B may obtain a protocol (e.g., a scan protocol or a treatment protocol) associated with the ROI of the subject. The processing device 120B may obtain the virtual area in the model image based on the protocol. For example, the processing device 120B may determine the virtual area based on a first relation between the virtual ROI and the protocol and a second relation between the virtual ROI and an automated positioning model, the description of which may be found in FIG. 15 and the description thereof. As another example, the processing device may determine the virtual area based on the protocol and a protocol-virtual area relationship. The virtual area may be directly displayed on the model image. More descriptions regarding the determination of the protocol-virtual area relationship may be found elsewhere in the present disclosure (e.g., FIG. 20 and the descriptions thereof).

In 1230, the processing device 120B (e.g., the acquisition module 421) may obtain a positioning image of the subject.

The positioning image of the subject may refer to a medical image acquired by medical scanning, an optical image, or another image including the ROI of the subject as described elsewhere in the present disclosure. For example, for the ROI of the subject being the head, the positioning image may be an image including the head of the subject. For instance, the positioning image may be a head image acquired by a camera, laser, etc. In some embodiments, the positioning image may be acquired in real-time or may be acquired in advance and stored in a storage device (e.g., the storage device 130, storage 220, and/or storage 390) for subsequent use. The processing device 120B may obtain the positioning image in real-time or retrieve the positioning image from the storage device.

Figure 9A:
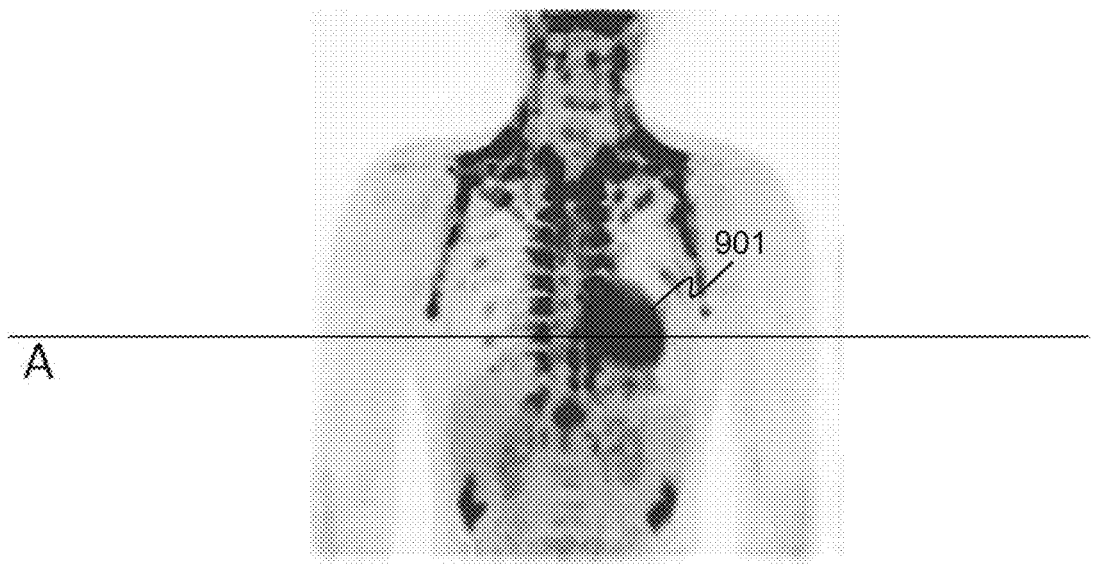
FIGS. 9A-9D are schematic diagrams illustrating an exemplary positioning image of a subject and/or exemplary target areas according to some embodiments of the present disclosure.
Figure 9B:
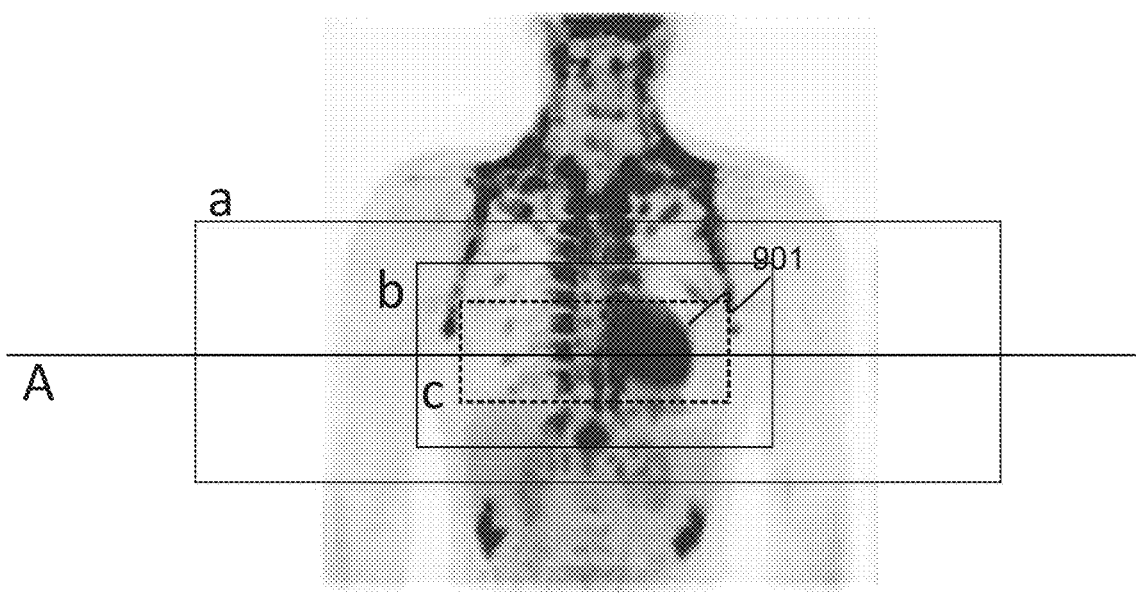

FIGS. 9A-9D are schematic diagrams illustrating an exemplary positioning image of a subject and/or exemplary target areas according to some embodiments of the present disclosure. An ROI 901 may be the heart of the subject, and the heart may include an irregular shape as shown in FIGS. 9A-9D. The processing device 120B may identify the heart of the subject in the positioning image and determine a line "A" that passes or aligns with a center of the heart of the subject. The processing device 120B may determine the line "A" as a centerline of a second target area "a" as shown in FIG. 9B. The processing device 120B may determine other parameter(s) of the second target area "a" based on the heart of the subject such that the heart of the subject may be within the second target area "a" as shown in FIG. 9B.

In some embodiments, the processing device 120B may determine an initial target area based on the second target area. For example, the processing device 120B may determine a centerline of the initial target area "c" by copying the centerline of the second target area "a," i.e., the centerlines of both the second target area and the initial target area being the line "A." As another example, the processing device 120B may determine a center and angle of the initial target area "c" by copying those of the second target area "a," i.e., the center and angle of the initial target "c" may coincide with those of the second target area "a." As shown in FIG. 9B, an upper boundary of the heart may be above an upper boundary of the initial target area "c." If the subject is imaged based on the initial target area "c," an incomplete image of the heart may be acquired. Additionally or alternatively, for an imaging device, the image quality at the boundaries of a target area may be lower than that in a center of the target area. Thus, it is desirable to adjust the initial target area "c" for acquiring an image that includes a representation of the entire heart of the subject.

Figure 9C:
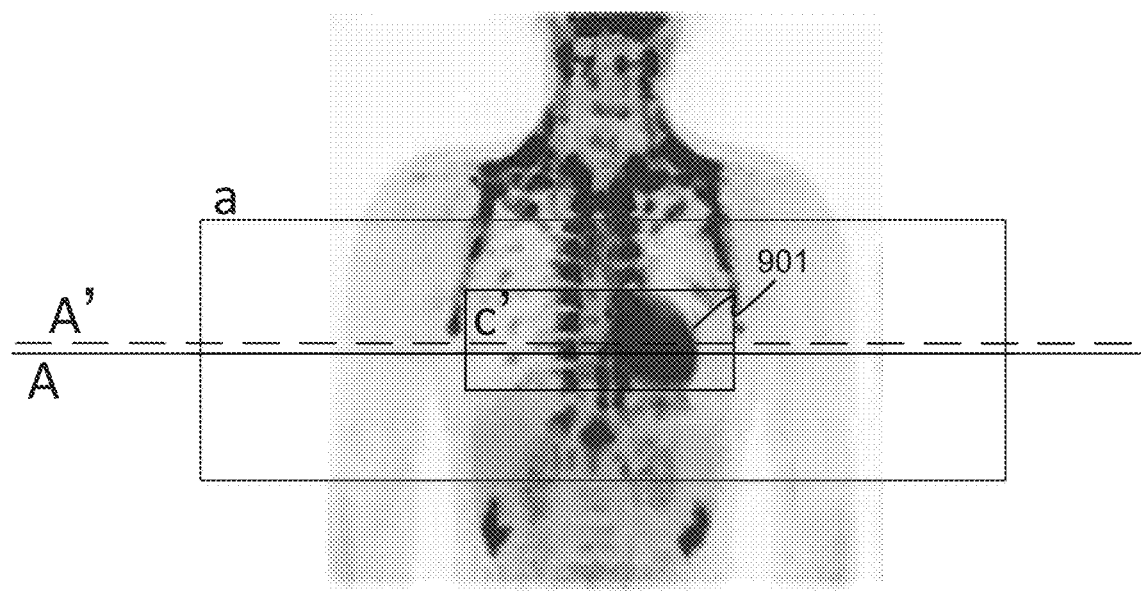
Figure 9D:
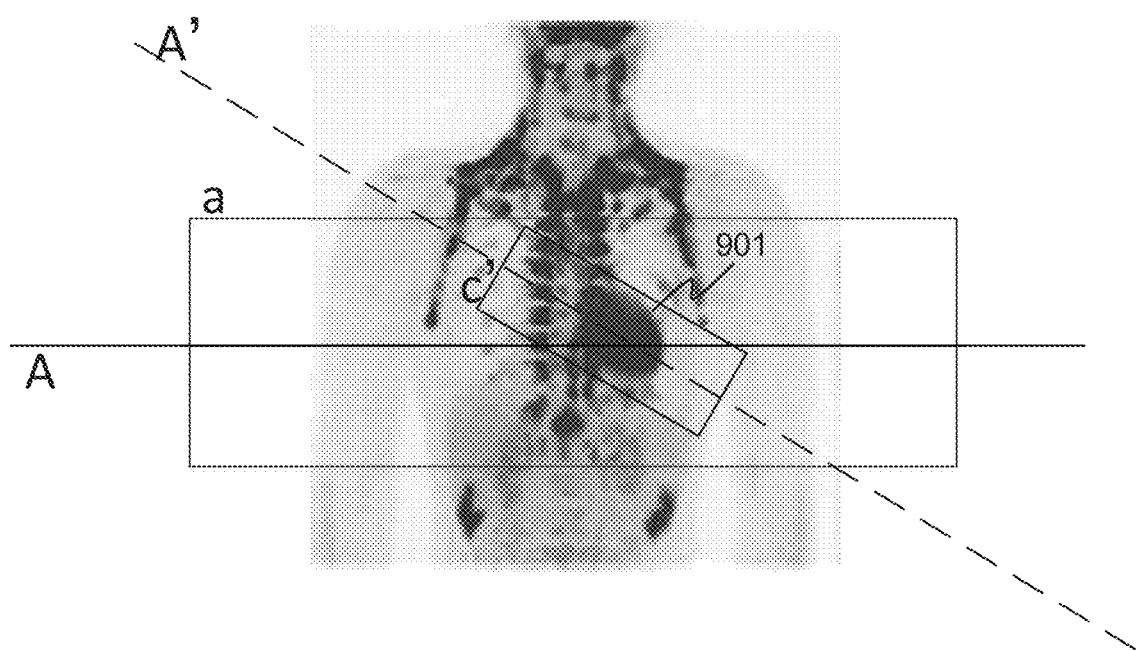

In some embodiments, the processing device 120B may adjust at least one of the center position of the initial target area "c," the centerline of the initial target area "c," an orientation of the initial target area "c," the angle of the initial target area "c" with respect to a surface of the table, a boundary of the initial target area "c," a size of the initial target area "c," or the like, or any combination thereof. In some embodiments, the processing device 120B may adjust one or more parameters that characterize the initial target area "c" by copying corresponding parameter(s) that characterize(s) the ROI 901. The processing device 120B may acquire the positioning image of the subject in real-time and determine the parameters that characterize the ROI 901 in the positioning image for adjusting the initial target area "c"

in real-time. For example, the processing device 120B may adjust the size of the initial target area "c," e.g., increasing the initial target area "c." The processing device 120B may determine a first target area "b" by adjusting the size of the initial target area "c" such that the heart of the subject may be within the first target area "b", as shown in FIG. 9B. As another example, the processing device 120B may adjust a position of the centerline of the initial target area "c," which may not change the size of the initial target area "c." As shown in FIG. 9C, the processing device 120B may determine a first target area "c'" by moving the centerline of the initial target area "c" from the line A to a line "A'" such that the heart of the subject may be within the first target area "c'" as shown in FIG. 9C. As shown in FIG. 9D, the processing device 120B may determine a first target area "c'" by rotating the centerline of the initial target area "c" from the line A to a line "A'" such that the heart of the subject may be within the first target area "c'" as shown in FIG. 9D. According to FIGS. 9C-9D, the initial target area may be adjusted by not changing a size of the initial target area. An image including a representation of a complete ROI may be acquired without increasing the imaging time or the amount of data to be acquired, thereby improving the efficiency of the imaging process and the image reconstruction process without compromising the image quality or completeness. Merely by way of example, for the first device being an MR device, the first device may perform a scan based on the adjusted initial target area, using fewer MR layers to cover the whole ROI and saving the scan time.

In 1240, the processing device 120B (e.g., the target area determination module 423) may determine, based on the virtual area and the positioning image, a target area relating to the subject in the positioning image. The target area relating to the subject may corresponding to the ROI of the subject corresponding to the virtual ROI. The target area relating to the subject may be of a rectangular shape.

The processing device 120B may determine the target area relating to the subject in the positioning image by processing the virtual area and the positioning image. For the ROI of the subject being the head, the processing device 120B may determine the target area of the head by processing a virtual area corresponding to the head and a positioning image including the head.

In some embodiments, the processing device 120B may determine, in the positioning image, the ROI of the subject based on the virtual ROI. Merely by way of example, the processing device 120B may identify a first feature relating to the virtual ROI in the model image, for example, by identifying the virtual ROI in the virtual area. The processing device 120B may identify a second feature in the positioning image, wherein the degree of similarity between the first feature and the second feature exceeds a predetermined threshold. The degree of similarity between features identified in two images may be determined based on, e.g., a Euclidean distance algorithm, a Manhattan distance algorithm, a Minkowski distance, a cosine similarity algorithm, a Jaccard similarity algorithm, a Pearson correlation algorithm, or the like, or any combination thereof. The processing device 120B may determine, based on the second feature, the ROI in the positioning image. The processing device 120B may determine the target area in the positioning image based on the ROI.

Figure 16:
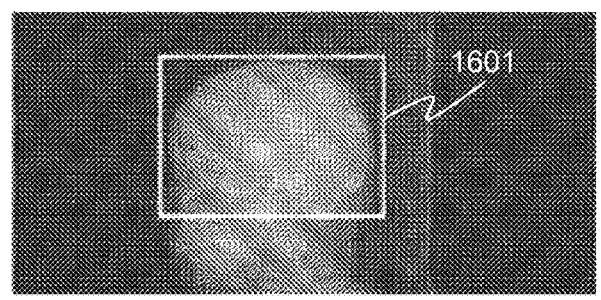
FIG. 16 is a schematic diagram illustrating an exemplary virtual area of a virtual head according to some embodiments of the present disclosure.
Figure 17:
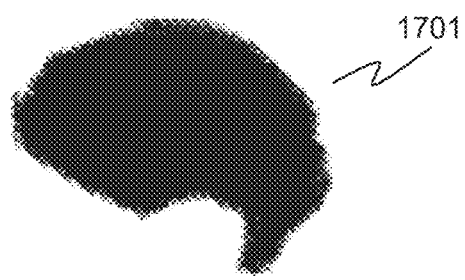
FIG. 17 is a schematic diagram illustrating an exemplary virtual ROI identified from the virtual area in FIG. 16 according to some embodiments of the present disclosure.
Figure 18:
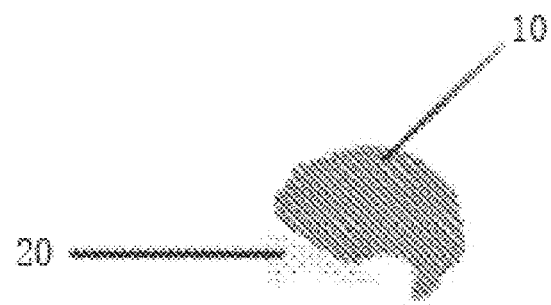
FIG. 18 is a schematic diagram illustrating an exemplary positioning image of an ROI corresponding to the virtual ROI in FIG. 17 according to some embodiments of the present disclosure.

FIG. 16 is a schematic diagram illustrating an exemplary virtual area of a virtual head according to some embodiments of the present disclosure. FIG. 17 is a schematic diagram illustrating an exemplary virtual ROI identified from the virtual area in FIG. 16 according to some embodiments of the present disclosure. FIG. 18 is a schematic diagram illustrating an exemplary positioning image of an ROI corresponding to the virtual ROI in FIG. 17 according to some embodiments of the present disclosure. The processing device 120B may identify a virtual ROI in the virtual area 1601 as illustrated in FIG. 16. The identified virtual ROI may be a region 1701 filled with black (also referred to as a virtual ROI 1701) as shown in FIG. 17. The processing device 120B may identify two segmented regions 10 and 20 in the positioning image illustrated in FIG. 18. The processing device 120B may determine a first degree of similarity between the segmented region 10 and the virtual ROI 1701 and a second degree of similarity between the segmented region 20 and the virtual ROI 1701, using a similarity algorithm. Exemplary similarity algorithms may include a Euclidean distance algorithm, a Manhattan distance algorithm, a Minkowski distance, a cosine similarity algorithm, a Jaccard similarity algorithm, a Pearson correlation algorithm, or the like, or any combination thereof. The processing device 120B may designate the segmented region 10 as an ROI corresponding to the virtual region 1701 (also referred to as an ROI 10) in the positioning image in response to determining that the first degree of similarity exceeds a predetermined threshold. The processing device 120 may determine a target area based on the ROI 10.

Figure 19:
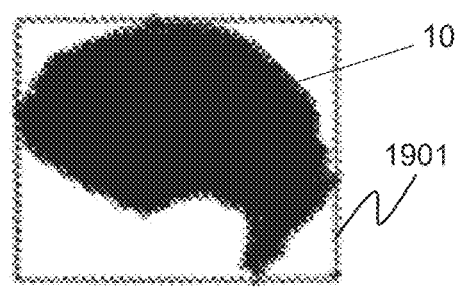
FIG. 19 is a schematic diagram illustrating an exemplary target area determined based on the ROI as shown in FIG. 18 according to some embodiments of the present disclosure.

FIG. 19 is a schematic diagram illustrating an exemplary target area determined based on the ROI as shown in FIG. 18 according to some embodiments of the present disclosure. As shown in FIG. 19, the target area 1901 may be of a rectangular shape. In some embodiments, the processing device 120B may determine one or more features points, e.g., the highest point of the ROI 10, the lowest point of the ROI 10, the leftmost point of the ROI 10, and the rightmost point of the ROI 10. The processing device 120B may construct a 2D coordinate system by designating a point in the ROI 10, e.g., an identified features point, as an origin of the 2D coordinate system. Merely by way of example, the processing device 120B may designate the origin of the 2D coordinate system being the identified lowest point of the ROI 10, an X-axis of the 2D coordinate system being horizontal, and a Y-axis of the 2D coordinate system being vertical. The processing device 120B may determine a left line that passes the leftmost point of the ROI 10 and is vertical to the X-axis, a right line that passes the rightmost point of the ROI 10 and is vertical to the Y-axis, an upper line that passes the highest point and is vertical to the Y-axis, and a lower line that passes the lowest line and be vertical to the Y-axis. A rectangle formed by the left line, the right line, the upper line, and the lower line may be designated as the target area 1901.

It should be noted that, according to operations 1210-1240, the target area relating to the subject may be determined automatically based on the model image and the positioning image, which may reduce the need for a manual operation by a user and cross-user variations, and improve the efficiency, accuracy, and/or consistency of the imaging process performed using the medical system 100.

It should be noted that the above description regarding process 1200 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, an additional operation for transforming the target area in the positioning image to a physical target area for scanning or treating the subject may be added after the operation 1240. As another example, an addition operation for causing the target area to be displayed to the user may be added after the operation 1240. The user may confirm whether the target area is suitable or make adjustment if needed. The processing device 120B may adjust the target area based on a response from the user. As still another example, operations 1220 and 1230 may be integrated into an operation.

Figure 15:
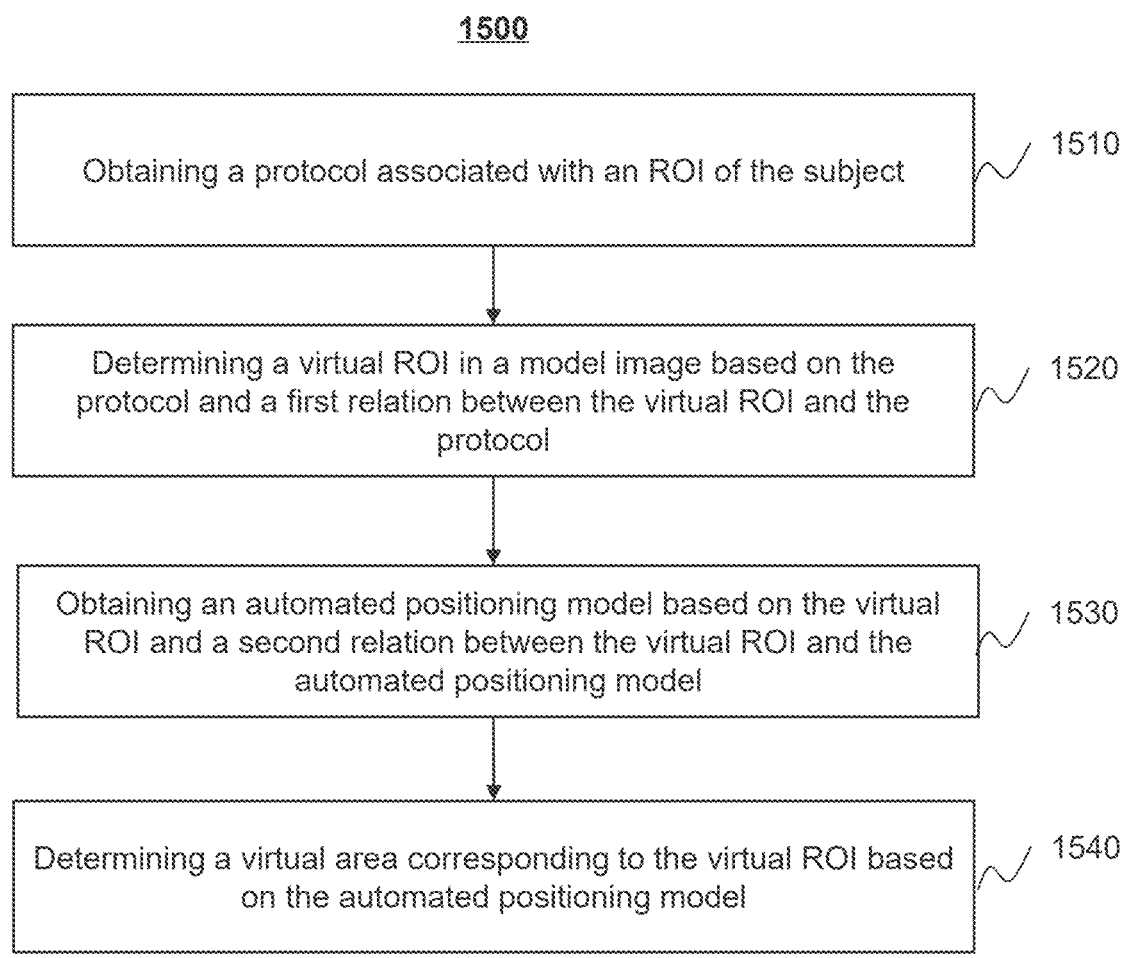
FIG. 15 is a schematic diagram illustrating an exemplary process for determining a virtual area in a model image according to some embodiments of the present disclosure.

FIG. 15 is a schematic diagram illustrating an exemplary process for determining a virtual area in a model image according to some embodiments of the present disclosure. In some embodiments, process 1500 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 1500. The operations of the illustrated process presented below are intended to be illustrative. In some embodiments, the process 1500 may be accomplished with one or more additional operations not described and/or without one or more of the operations discussed. Additionally, the order of the operations of process 1500 illustrated in FIG. 15 and described below is not intended to be limiting. In some embodiments, operation 1220 in FIG. 12 may be achieved by one or more operations of the process 1500.

In 1510, the processing device 120B (e.g., the protocol determination module 424) may obtain a protocol associated with the ROI of the subject.

The protocol may be a scan protocol and a treatment protocol. Different ROIs may correspond to different protocols. For example, for the ROI including the head of the subject to be scanned, the protocol may be a scan protocol corresponding to a head scan. As another example, for the ROI including the chest of the subject to be scanned, the protocol may be a scan protocol corresponding to a chest scan.

In 1520, the processing device 120B (e.g., the virtual area determination module 422) may determine the virtual ROI in the model image based on the protocol and a first relation between the virtual ROI and the protocol.

In some embodiments, the first relation between the virtual ROI and the protocol may be predetermined (e.g., by the manufacture of the medical system 100 or a portion thereof) and stored in a storage device (e.g., the storage device 130, storage 220, and/or storage 390). The processing device 120B may retrieve the first relation from the storage device. In some embodiments, the first relation may be represented in the form of a character, a text, a code, a number, or the like, or any combination thereof. Merely by way of example, a protocol associated with the head of the subject may be designated as a number of "4," and a virtual head (or a set of virtual ROIs of the virtual head) may be designated as a number of "2." The first relation between the protocol associated with the head and the virtual head may be designated as "2-4." The processing device 120B may determine the virtual head in the model image based on the protocol associated with the head and the first relation of "2-4."

In 1530, the processing device 120B (e.g., the virtual area determination module 422) may obtain an automated positioning model based on the virtual ROI and a second relation between the virtual ROI and the automated positioning model. As used herein, the second relation may describe a correspondence between the virtual ROI and the automated positioning model.

In some embodiments, the automated positioning model may be a trained model that is used to output a virtual area corresponding to a virtual ROI by inputting the virtual ROI into the automated positioning model. Different virtual ROIs may correspond to different automated positioning models. For example, the automated positioning model may include an automated positioning model of a virtual head, an automated positioning model of a virtual chest, an automated positioning model of a virtual leg, or the like, or any combination thereof.

In some embodiments, the second relation between the virtual ROI and the automated positioning model may be predetermined and stored in a storage device (e.g., the storage device 130, storage 220, and/or storage 390). The processing device 120B may retrieve the second relation from the storage device. In some embodiments, the second relation may be represented in the form of a character, a text, a code, a number, or the like, or any combination thereof. Merely by way of example, a virtual head (or a set of virtual ROIs of the virtual head) may be designated as a character of "A," and an automated positioning model of the virtual head may be designated as a character of "a." The second relation between the virtual head and the automated positioning model of the head may be designated as "A-a." As another example, a virtual chest (or a set of virtual ROIs of the virtual chest) may be designated as a character of "B," and an automated positioning model of the virtual chest may be designated as a character of "b." The second relation between the virtual chest and the automated positioning model of the chest may be designated as "B-b." As still another example, a virtual head (or a set of virtual ROIs of the virtual head) "A" may include three virtual ROIs "a1," "a2," and "a3." Each of the three virtual ROIs "a1," "a2" and "a3" may correspond to an automated positioning model, and the virtual head "A" may correspond to three automated positioning models.

In 1540, the processing device 120B (e.g., the target area determination module 423) may determine the virtual area corresponding to the virtual ROI based on the automated positioning model.

In some embodiments, the processing device 120B may input the virtual into the automated positioning model, and based on the automated positioning model output the virtual area. The processing device 120B may display the virtual area on the model image and the virtual ROI in the model image may be within the virtual area.

In some embodiments, the model image, the automated positioning image, the protocol, etc., described elsewhere in the present disclosure may be updated and added by one or more of manufacturers or vendors that provide them. The manufactures or vendors may be different from that provides the medical system 100, or at least one of the manufactures or venders may be the same as that provides the medical system 100.

It should be noted that the above description regarding the processes 1500 is merely provided for the purposes of illustration, and not intended to limit the scope of the present disclosure. For persons having ordinary skills in the art, multiple variations and modifications may be made under the teachings of the present disclosure.

However, those variations and modifications do not depart from the scope of the present disclosure. The operations of the illustrated process presented above are intended to be illustrative. In some embodiments, the process 1500 may be accomplished with one or more additional operations not described and/or without one or more of the operations discussed. For example, operations 1520 and 1530 may be integrated into an operation. The first relation and the second relation may be merged into a relation. The processing device 120B may determine an automated positioning image based on the virtual ROI and the relation.

Figure 20:
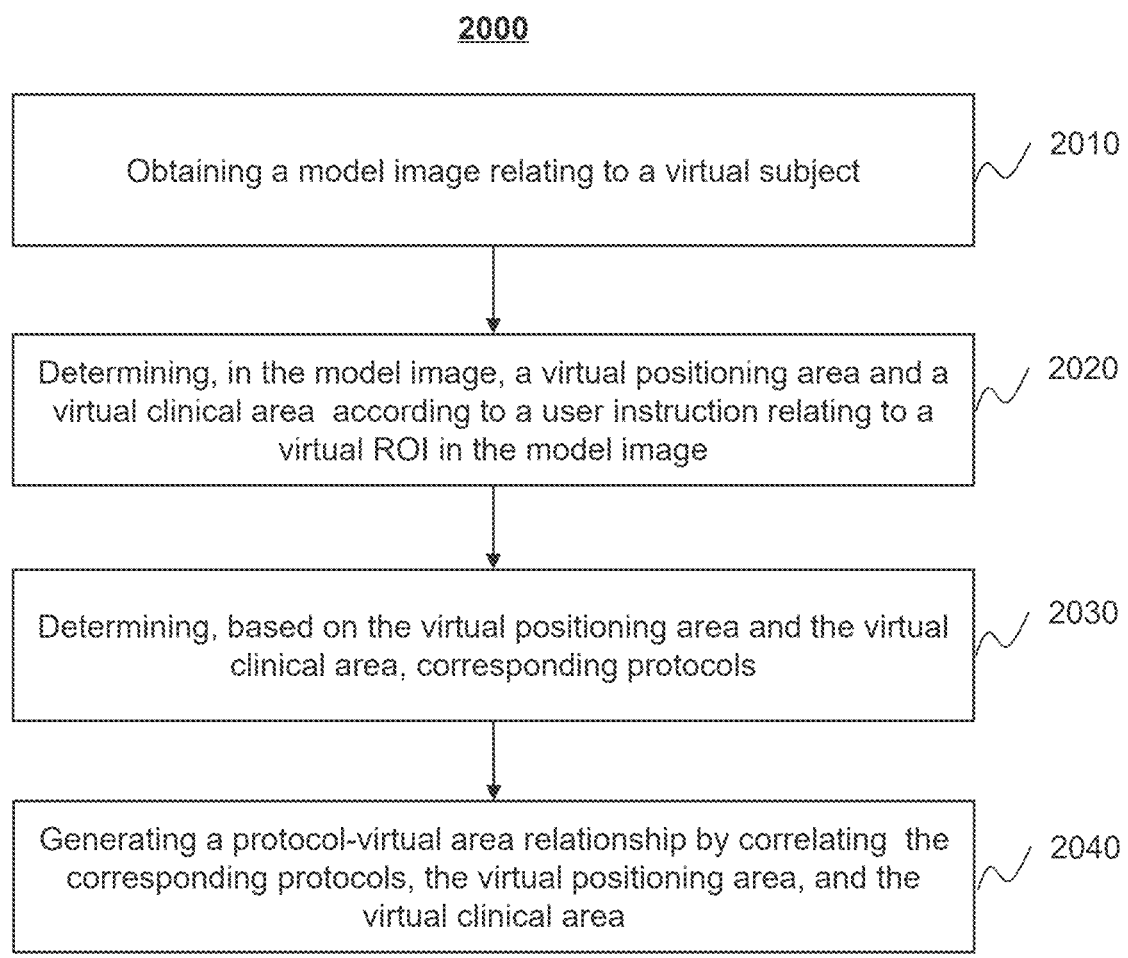
FIG. 20 is a schematic diagram illustrating an exemplary process for determining a protocol-virtual area relationship according to some embodiments of the present disclosure.

FIG. 20 is a schematic diagram illustrating an exemplary process for determining a protocol-virtual area relationship according to some embodiments of the present disclosure. In some embodiments, process 2000 may be implemented as a set of instructions (e.g., an application) stored in a storage device (e.g., the storage device 130, storage 220, and/or storage 390). The processing device 120C (e.g., the processor 210, the CPU 340, and/or one or more modules illustrated in FIG. 4C) may execute the set of instructions, and when executing the instructions, the processing device 120C may be configured to perform the process 2000. The operations of the illustrated process presented below are intended to be illustrative. In some embodiments, the process 2000 may be accomplished with one or more additional operations not described and/or without one or more of the operations discussed. Additionally, the order of the operations of process 2000 illustrated in FIG. 20 and described below is not intended to be limiting. In some embodiments, the protocol-virtual area relationship used in operation 1220 in FIG. 12 may be achieved according to one or more operations of the process 1500. In some embodiments, the process 2000 may be performed by another device or system other than the medical system 100, e.g., a device or system of a vendor or a manufacturer. In some embodiments, the process 2000 may be performed online or offline. For illustration purposes, the implementation of the process 2000 by the processing device 120C is described as an example.

In 2010, the processing device 120C (e.g., the acquisition module 431) may obtain a model image relating to a virtual subject. As used herein, the model image relating to the virtual subject may refer to an image including a plurality of virtual ROIs of the virtual subject. The model image may be used to provide a virtual representation of or reference for a physical shape, an anatomical structure, a lesion location and/or anatomy, or the like, or any combination thereof, of a subject to be imaged or treated.

In some embodiments, the model image may be the same as or similar to the model image as described in operation 1210 in FIG. 12, the description of which is not repeated herein.

In 2020, the processing device 120C (e.g., the virtual area determination module 432) may determine, in the model image, a virtual positioning area and a virtual clinical area according to a user instruction relating to a virtual ROI in the model image. The virtual positioning area may correspond to an area in the virtual subject where a scan is simulated to obtain a positioning image of the virtual subject. The virtual clinical area may correspond to an area in the virtual subject where an imaging scan or treatment is simulated on the virtual subject.

In some embodiments, a user instruction may be provided by a user (e.g., the technician or doctor) dragging or drawing a shape (e.g., a rectangular shape, a rhombus shape, a circular shape, an elliptical shape, etc.) on the model image. The virtual ROI may be within the shape. The processing device 120C may determine a preliminary virtual positioning area and a preliminary virtual clinical area based on the user instruction. In some embodiments, a shape of the preliminary virtual positioning area and a shape of the preliminary virtual clinical area may be in accordance with the shape dragged or drawn by the user. The processing device 120C may determine the virtual positioning area and the virtual clinical area based on the preliminary positioning area and the preliminary virtual clinical area. Either one of the virtual positioning area and the virtual clinical area may be of a rectangular shape.

Figure 21:
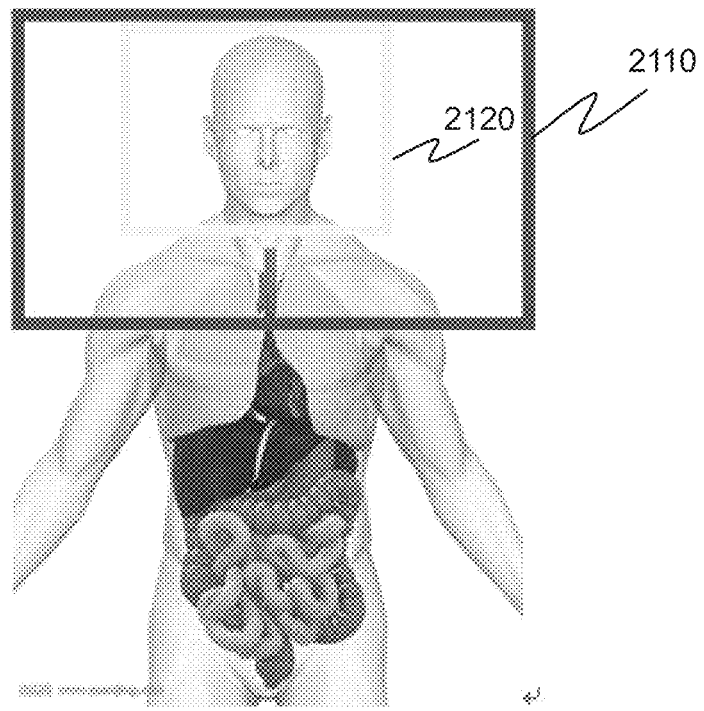
FIG. 21 is a schematic diagram illustrating exemplary virtual areas of a virtual head according to some embodiments of the present disclosure.
Figure 22:
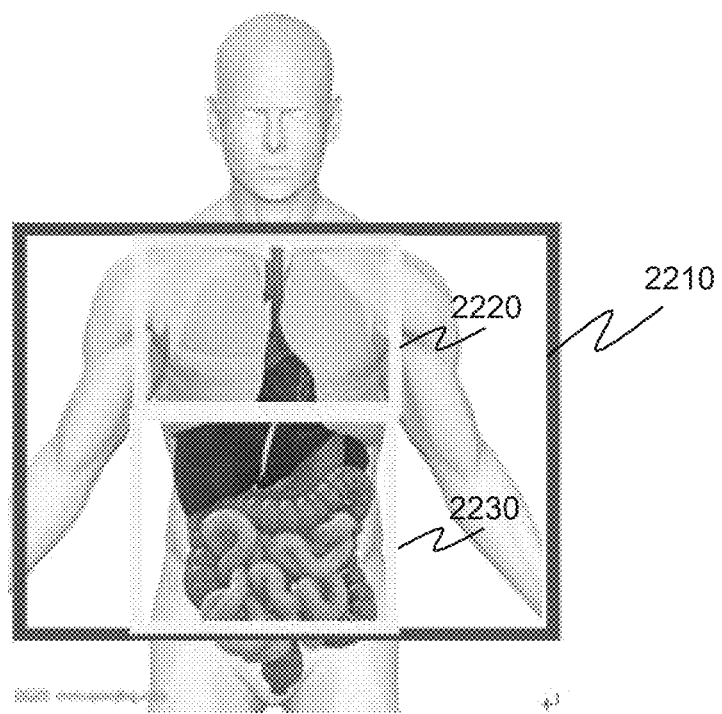
FIG. 22 is a schematic diagram illustrating exemplary virtual areas of a virtual chest and abdomen according to some embodiments of the present disclosure.

For example, FIG. 21 is a schematic diagram illustrating exemplary virtual areas of a virtual head according to some embodiments of the present disclosure. As shown in FIG. 21, a block 2110 may represent a virtual positioning area of the virtual head, and a block 2120 may represent a virtual clinical area of the virtual head. As another example, FIG. 22 is a schematic diagram illustrating exemplary virtual areas of a virtual chest and abdomen according to some embodiments of the present disclosure. As shown in FIG. 22, a block 2210 may represent a virtual positioning area of the virtual chest and abdomen, a block 2220 may represent a virtual clinical area of the virtual chest and the abdomen, and a block 2230 may represent a virtual clinical area of the virtual abdomen of the virtual chest and the abdomen.

In some embodiments, the processing device 120C may determine the virtual positioning image and the virtual clinical area based on the preliminary positioning area and the preliminary clinical area according to a preset rule. Merely by way of example, for the preliminary virtual clinical area being of a rectangular shape, the processing device 120C may designate the preliminary clinical area as the virtual clinical area. As another example, for the preliminary virtual positioning area being of a circular shape, the processing device 120C may identify the highest point, the lowest point, the leftmost point, and the rightmost point farthest of the preliminary virtual positioning area. The processing device 120C may determine a rectangular region based on the identified highest point, the lowest point, the leftmost point, and the rightmost point of the preliminary virtual positioning image as a midpoint of each side of the rectangular region, respectively. The processing device 120C may designate the rectangular region as the virtual positioning area.

In 2030, the processing device 120C (e.g., the protocol determination module 433) may determine, based on the virtual positioning area and the virtual clinical area, corresponding protocols.

In some embodiments, the corresponding protocols may include a positioning protocol and a clinical protocol. The positioning protocol may include correspondence between positioning areas in the virtual subject and virtual positioning areas in the model image. The clinical protocol may include correspondence between clinical areas in the virtual subject and virtual clinical areas in the model image. In some embodiments, the processing device 120C may determine the positioning area and the clinical area based on a virtual positioning posture of the virtual subject. The virtual positioning posture of the virtual subject may be determined or selected by the user before determining the positioning area and the clinical area. More descriptions regarding the determination of the positioning area and the clinical area may be found elsewhere in the present disclosure (e.g., FIG. 23 and the descriptions thereof). In some embodiments, the corresponding protocols may include reconstruction parameters such as reconstruction areas of different ROIs which may be determined based on spatial relationships between the different ROIs. More descriptions regarding the determination of the spatial relationships may be found elsewhere in the present disclosure (e.g., FIG. 24 and the descriptions thereof).

In some embodiments, a protocol may be referred to using a protocol name corresponding to an area for imagining or treatment. For example, a protocol corresponding to the imaging or treatment of a head may be referred to as TOPD. A protocol corresponding to a clinical area of a head may be referred to as TOPL.

In 2040, the processing device 120C (e.g., the relation determination module 434) may generate a protocol-virtual area relationship by correlating the corresponding protocols, the virtual positioning areas, and the virtual clinical areas.

In some embodiments, the processing device 120C may determine a positioning protocol-virtual positioning area relationship based on the positioning protocol and the virtual positioning area. The processing device 120C may determine a clinical protocol-virtual clinical area relationship based on the clinical protocol and the virtual clinical area. The processing device 120C may generate the protocol-virtual area relationship based on the positioning protocol-virtual positioning area relationship and the clinical protocol-virtual clinical area relationship. The positioning protocol-virtual positioning area relationship may be designated as "A-K1." If the clinical protocol is designated as "B," and the clinical protocol is designated as "K2," the clinical protocol-virtual clinical area relationship may be designated as "B-K2." The corresponding protocol-virtual area relationship may be designated as "A-K1-B-K2."

In some embodiments, the virtual positioning area and the virtual clinical area may correspond to a same virtual ROI in the model image. The processing device 120C may determine a protocol-virtual area relationship relating to the same virtual ROI. The same virtual ROI may be a single virtual ROI or a virtual ROI including a plurality of virtual sub-ROIs. At least two of the plurality of virtual sub-ROIs may be next to each other, such as a virtual chest and a virtual abdomen, or a virtual head and a virtual neck. For example, the processing device 120C may determine a positioning protocol-virtual positioning area relationship relating to a particular virtual ROI based on a positioning protocol relating to the particular virtual ROI and a virtual positioning area relating to the particular virtual ROI. The processing device 120C may determine a clinical protocol-virtual clinical area relationship relating to the particular virtual ROI based on a clinical protocol relating to the particular virtual ROI and a virtual clinical area relating to the particular virtual ROI. The processing device 120C may generate a protocol-virtual area relationship relating to the particular virtual ROI based on the positioning protocol-virtual positioning area relationship relating to the particular virtual ROI and the clinical protocol-virtual clinical area relationship relating to the particular virtual ROI. The particular virtual ROI may be a virtual head, a virtual chest, a virtual leg, a virtual chest and abdomen, a virtual head and neck, etc.

For a particular virtual ROI being the virtual chest, the positioning protocol relating to the virtual chest may be designed as "XD," the clinical protocol relating to the virtual chest may be designated as "XL," the positioning area relating to the virtual chest may be designated as "XDS, and the clinical area relating to the virtual chest may be designated as "XLS." The positioning protocol-virtual positioning area relationship relating to the virtual chest may be determined to be "XD-XDS," and the clinical protocol-virtual clinical area relationship relating to the virtual chest may be determined to be "XL-XLS." The protocol-virtual area relationship relating to the virtual chest may be determined to be "XD-XDS-XL-XLS."

For a particular virtual ROI being the virtual abdomen, the positioning protocol relating to the virtual abdomen may be designed as "FD," the clinical protocol relating to the virtual abdomen may be designated as "FL," the positioning area relating to the virtual abdomen may be designated as "FDS, and the clinical area relating to the virtual abdomen may be designated as "FLS." The positioning protocol-virtual positioning area relationship relating to the virtual abdomen may be determined to be "FD-FDS," and the clinical protocol-virtual clinical area relationship relating to the virtual abdomen may be determined to be "FL-FLS." The protocol-virtual area relationship relating to the virtual chest may be determined to be "FD-FDS-FL-FLS."

For a particular virtual ROI being the virtual chest and abdomen, the positioning protocol relating to the virtual chest and abdomen may be designed as "XFD," the clinical protocol relating to the virtual chest and abdomen may be designated as "XFL," the positioning area relating to the virtual chest and abdomen may be designated as "XFDS, and the clinical area relating to the virtual chest and abdomen may be designated as "XFLS." The positioning protocol-virtual positioning area relationship relating to the virtual chest and abdomen may be determined to be "XFD-XFDS," and the clinical protocol-virtual clinical area relationship relating to the virtual chest and abdomen may be determined to be "XFL-XFLS." The protocol-virtual area relationship relating to the virtual chest and abdomen may be determined to be "XFD-XFDS-XFL-XFLS."

In some embodiments, the virtual positioning area may correspond to a virtual ROI in the model image, and the virtual clinical area may correspond to a plurality of virtual sub-ROIs of the virtual ROI in the model image. That is, the virtual ROI may include the plurality of virtual sub-ROIs, of which at least two may be next to each other. Each of the plurality of virtual sub-ROIs may correspond to a virtual clinical sub-area, and the virtual clinical sub-areas may form the virtual clinical area. The processing device 120B may obtain a positioning protocol based on the virtual positioning area that corresponds to the virtual ROI in the model image, and obtain clinical protocols each of which corresponds to one of the virtual clinical sub-areas. The processing device 120B may determine the protocol-virtual area relationship based on the positioning protocol and the clinical protocols. For a virtual ROI being a virtual chest and abdomen, the positioning protocol-virtual positioning area relationship relating to the chest and abdomen may be determined to be "XFD-XFDS," the clinical protocol-virtual protocol area relating to a virtual chest may be determined to be "XL-XLS," and the clinical protocol-virtual protocol area relationship relating to a virtual abdomen may be determined to be "XL-XLS." The protocol-virtual area relationship relating to the virtual chest and abdomen may be determined to be "XFD-XFDS-XL-XLS-FL-FLS."

In some embodiments, the protocol-virtual area relationship may be stored in concert with the model image. For example, during the application of the protocol-virtual relationship, the model image may be displayed with a protocol list including a plurality of protocol which may be selected by a user. When the user selects a protocol associated with a particular ROI, the processing device 120B may directly display a virtual area associated with a virtual ROI corresponding to the particular ROI in the model image. As another example, when the user selects a particular virtual ROI in the model image, one or more protocols associated with an ROI corresponding to the particular virtual ROI may be displayed with the model image, and the user may select one or more protocols suitable for clinic. As still another example, to determine a target area relating to the chest of the subject, the processing device 120C may obtain a protocol associated with the chest and the protocol-virtual area relationship relating to the virtual chest, which may be similar to that described in FIG. 12, improving an efficiency of the medical system 100.

It should be noted that the above description regarding the processes 2000 is merely provided for the purposes of illustration, and not intended to limit the scope of the present disclosure. For persons having ordinary skills in the art, multiple variations and modifications may be made under the teachings of the present disclosure.

However, those variations and modifications do not depart from the scope of the present disclosure. The operations of the illustrated process presented above are intended to be illustrative. In some embodiments, the process 2000 may be accomplished with one or more additional operations not described and/or without one or more of the operations discussed. For example, operations 2030 and 2040 may be integrated into an operation.

Figure 23:
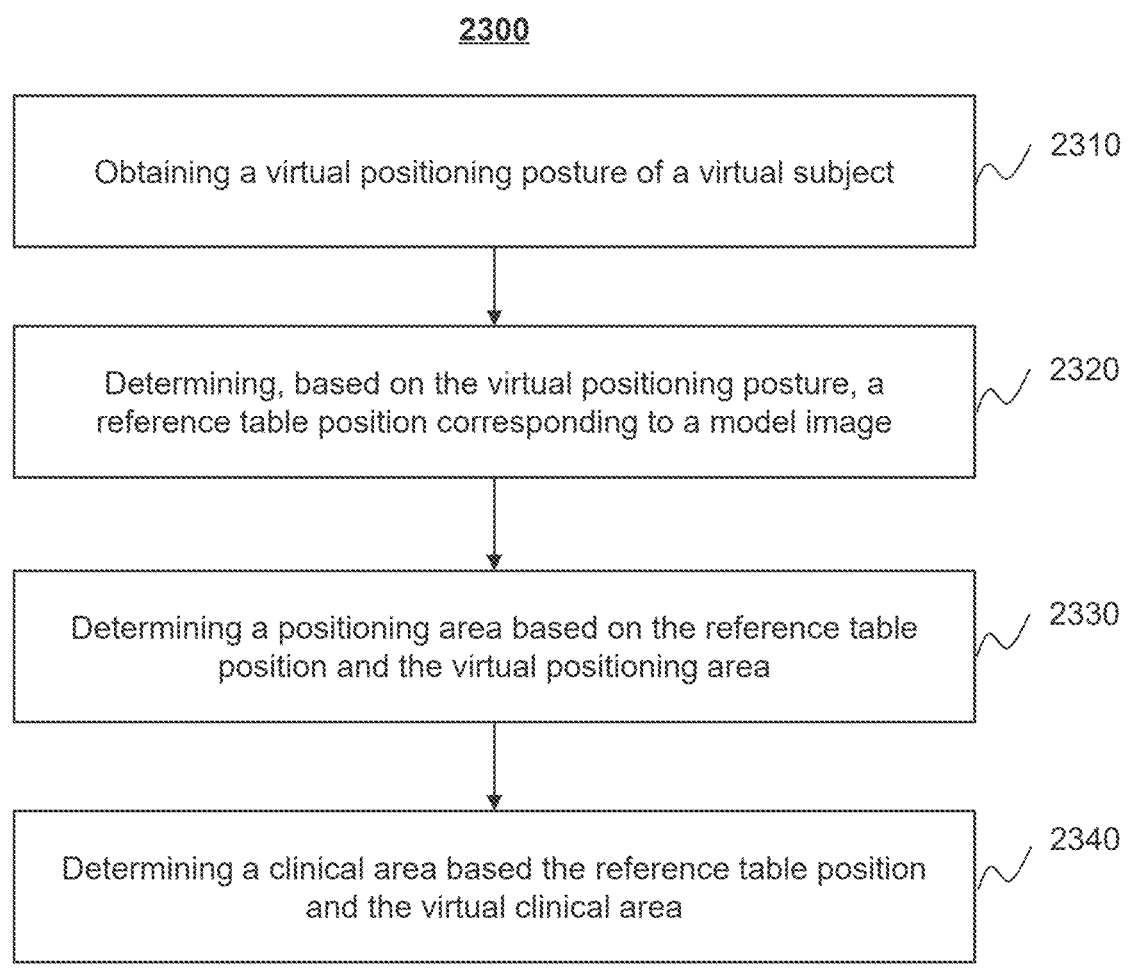
FIG. 23 is a schematic diagram illustrating an exemplary process for determining a positioning area and a clinical area according to some embodiments of the present disclosure.

FIG. 23 is a schematic diagram illustrating an exemplary process for determining a positioning area and a clinical area according to some embodiments of the present disclosure. In some embodiments, process 2300 may be implemented as a set of instructions (e.g., an application) stored in a storage device (e.g., the storage device 130, storage 220, and/or storage 390). The processing device 120C (e.g., the processor 210, the CPU 340, and/or one or more modules illustrated in FIG. 4C) may execute the set of instructions, and when executing the instructions, the processing device 120C may be configured to perform the process 2300. The operations of the illustrated process presented below are intended to be illustrative. In some embodiments, the process 2300 may be accomplished with one or more additional operations not described and/or without one or more of the operations discussed. Additionally, the order of the operations of process 2300 illustrated in FIG. 23 and described below is not intended to be limiting. In some embodiments, operation 2030 in FIG. 20 may be achieved by one or more operations of the process 2300. In some embodiments, the process 2300 may be performed by another device or system other than the medical system 100, e.g., a device or system of a vendor or a manufacturer.

In some embodiments, the process 2300 may be performed online or offline. For illustration purposes, the implementation of the process 2300 by the processing device 120C is described as an example.

In 2310, the processing device 120C (e.g., the protocol determination module 433) may obtain the virtual posture of a virtual subject.

In some embodiments, the virtual posture of the virtual subject may be with respect to a table of a medical system by which the virtual subject is simulated to be scanned or treated. Exemplary virtual posture may include Head First-Supine (HFS), Head First-Prone (HFP), Head First-Decubitus Right (HFDR), Head First-Decubitus Left (HFDL), Feet First-Decubitus Right (FFDR), Feet First-Decubitus Lef (FFDL), Feet First-Prone (FFP), Feet First-Supine (FFS), etc. Merely by way of example, the virtual subject may be a human being with a weight of 70 kg, and a height of 175 cm, and assumed to be scanned by a CT device. The virtual posture of the virtual subject may be designated to be HFS, that is, the head of the virtual subject may be located at a head support of the CT device.

In 2320, the processing device 120C (e.g., the protocol determination module 433) may determine, based on the virtual positioning posture, a reference table position corresponding to the model image.

In some embodiments, the reference table position corresponding to the model image may refer to a table position when the head of the virtual subject is located at or in the vicinity of an isocenter of the medical system. For example, the reference table position corresponding to the model image may refer to a table position when the head of the virtual subject is located at an isocenter of the CT device.

In 2330, the processing device 120C (e.g., the protocol determination module 433) may determine the positioning area based on the reference table position and the virtual positioning area.

In some embodiments, the processing device 120C may determine a length of the virtual positioning area along a direction that the virtual subject lies in the model image. The processing device 120C may determine a mapping relation based on a virtual height of the virtual subject in the model image and a physical height of the virtual subject (e.g., 175 cm). The processing device 120C may determine the length of the positioning area based on the length of the virtual positioning area and the mapping relation. The processing device 120C may determine the positioning area based on the length of the positioning area and the reference table position. For example, the positioning area may be represented by a start table position (e.g., 300), an end table position (e.g., 700) and the length (e.g., 400) of the positioning area (also referred to as absolute table positions). The start table position may correspond to a nearest position of the positioning area to the position of the head. The end table position may correspond to a furthest position of the positioning area to the position of the head. As another example, the positioning area may be represented by a start character (e.g., a character of "*"), an end character a character of "*") and the length (e.g., 400) of the positioning area (also referred to as absolute table positions). The start character may correspond to a nearest position of the positioning area to the position of the head. The end character may correspond to a furthest position of the positioning area to the position of the head.

In 2340, the processing device 120C (e.g., the protocol determination module 433) may determine the clinical area based on the reference table position and the virtual clinical area.

In some embodiments, the processing device 120C may determine the clinical area in a manner the same as or similar to that used to determine the positioning area, and is not repeated here.

It should be noted that the above description regarding the processes 2300 is merely provided for the purposes of illustration, and not intended to limit the scope of the present disclosure. For persons having ordinary skills in the art, multiple variations and modifications may be made under the teachings of the present disclosure.

However, those variations and modifications do not depart from the scope of the present disclosure. The operations of the illustrated process presented above are intended to be illustrative. In some embodiments, the process 2300 may be accomplished with one or more additional operations not described and/or without one or more of the operations discussed. For example, operations 2330 and 2340 may be integrated into an operation.

Figure 24:
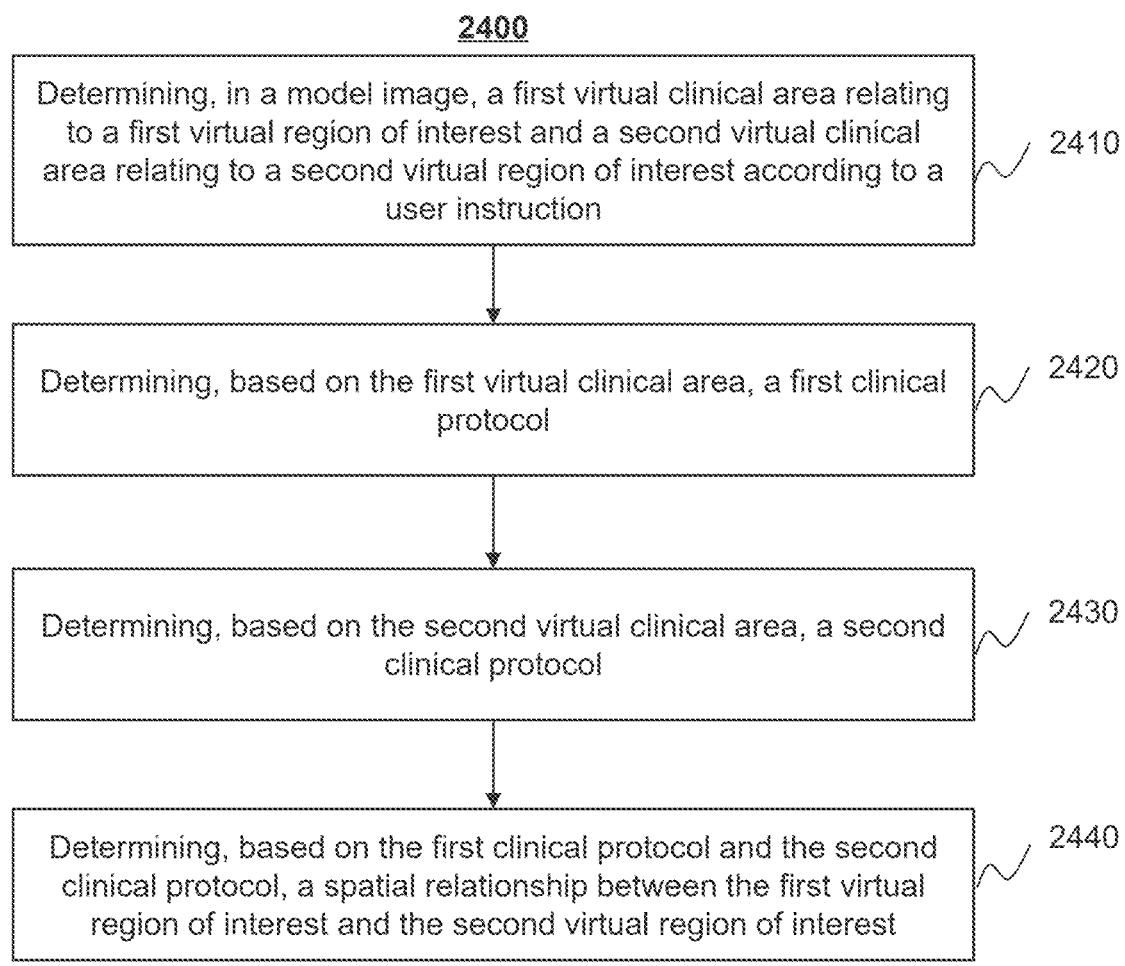
FIG. 24 is a schematic diagram illustrating an exemplary process for determining a spatial relationship between a first virtual ROI and a second virtual ROI according to some embodiments of the present disclosure.

FIG. 24 is a schematic diagram illustrating an exemplary process for determining a spatial relationship between a first virtual ROI and a second virtual ROI according to some embodiments of the present disclosure. In some embodiments, process 2400 may be implemented as a set of instructions (e.g., an application) stored in a storage device (e.g., the storage device 130, storage 220, and/or storage 390). The processing device 120C (e.g., the processor 210, the CPU 340, and/or one or more modules illustrated in FIG. 4C) may execute the set of instructions, and when executing the instructions, the processing device 120C may be configured to perform the process 2400. The operations of the illustrated process presented below are intended to be illustrative. In some embodiments, the process 2400 may be accomplished with one or more additional operations not described and/or without one or more of the operations discussed. Additionally, the order of the operations of process 2400 illustrated in FIG. 24 and described below is not intended to be limiting. In some embodiments, the process 2400 may be performed by another device or system other than the medical system 100, e.g., a device or system of a vendor or a manufacturer. In some embodiments, the process 2400 may be performed online or offline. For illustration purposes, the implementation of the process 2400 by the processing device 120C is described as an example.

In 2410, the processing device 120C (e.g., the relation determination module 434) may determine, in a model image, a first virtual clinical area relating to the first virtual ROI and a second virtual clinical area relating to the second virtual ROI according to a user instruction. The first virtual ROI and the second virtual ROI may be non-overlapping in the model image. In some embodiments, the first virtual clinical area and the second virtual clinical area may be determined in a same or similar manner that is used to determine the virtual clinical area as described in operation 2020 in FIG. 20.

In 2420, the processing device 120C (e.g., the relation determination module 434) may determine, based on the first virtual clinical area, a first clinical protocol. The first clinical protocol may be determined in a same or similar manner that is used to determine the clinical protocol as described in operation 2030 in FIG. 20. The first clinical protocol may include a first clinical area corresponding to the first virtual ROI.

In 2430, the processing device 120C (e.g., the relation determination module 434) may determine, based on the second virtual clinical area, a second clinical protocol. The second clinical protocol may be determined in a same or similar manner that is used to determine the clinical protocol as described in operation 2030 in FIG. 20. The second clinical protocol may include a second clinical area corresponding to the second virtual ROI.

In 2440, the processing device 120C (e.g., the relation determination module 434) may determine, based on the first clinical protocol and the second clinical protocol, a spatial relationship between the first ROI and the second ROI.

In some embodiments, the processing device 120C may determine the spatial relationship based on the first clinical area of the first clinical protocol and the second clinical area of the second clinical protocol. The spatial relationship may be represented by a distance between the first virtual ROI and the second virtual ROI that is determined based on start table positions thereof. For example, the first virtual ROI may be a virtual chest and correspond to table positions of (60, 80). The second virtual ROI may be a virtual abdomen and correspond to table positions of (88, 102). A start table position of the virtual chest may be 60, and a start table position of the virtual abdomen may be 88. A difference between the two start table positions may be 28 and the spatial relationship between the virtual chest and the virtual abdomen may be determined based on the difference.

In some embodiments, the clinical protocol may include reconstruction parameters which may be determined by the processing device 120C and/or the user. The processing device 120C and/or the user may determine reconstruction areas of the reconstruction parameters based on the spatial relationship.

Figure 25:
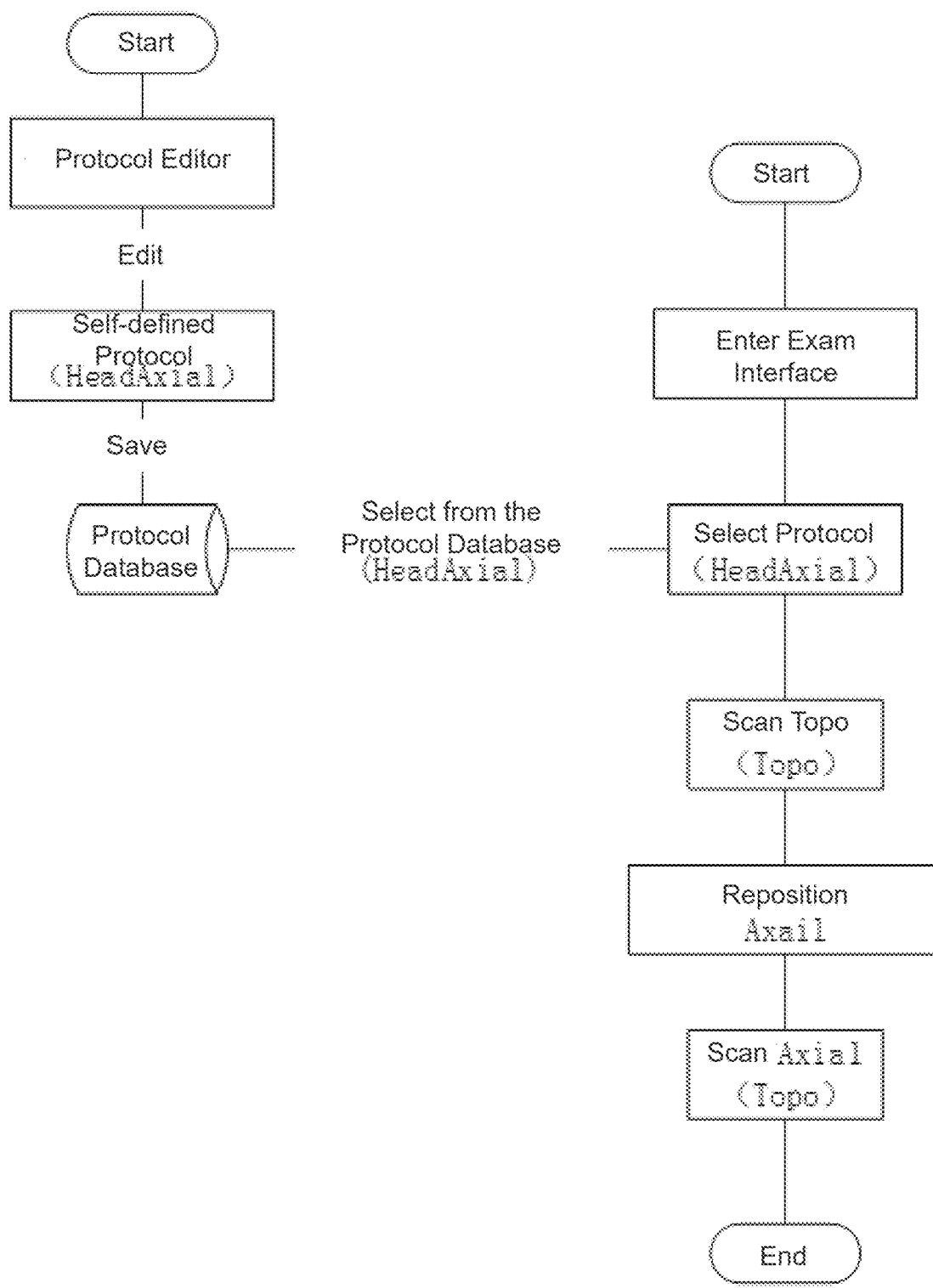
FIG. 25 is a schematic diagram illustrating an exemplary process for determining a protocol according to some embodiments of the present disclosure.

FIG. 25 is a schematic diagram illustrating an exemplary process for determining a protocol according to some embodiments of the present disclosure. As shown in FIG. 25, a protocol naming HeadAxial may be determined. The protocol HeadAxial may include a Topo protocol and an Axial protocol. The Topo protocol may be a positioning protocol. The Topo protocol may be a clinical protocol.

In an application of a protocol editor in which there is no suitable anatomical image to visualize and assist a user to determine the protocol, a user (e.g., a doctor, a technician) may need to input table positions and/or reconstruction parameters (e.g., a center X, a center Y, an FOV, etc.) of a protocol manually based on experience and estimations. The user may need to perform more adjustments due to, e.g., variations among subjects.

According to some embodiments of the present disclosure, during the determination of the protocol, edited by the protocol editor is inaccurate, a positioning image may be acquired based on the Topo protocol to provide position guidance for efficiently adjusting the Axial protocol.

According to one or more of operations 2010-2040, a model image is provided for assisting the user in determining the protocol (e.g., the clinical area and/or reconstruction area in the protocol), and/or determining a spatial relationship between different ROIs (which may facilitate the determination of image reconstruction areas associated with the different ROIs), thereby improving the accuracy and/or efficiency of the determination of the protocol.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims.

Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine, each of which has at least one processing device associated with a medical system and at least one storage device, for performing a medical operation on a subject situated on a table of the medical system, the medical system including a first device of a first modality and a second device of a second modality, the method comprising:

identifying, by the at least one processing device, based on one or more images of the subject, a second target area relating to the subject for performing a second operation using the second device;

determining, by the at least one processing device, based on the second target area, an initial target area relating to the subject for performing a first operation using the first device;

determining, by the at least one processing device, a first target area relating to the subject for performing the first operation using the first device by adjusting the initial target area;

controlling, by the at least one processing device, the second device to perform, based on the second target area, the second operation on the subject; and controlling, by the at least one processing device, the first device to perform, based on the first target area, the first operation on the subject;

wherein the determining, based on the second target area, an initial target area relating to the subject for performing a first operation using the first device includes:

transmitting, by the second device, at least one second parameter of the second target area to the first device as at least one corresponding parameter of the initial target area; or designating, by the at least one processing device, the at least one second parameter of the second target area as the at least one corresponding parameter of the initial target area.

2. The method of claim 1, wherein the second target area is characterized by the at least one second parameter including a center position of the second target area, a centerline of the second target area, an orientation of the second target area, or an angle of the second target area with respect to a surface of the table.

3. The method of claim 1, wherein the adjusting the initial target area includes:

identifying a region of interest of the subject associated with the first operation using the first device; and adjusting the initial target area based on the region of interest.

4. The method of claim 3, wherein the adjusting the initial target area based on the region of interest includes:

adjusting, based on the region of interest, a center position of the initial target area, a centerline of the initial target area, an orientation of the initial target area, an angle of the initial target area with respect to a surface of the table, a boundary of the initial target area, or a size of the initial target area.

5. The method of claim 1, wherein the adjusting the initial target area includes:

adjusting the initial target area according to a preset adjustment strategy.

6. The method of claim 5, wherein the preset adjustment strategy includes at least one of:

a parameter that does not change a size of the initial target area has a higher priority than a parameter that changes the size of the initial target area in an adjustment process of adjusting the initial target area, or a parameter that changes the size of the initial target area by a relatively less extent has a higher priority than a parameter that changes the size of the initial target area by a relatively large extent in the adjustment process.

7. The method of claim 1, wherein the one or more images include a model image and a positioning image, and the identifying a second target area relating to the subject for performing a second operation using the second device includes:

obtaining the model image corresponding to the subject;

determining in the model image a virtual area corresponding to the second target area;

obtaining the positioning image of the subject; and determining, based on the virtual area and the positioning image, the second target area relating to the subject.

8. The method of claim 1, wherein the one or more images include a positioning image, and the identifying a second target area relating to the subject for performing a second operation using the second device includes:

determining the second target area based on the positioning image of the subject that provides position information of the subject.

9. The method of claim 8, wherein the determining the second target area based on the positioning image of the subject includes:

identifying a region of interest (ROI) of the subject in the positioning image;

causing the table to move to a target table position in which the ROI of the subject is located at or in a vicinity of an isocenter of the second device; and determine the second target area based on the ROI of the subject such that the ROI of the subject falls within the second target area.

10. The method of claim 1, wherein at least one of the first device or the second device is an imaging device or a treatment device.

11. The method of claim 1, wherein the first device and the second device are imaging devices, the method further including:

acquiring first image data by performing the first operation using the first device;

acquiring second image data by performing the second operation using the second device; and generating a fusion image based on the first image data and the second image data.

12. The method of claim 11, wherein the first operation and the second operation are performed synchronously.

13. The method of claim 2, wherein the initial target area is characterized by at least one parameter including a center position of the initial target area, a centerline of the initial target area, an orientation of the initial target area, or an angle of the initial target area with respect to the surface of the table.

14. The method of claim 13, wherein the adjusting the initial target area includes:

adjusting the at least one parameter of the initial target area.

15. The method of claim 13, further comprising:

before adjusting the initial target area, designating the at least one second parameter of the second target area as the at least one parameter of the initial target area.

16. The method of claim 1, wherein the first operation and the second operation are imaging operations, and the method further comprises:

fusing an image generated by the first operation and an image generated by the second operation for display.

17. A system for performing a medical operation on a subject situated on a table of a medical system, the medical system including a first device of a first modality and a second device of a second modality, the system comprising:

at least one storage device including a set of instructions; and at least one processing device associated with the medical system, configured to communicate with the at least one storage device, wherein when executing the set of instructions, the at least one processing device is configured to cause the system to perform operations including:

identifying, by the at least one processing device, based on one or more images of the subject, a second target area relating to the subject for performing a second operation using the second device;

determining, by the at least one processing device, based on the second target area, an initial target area relating to the subject for performing a first operation using the first device;

determining by the at least one processing device, a first target area relating to the subject for performing the first operation using the first device by adjusting the initial target area;

controlling, by the at least one processing device, the second device to perform, based on the second target area, the second operation on the subject; and controlling, by the at least one processing device, the first device to perform, based on the first target area, the first operation on the subject, wherein the determining, based on the second target area, an initial target area relating to the subject for performing a first operation using the first device includes:

transmitting, by the second device, at least one second parameter of the second target area to the first device as at least one corresponding parameter of the initial target area; or designating, by the at least one processing device, the at least one second parameter of the second target area as the at least one corresponding parameter of the initial target area.

18. The system of claim 17, wherein the adjusting the initial target area includes:

identifying a region of interest of the subject associated with the first operation using the first device; and adjusting the initial target area based on the region of interest.

19. The system of claim 17, wherein the adjusting the initial target area based on the region of interest includes:

adjusting, based on the region of interest, a center position of the initial target area, a centerline of the initial target area, an orientation of the initial target area, an angle of the initial target area with respect to a surface of the table, a boundary of the initial target area, or a size of the initial target area.

20. A non-transitory computer readable medium storing instructions for performing a medical operation on a subject situated on a table of a medical system, the medical system including a first device of a first modality and a second device of a second modality, the instructions, when executed by at least one processing device associated with a medical system, causing the at least one processing device to implement a method comprising:

identifying, by the at least one processing device, based on one or more images of the subject, a second target area relating to the subject for performing a second operation using the second device;

determining, by the at least one processing device, based on the second target area, an initial target area relating to the subject for performing a first operation using the first device;

determining, by the at least one processing device, a first target area relating to the subject for performing the first operation using the first device by adjusting the initial target area;

controlling, by the at least one processing device, the second device to perform, based on the second target area, the second operation on the subject; and controlling, by the at least one processing device, the first device to perform, based on the first target area, the first operation on the subject, wherein the determining, based on the second target area, an initial target area relating to the subject for performing a first operation using the first device includes:

transmitting, by the second device, at least one second parameter of the second target area to the first device as at least one corresponding parameter of the initial target area; or designating, by the at least one processing device, the at least one second parameter of the second target area as the at least one corresponding parameter of the initial target area.

\* \* \* \* \*